United States Patent
Clark, III et al.

(10) Patent No.: US 8,518,069 B2
(45) Date of Patent: *Aug. 27, 2013

(54) DISSECTION HANDPIECE AND METHOD FOR REDUCING THE APPEARANCE OF CELLULITE

(75) Inventors: Robert L. Clark, III, Hayward, CA (US); James E. Chomas, Boulder, CO (US); Adnan I. Merchant, Fremont, CA (US); Ben F. Brian, III, Menlo Park, CA (US)

(73) Assignee: Cabochon Aesthetics, Inc., Menlo Park, CA (US)

( * ) Notice: Subject to any disclaimer, the term of this patent is extended or adjusted under 35 U.S.C. 154(b) by 592 days.

This patent is subject to a terminal disclaimer.

(21) Appl. No.: 12/787,382

(22) Filed: May 25, 2010

(65) Prior Publication Data

US 2010/0228182 A1 Sep. 9, 2010

Related U.S. Application Data

(63) Continuation-in-part of application No. 12/555,746, filed on Sep. 8, 2009, which is a continuation-in-part of application No. 11/515,634, filed on Sep. 5, 2009, now abandoned, and a continuation-in-part of application No. 11/334,794, filed on Jan. 17, 2006, now Pat. No. 7,588,547, and a continuation-in-part of application No. 12/247,853, filed on Oct. 8, 2008, now abandoned.

(60) Provisional application No. 60/715,398, filed on Sep. 7, 2005, provisional application No. 60/978,607, filed on Oct. 9, 2007, provisional application No. 61/232,385, filed on Aug. 7, 2009, provisional application No. 61/286,750, filed on Dec. 15, 2009.

(51) Int. Cl.
*A61B 17/32* (2006.01)

(52) U.S. Cl.
USPC .......................... 606/171; 606/167; 606/172

(58) Field of Classification Search
USPC ................ 606/161–162, 166–167, 170–172, 606/185, 190, 191, 198; 600/131, 132, 135–137, 565, 571; 604/115–117, 542
See application file for complete search history.

(56) References Cited

U.S. PATENT DOCUMENTS 3,590,808 A 7/1971 Muller
3,991,763 A 11/1976 Genese
(Continued)

FOREIGN PATENT DOCUMENTS

CN 201131982 Y 10/2008
DE 3838530 A1 5/1990
(Continued)

OTHER PUBLICATIONS

Albrecht, T. et al., Guidelines for the Use of Contrast Agents in Ultrasound, Ultraschall in Med 2004, Jan. 2004, pp. 249-256, vol. 25.
(Continued)

*Primary Examiner* — Elizabeth Houston
*Assistant Examiner* — David Eastwood
(74) *Attorney, Agent, or Firm* — Fulwider Patton LLP

(57) ABSTRACT

A dermatological skin treatment device is provided. The device comprises a handpiece and a cutting tool, wherein the tool is inserted through the conduit and percutaneously inserted into a tissue disposed within a recessed area of the handpiece. The device and method cut the fibrous structures under the skin that cause cellulite at an angle substantially parallel to the surface of the skin and replace these structures with a non-cellulite forming structure by deploying a highly fibrous mesh through a single needle hole to create a highly fibrous layer directly or through wound healing processes.

14 Claims, 31 Drawing Sheets

(56) References Cited

U.S. PATENT DOCUMENTS

| | | |
|---|---|---|
| 4,188,952 A | 2/1980 | Loschilov et al. |
| 4,248,231 A | 2/1981 | Herczog et al. |
| 4,382,441 A | 5/1983 | Svedman |
| 4,497,325 A | 2/1985 | Wedel |
| 4,536,180 A | 8/1985 | Johnson |
| 4,688,570 A | 8/1987 | Kramer et al. |
| 4,796,624 A | 1/1989 | Trott et al. |
| 4,815,462 A | 3/1989 | Clark |
| 4,886,491 A | 12/1989 | Parisi et al. |
| 4,919,986 A | 4/1990 | Lay et al. |
| 4,920,954 A | 5/1990 | Alliger et al. |
| 4,936,281 A | 6/1990 | Stasz |
| 5,022,414 A | 6/1991 | Muller |
| 5,143,063 A | 9/1992 | Fellner |
| 5,149,319 A | 9/1992 | Unger |
| 5,178,433 A | 1/1993 | Wagner |
| 5,203,785 A | 4/1993 | Slater |
| 5,209,720 A | 5/1993 | Unger |
| 5,215,104 A | 6/1993 | Steinert |
| 5,261,922 A | 11/1993 | Hood |
| 5,316,000 A | 5/1994 | Chapelon et al. |
| 5,342,380 A | 8/1994 | Hood |
| 5,354,307 A | 10/1994 | Porowski et al. |
| 5,409,126 A | 4/1995 | Demars |
| 5,417,654 A | 5/1995 | Kelman |
| 5,419,761 A | 5/1995 | Narayanan et al. |
| 5,419,777 A | 5/1995 | Hofling |
| 5,441,490 A | 8/1995 | Svedman |
| 5,476,368 A | 12/1995 | Rabenau et al. |
| 5,507,790 A | 4/1996 | Weiss |
| 5,533,981 A | 7/1996 | Mandro et al. |
| 5,556,406 A | 9/1996 | Gordon et al. |
| 5,562,693 A | 10/1996 | Devlin et al. |
| 5,569,242 A | 10/1996 | Lax et al. |
| 5,571,131 A | 11/1996 | Ek et al. |
| 5,601,584 A | 2/1997 | Obaji et al. |
| 5,649,947 A | 7/1997 | Auerbach et al. |
| 5,662,646 A | 9/1997 | Fumich |
| 5,690,657 A | 11/1997 | Koepnick |
| 5,755,753 A | 5/1998 | Knowlton |
| 5,766,198 A | 6/1998 | Li |
| 5,778,894 A | 7/1998 | Dorogi et al. |
| 5,817,115 A * | 10/1998 | Nigam .................... 606/166 |
| 5,827,216 A | 10/1998 | Igo et al. |
| 5,871,524 A | 2/1999 | Knowlton |
| 5,884,631 A | 3/1999 | Silberg |
| 5,885,232 A | 3/1999 | Guitay |
| 5,902,272 A | 5/1999 | Eggers et al. |
| 5,911,700 A | 6/1999 | Mozsary et al. |
| 5,918,757 A | 7/1999 | Przytulla et al. |
| 5,919,219 A | 7/1999 | Knowlton |
| 5,935,142 A | 8/1999 | Hood |
| 5,935,143 A | 8/1999 | Hood |
| 5,948,011 A | 9/1999 | Knowlton |
| 5,961,475 A | 10/1999 | Guitay |
| 5,976,153 A | 11/1999 | Fischell et al. |
| 5,976,163 A * | 11/1999 | Nigam .................... 606/166 |
| 5,984,915 A | 11/1999 | Loeb et al. |
| 6,047,215 A | 4/2000 | McClure et al. |
| 6,048,337 A | 4/2000 | Svedman |
| 6,083,236 A | 7/2000 | Feingold |
| 6,102,887 A | 8/2000 | Altman |
| 6,113,558 A | 9/2000 | Rosenschein et al. |
| 6,117,152 A | 9/2000 | Huitema |
| 6,139,518 A | 10/2000 | Mozary et al. |
| 6,155,989 A | 12/2000 | Collins |
| 6,176,854 B1 | 1/2001 | Cone |
| 6,193,672 B1 | 2/2001 | Clement |
| 6,200,313 B1 | 3/2001 | Abe et al. |
| 6,203,540 B1 | 3/2001 | Weber |
| 6,241,753 B1 | 6/2001 | Knowlton |
| 6,277,116 B1 | 8/2001 | Uteley et al. |
| 6,280,401 B1 | 8/2001 | Mahurkar |
| 6,302,863 B1 | 10/2001 | Tankovich |
| 6,311,090 B1 | 10/2001 | Knowlton |
| 6,312,439 B1 | 11/2001 | Gordon |
| 6,315,756 B1 | 11/2001 | Tankovich |
| 6,325,801 B1 | 12/2001 | Monnier |
| 6,338,710 B1 | 1/2002 | Takahashi et al. |
| 6,350,276 B1 | 2/2002 | Knowlton |
| 6,366,206 B1 | 4/2002 | Ishikawa et al. |
| 6,375,634 B1 | 4/2002 | Carroll |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,391,020 B1 | 5/2002 | Kurtz et al. |
| 6,391,023 B1 | 5/2002 | Weber et al. |
| 6,397,098 B1 | 5/2002 | Uber, III et al. |
| 6,405,090 B1 | 6/2002 | Knowlton |
| 6,413,255 B1 | 7/2002 | Stern |
| 6,425,912 B1 | 7/2002 | Knowlton |
| 6,430,446 B1 | 8/2002 | Knowlton |
| 6,432,101 B1 | 8/2002 | Weber et al. |
| 6,436,078 B1 | 8/2002 | Svedman |
| 6,438,424 B1 | 8/2002 | Knowlton |
| 6,440,121 B1 | 8/2002 | Weber et al. |
| 6,443,914 B1 | 9/2002 | Costantino |
| 6,453,202 B1 | 9/2002 | Knowlton |
| 6,461,350 B1 | 10/2002 | Underwood et al. |
| 6,461,378 B1 | 10/2002 | Knowlton |
| 6,470,216 B1 | 10/2002 | Knowlton |
| 6,500,141 B1 | 12/2002 | Irion et al. |
| 6,517,498 B1 | 2/2003 | Burbank et al. |
| 6,537,242 B1 | 3/2003 | Palmer |
| 6,544,201 B1 | 4/2003 | Guitay |
| 6,582,442 B2 | 6/2003 | Simon et al. |
| 6,599,305 B1 | 7/2003 | Feingold |
| 6,605,080 B1 | 8/2003 | Altshuler et al. |
| 6,607,498 B2 | 8/2003 | Eschel |
| 6,662,054 B2 | 12/2003 | Kreindel et al. |
| 6,663,616 B1 | 12/2003 | Roth et al. |
| 6,663,618 B2 | 12/2003 | Weber et al. |
| 6,687,537 B2 | 2/2004 | Bernabei |
| 6,695,808 B2 | 2/2004 | Tom |
| 6,725,095 B2 | 4/2004 | Fenn et al. |
| 6,743,211 B1 | 6/2004 | Prausnitz et al. |
| 6,743,215 B2 | 6/2004 | Bernabei |
| 6,749,624 B2 | 6/2004 | Knowlton |
| 6,770,071 B2 | 8/2004 | Woloszko et al. |
| 6,795,728 B2 | 9/2004 | Chornenky et al. |
| 6,826,429 B2 | 11/2004 | Johnson et al. |
| 6,855,133 B2 | 2/2005 | Svedman |
| 6,882,884 B1 | 4/2005 | Mosk et al. |
| 6,892,099 B2 | 5/2005 | Jaafar et al. |
| 6,896,674 B1 | 5/2005 | Woloszko et al. |
| 6,916,328 B2 | 7/2005 | Brett |
| 6,918,908 B2 * | 7/2005 | Bonner et al. .................. 606/41 |
| 6,920,883 B2 | 7/2005 | Bessette et al. |
| 6,926,683 B1 | 8/2005 | Kochman et al. |
| 6,960,205 B2 * | 11/2005 | Jahns et al. .................... 606/41 |
| 6,974,450 B2 | 12/2005 | Weber |
| 6,994,691 B2 | 2/2006 | Ejlersen |
| 6,994,705 B2 | 2/2006 | Nebis et al. |
| 7,066,922 B2 | 6/2006 | Angel et al. |
| 7,083,580 B2 | 8/2006 | Bernabei |
| 7,184,614 B2 | 2/2007 | Slatkine |
| 7,186,252 B2 | 3/2007 | Nobis et al. |
| 7,217,265 B2 | 5/2007 | Hennings et al. |
| 7,226,446 B1 | 6/2007 | Mody et al. |
| 7,252,641 B2 | 8/2007 | Thompson et al. |
| 7,331,951 B2 | 2/2008 | Eschel et al. |
| 7,351,295 B2 | 4/2008 | Pawlik et al. |
| 7,374,551 B2 | 5/2008 | Liang |
| 7,376,460 B2 | 5/2008 | Bernabei |
| 7,442,192 B2 | 10/2008 | Knowlton |
| 7,452,358 B2 | 11/2008 | Stern et al. |
| 7,470,237 B2 | 12/2008 | Beckman et al. |
| 7,473,251 B2 | 1/2009 | Knowlton et al. |
| 7,479,104 B2 | 1/2009 | Lau et al. |
| 7,494,488 B2 | 2/2009 | Weber |
| 7,507,209 B2 | 3/2009 | Nezhat et al. |
| 7,566,318 B2 | 7/2009 | Haefner |

| | | |
|---|---|---|
| 7,585,281 B2 | 9/2009 | Nezhat et al. |
| 7,625,354 B2 | 12/2009 | Hochman |
| 7,625,371 B2 | 12/2009 | Morris et al. |
| 7,901,421 B2 * | 3/2011 | Shiuey et al. ............... 606/166 |
| 2001/0014805 A1 | 8/2001 | Burbank et al. |
| 2002/0029053 A1 | 3/2002 | Gordon |
| 2002/0099356 A1 | 7/2002 | Unger et al. |
| 2002/0130126 A1 | 9/2002 | Rosenberg |
| 2002/0177846 A1 | 11/2002 | Muller |
| 2003/0130628 A1 | 7/2003 | Duffy |
| 2003/0130655 A1 | 7/2003 | Woloszko et al. |
| 2003/0130711 A1 | 7/2003 | Pearson et al. |
| 2003/0139740 A1 | 7/2003 | Kreindel |
| 2003/0171670 A1 | 9/2003 | Gumb et al. |
| 2003/0212350 A1 | 11/2003 | Tadlock |
| 2004/0019371 A1 | 1/2004 | Jaafar et al. |
| 2004/0030263 A1 | 2/2004 | Dubrul et al. |
| 2004/0073144 A1 | 4/2004 | Carava |
| 2004/0073206 A1 | 4/2004 | Foley et al. |
| 2004/0106867 A1 | 6/2004 | Eschel et al. |
| 2004/0120861 A1 | 6/2004 | Petroff |
| 2004/0138712 A1 | 7/2004 | Tamarkin et al. |
| 2004/0162546 A1 | 8/2004 | Liang et al. |
| 2004/0162554 A1 | 8/2004 | Lee et al. |
| 2004/0186425 A1 | 9/2004 | Schneider et al. |
| 2004/0200909 A1 | 10/2004 | McMillan et al. |
| 2004/0210214 A1 | 10/2004 | Knowlton |
| 2004/0220512 A1 | 11/2004 | Kreindel |
| 2004/0236248 A1 | 11/2004 | Svedman |
| 2004/0236252 A1 | 11/2004 | Muzzi et al. |
| 2004/0243159 A1 * | 12/2004 | Shiuey ............... 606/166 |
| 2004/0253148 A1 | 12/2004 | Leaton |
| 2004/0253183 A1 | 12/2004 | Uber, III et al. |
| 2005/0033338 A1 | 2/2005 | Ferree |
| 2005/0049543 A1 | 3/2005 | Anderson et al. |
| 2005/0055018 A1 | 3/2005 | Kreindal |
| 2005/0102009 A1 | 5/2005 | Costantino |
| 2005/0131439 A1 | 6/2005 | Brett |
| 2005/0182462 A1 | 8/2005 | Chornenky et al. |
| 2005/0215987 A1 | 9/2005 | Slatkine |
| 2005/0234527 A1 | 10/2005 | Slatkine |
| 2005/0256536 A1 | 11/2005 | Grundeman et al. |
| 2006/0079921 A1 * | 4/2006 | Nezhat et al. ............... 606/185 |
| 2006/0100555 A1 | 5/2006 | Cagle et al. |
| 2006/0206040 A1 | 9/2006 | Greenberg |
| 2006/0206117 A1 | 9/2006 | Harp |
| 2006/0211958 A1 | 9/2006 | Rosenberg et al. |
| 2006/0241672 A1 | 10/2006 | Zadini et al. |
| 2006/0241673 A1 | 10/2006 | Zadini et al. |
| 2006/0259102 A1 | 11/2006 | Slatkine |
| 2006/0264926 A1 * | 11/2006 | Kochamba ............... 606/41 |
| 2006/0293722 A1 | 12/2006 | Slatkine et al. |
| 2007/0005091 A1 | 1/2007 | Zadini et al. |
| 2007/0027411 A1 | 2/2007 | Ella et al. |
| 2007/0043295 A1 | 2/2007 | Chomas et al. |
| 2007/0055179 A1 | 3/2007 | Deem et al. |
| 2007/0060989 A1 | 3/2007 | Deem et al. |
| 2007/0118077 A1 | 5/2007 | Clarke et al. |
| 2007/0118166 A1 | 5/2007 | Nobis et al. |
| 2007/0129708 A1 | 6/2007 | Edwards et al. |
| 2007/0142881 A1 | 6/2007 | Hennings |
| 2007/0156096 A1 * | 7/2007 | Sonoda et al. ............... 604/174 |
| 2007/0179515 A1 | 8/2007 | Matsutani et al. |
| 2007/0191827 A1 | 8/2007 | Lischinsky |
| 2007/0239075 A1 | 10/2007 | Rosenberg et al. |
| 2007/0270745 A1 * | 11/2007 | Nezhat et al. ............... 604/115 |
| 2007/0282318 A1 | 12/2007 | Spooner et al. |
| 2007/0293849 A1 | 12/2007 | Hennings et al. |
| 2008/0014627 A1 | 1/2008 | Merchant et al. |
| 2008/0015624 A1 * | 1/2008 | Sonoda et al. ............... 606/185 |
| 2008/0058603 A1 | 3/2008 | Edelstein et al. |
| 2008/0058851 A1 | 3/2008 | Edelstein et al. |
| 2008/0091182 A1 | 4/2008 | Mehta |
| 2008/0109023 A1 | 5/2008 | Greer |
| 2008/0147084 A1 | 6/2008 | Bleich et al. |
| 2008/0183164 A1 | 7/2008 | Elkins et al. |
| 2008/0188835 A1 | 8/2008 | Hennings et al. |
| 2008/0234609 A1 | 9/2008 | Kreindel et al. |
| 2008/0249526 A1 | 10/2008 | Knowlton |
| 2008/0262527 A1 | 10/2008 | Eder et al. |
| 2008/0306476 A1 | 12/2008 | Hennings et al. |
| 2009/0012434 A1 | 1/2009 | Anderson |
| 2009/0024192 A1 | 1/2009 | Mulholland |
| 2009/0048544 A1 | 2/2009 | Rybyanets et al. |
| 2009/0088823 A1 | 4/2009 | Barak et al. |
| 2009/0093864 A1 | 4/2009 | Anderson |
| 2009/0125013 A1 | 5/2009 | Sypniewksi et al. |
| 2009/0156958 A1 | 6/2009 | Mehta et al. |
| 2009/0192441 A1 | 7/2009 | Gelbart et al. |
| 2009/0198189 A1 | 8/2009 | Simons et al. |
| 2009/0248004 A1 | 10/2009 | Altshuler et al. |
| 2009/0275879 A1 | 11/2009 | Deem et al. |
| 2009/0275899 A1 | 11/2009 | Deem et al. |
| 2009/0275967 A1 | 11/2009 | Stokes et al. |
| 2010/0022999 A1 | 1/2010 | Gollnick et al. |
| 2010/0057056 A1 | 3/2010 | Gurtner et al. |
| 2010/0137799 A1 * | 6/2010 | Imai ............... 604/115 |
| 2010/0228182 A1 | 9/2010 | Clark, III et al. |
| 2010/0228207 A1 | 9/2010 | Ballakur et al. |
| 2010/0331875 A1 * | 12/2010 | Sonoda et al. ............... 606/185 |

FOREIGN PATENT DOCUMENTS

| | | |
|---|---|---|
| EP | 148116 A1 | 7/1985 |
| EP | 0327490 A1 | 2/1989 |
| GB | 1577551 | 2/1976 |
| WO | 8002365 | 11/1980 |
| WO | 8905159 | 6/1989 |
| WO | 8905160 | 6/1989 |
| WO | 8909593 | 10/1989 |
| WO | 9001971 | 3/1990 |
| WO | 9209238 | 6/1992 |
| WO | 9515118 | 6/1995 |
| WO | 03/047689 A1 | 6/2003 |
| WO | 03047689 A1 | 6/2003 |
| WO | 2004000116 A1 | 12/2003 |
| WO | 2004069153 A2 | 8/2004 |
| WO | 2007102161 A2 | 9/2007 |
| WO | 2008139303 A2 | 11/2008 |

OTHER PUBLICATIONS

Bindal, Dr. V.V. et al., Environmental Health Criteria for Ultrasound International Programs on Chemical Safety, 1982, pp. 1-153, World Health Organization.

Brown, Ph.D, S., Director of Plastic Surgery Research, UT Southwestern Medical Center, Dallas, USA, What Happens After Treatment With the UltraShape Device, UltraShape Ltd., Tel Aviv, Israel.

Cartensen, E.L., Allerton Conference for Ultrasonics in Biophysics and Bioengineering: Cavitation, Ultrasound in Med. & Biol., 1987, pp. 687-688, vol. 13, Pergamon Journals, Ltd.

Chang, Peter P. et al., Thresholds for Inertial Cavitation in Albunex Suspensions Under Pulsed Ultrasound Conditions, IEEE Transactions on Ultrasonics, Ferroelectrics, and Frequency Control, Jan. 2001, p. 161-170, vol. 48, No. 1.

Chen, Wen-Shiang, Ultrasound Contrast Agent Behavior near the Fragmentation Threshold, 2000 IEEE Ultrasonics Symposium, 2000, pp. 1935-1938.

Dijkmans, P.A., et al., Microbubbles and Ultrasound: From Diagnosis to Therapy, Eur J Echocardiography, 2004, pp. 245-256, vol. 5, Elsevier Ltd., The Netherlands.

Feril, L.B., et al., Enhanced Ultrasound-Induced Apoptosis and Cell Lysis by a Hypnotic Medium, International Journal of Radiation Biology, Feb. 2004, pp. 165-175, vol. 2, Taylor & Francis Ltd., United Kingdom.

Feril, Jr., Loreto B., et al., Biological Effects of Low Intensity Ultrasound: The Mechanism Involved, and its Implications on Therapy and on Biosafety of Ultrasound, J. Radiat. Res., 2004, pp. 479-489, vol. 45.

Forsberg, Ph.D., F., et al., On the Usefulness of the Mechanical Index Displayed on Clinical Ultrasound Scanners for Predicting Contrast Microbubble Destruction, J Ultrasound Med, 2005, pp. 443-450, vol. 24, American Institute of Ultrasound in Medicine.

Hanscom, D.R., Infringement Search Report prepared for K. Angela Macfarlane, Esq., Chief Technology Counsel, The Foundry, Nov. 15, 2005.

Hexsel, M.D., Doris Maria, et al., Subcision: a Treatment for Cellulite, International journal of Dermatology 2000, pp. 539-544, vol. 39.

Holland, Christy K., et al., In Vitro Detection of Cavitation Induced by a Diagnostic Ultrasound System, IEEE Transactions on Ultrasonics, Ferroelectrics, and Frequency Control, Jan. 1992, pp. 95-101, vol. 39, No. 1.

Lawrence, M.D., N., et al., The Efficacy of External Ultrasound-Assisted Liposuction: A Randomized Controlled Trial, Dermatol Surg, Apr. 2000, pp. 329-332, vol. 26, Blackwell Science, Inc.

Michaelson, Solomon M., et al., Fundamental and Applied Aspects of Nonionizing Radiation, Rochester International Conference on Environmental Toxicity, 75h, 1974, pp. 275-299, Plenum Press, New York and London.

Miller, Douglas L., A Review of the Ultrasonic Bioeffects of Microsonation, Gas-Body Activiation, andRelated Cavitation-Like Phenomena, Ultrasound in Med. & Biol., 1987, pp. 443-470, vol. 13, Pergamon Journals Ltd.

Miller, Douglas L., et al., Further Investigations of ATP Release From Human Erythrocytes Exposed to Ultrasonically Activated Gas-Filled Pores, Ultrasound in Med. & Biol., 1983, pp. 297-307, vol. 9, No. 3, Pergamon Press Ltd., Great Britain.

Miller, Douglas L., Gas Body Activation, Ultrasonics, Nov. 1984, pp. 261-269, vol. 22, No. 6, Butterworth & Co. Ltd.

Miller, Douglas L., Microstreaming Shear as a Mechanism of Cell Death in Elodea Leaves Exposed to Ultrasound, Ultrasound in Med. & Biol., 1985, pp. 285-292, vol. 11, No. 2, Pergamon Press, U.S.A.

Miller, Douglas L., et al., On the Oscillation Mode of Gas-filled Micropores, J. Acoust. Soc. Am., 1985, pp. 946-953, vol. 77 (3).

Miller, Morton W., et al., A Review of In Vitro Bioeffects of Inertial Ultrasonic Cavitation From a Mechanistic Perspective, Ultrasound in Med. & Biol., 1996, pp. 1131-1154, vol. 22, No. 9.

Nyborg, Dr. Wesley L., Physical Mechanisms for Biological Effects of Ultrasound, HEW Publicaton (FDA) 78-8062, Sep. 1977, pp. 1-59, U.S. Department of Health, Education, and Welfare, Rockville, Maryland.

Rohrich, M.D., R.J., et al., Comparative Lipoplasty Analysis of in Vivo-Treated Adipose Tissue, Plastic and Reconstructive Surgery, May 2000, pp. 2152-2158, vol. 105, No. 6.

Scheinfeld, M.D., J.D. Faad, N.S., Liposuction Techniques: External Ultrasound-Assisted, eMedicine.com, Inc., 2005.

Villarraga, M.D., H.R., et al., Destruction of Contrast Microbubbles During Ultrasound Imaging at Conventional Power Output, Journal of the American Society of Echocardiography, Oct. 1997, pp. 783-791.

Vivino, Alfred A., et al., Stable Cavitation at low Ultrasonic Intensities Induces Cell Death and Inhibits 3H-TdR Incorporation by Con-A-Stimulated Murine Lymphocytes In Vitro, Ultrasound in Med. & Biol., 1985, pp. 751-759, vol. 11, No. 5, Pergamon Press Ltd.

Internet Web Site—www.icin.nl/read/project_21, The Interuniversity Cardiology Institute of the Netherlands, 3 pgs., visited Dec. 22, 2005.

Internet Web Site—www.turnwoodinternational.com/Cellulite.htm, Acthyderm Treating Cellulite, Aug. 5, 2005, 4 pgs., visited Jan. 12, 2006.

Letters to the Editor re on the Thermal Motions of Small Bubbles, Ultrasound in Med. & Biol., 1984, pp. L377-L379, Pergamon Press Ltd., U.S.A.

Patent Search, CTX System Microbubble Cavitation, Nov. 11, 2005.

Report, Carstensen, E.L., Biological Effects of Acoustic Cavitation, University of Rochester, Rochester, New York, May 13-16, 1985.

Weaver, James C. Electroporation; a general phenomenon for manipulating cells and tissues. J Cell Biochem. Apr. 1993; 51(4):426-35.

Sasaki, Gordon H. MD, Comparison of Results of Wire Subcision Peformed Alone, With Fills, and/or With Adjacent Surgical Procedures, Aesthetic Surgery Journal, vol. 28, No. 6, Nov./Dec. 2008, p. 619-626.

Hexel, D. et al, Side-By-Side Comparison of Areas with and without Cellulite Depressions Using Magnetic Resonance Imaging, American Society for Dermatologic Surgery, Inc., 2009, pp. 1-7, Wiley Periodicals, Inc.

Khan, M. et al., Treatment of cellulite-Part I. Pathophysiology, J Am Acad Dermatol, 2009, vol. 62, No. 3, pp. 361-370.

Khan, M. et al., Treatment of cellulite-Part II. Advances and controversies, J Am Acad Dermatol, 2009, vol. 62, No. 3, pp. 373-384.

Boyer, J. et al., Undermining in Cutaneous Surgery, Dermatol Surg 27:1, Jan. 2001, pp. 75-78, Blackwell Science, Inc.

Orentreich, D. et al., Subcutaneous Incisionless (Subcision) Surgery for the Correction of Depressed Scars and Wrinkles, Dermatol Surg, 1996:21, 1995, pp. 543-549, Elsevier Science Inc.

International Search Report dated Apr. 9, 2012 from corresponding International Patent Application No. PCT/US11/62449.

* cited by examiner

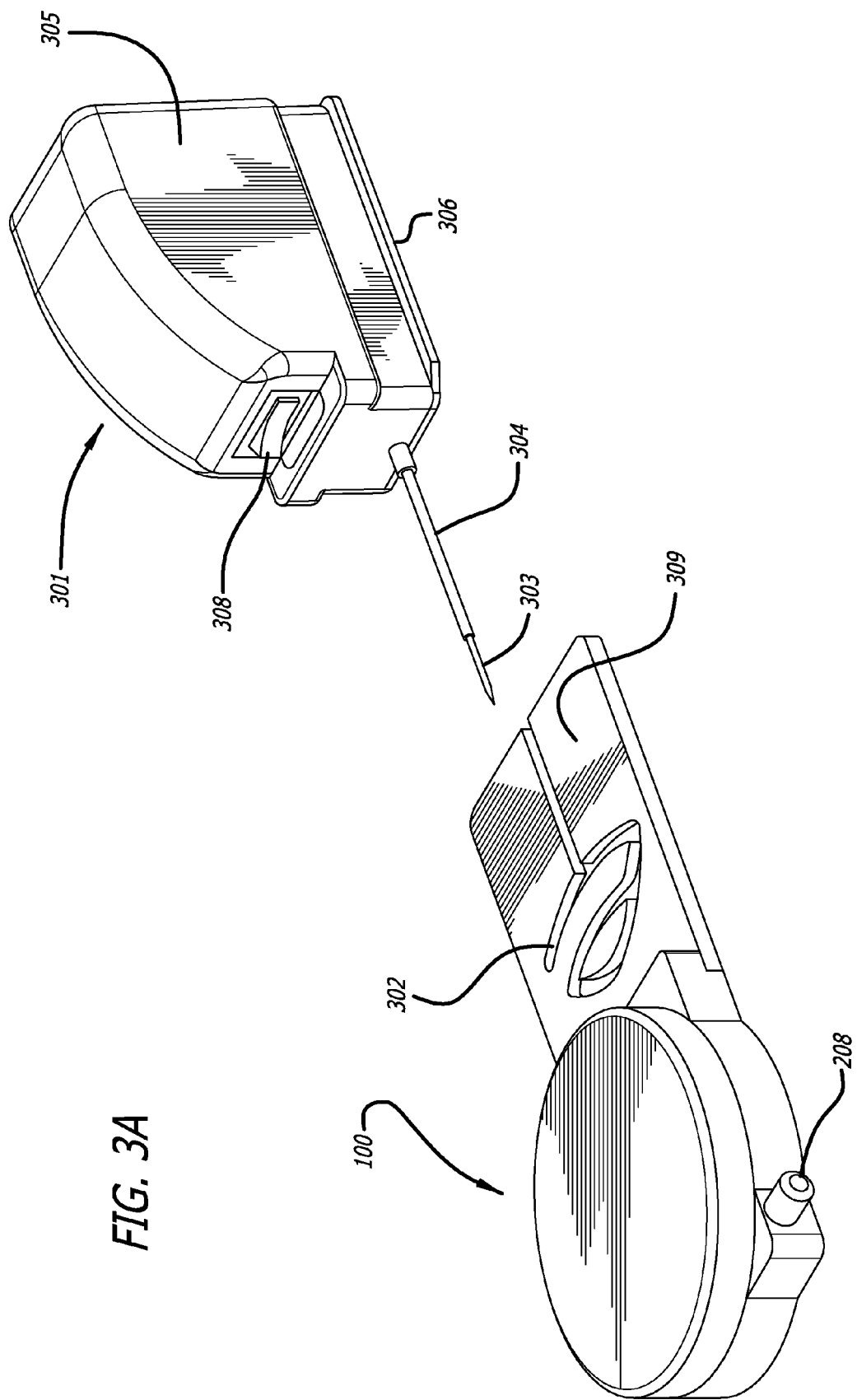

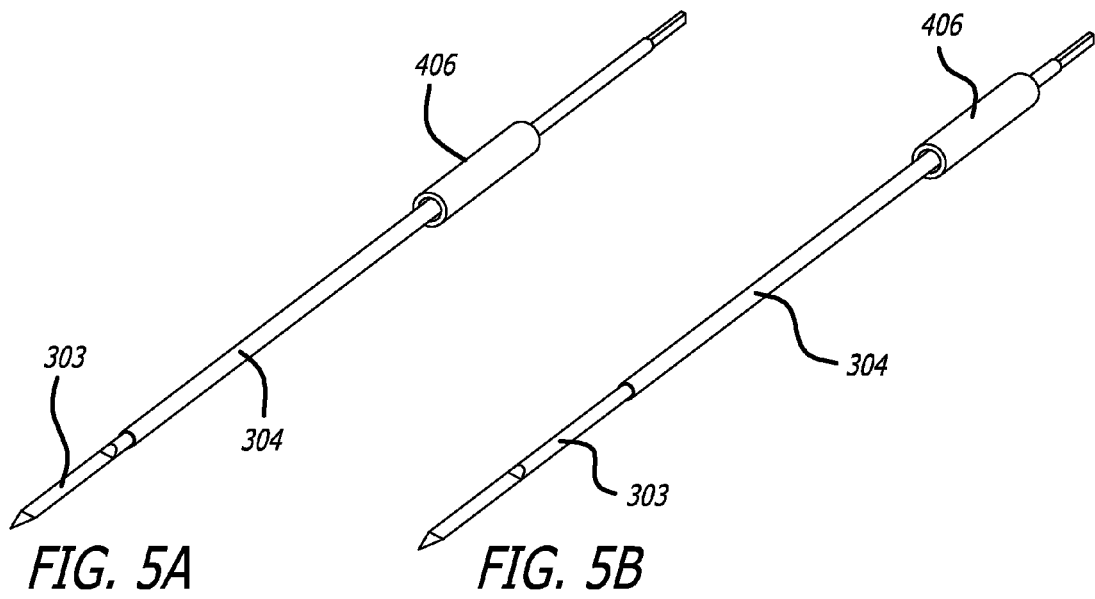
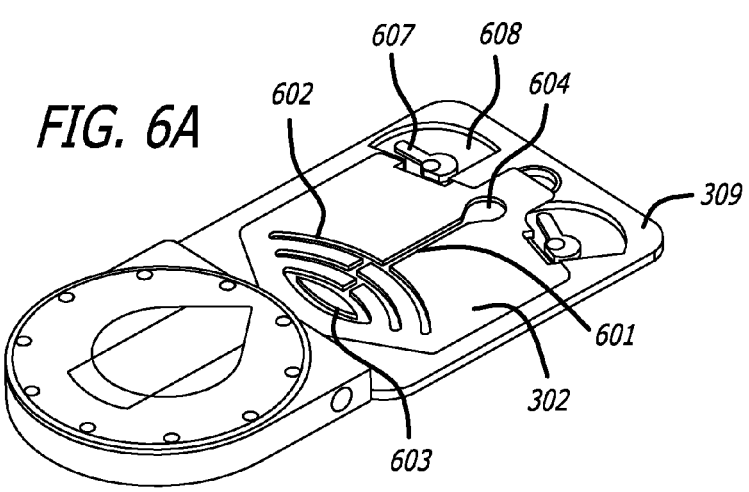

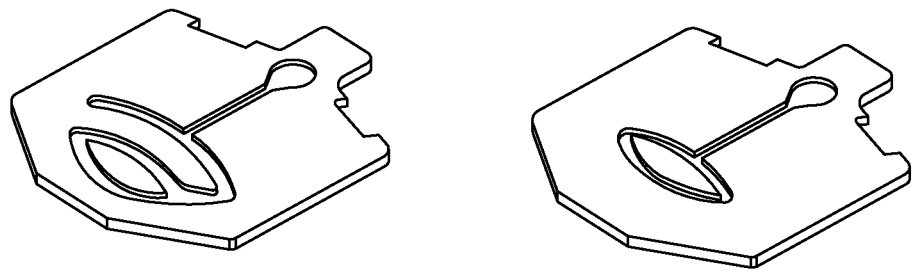
FIG. 6B
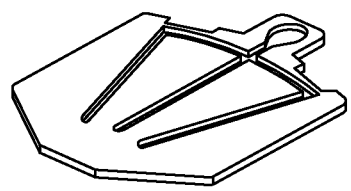
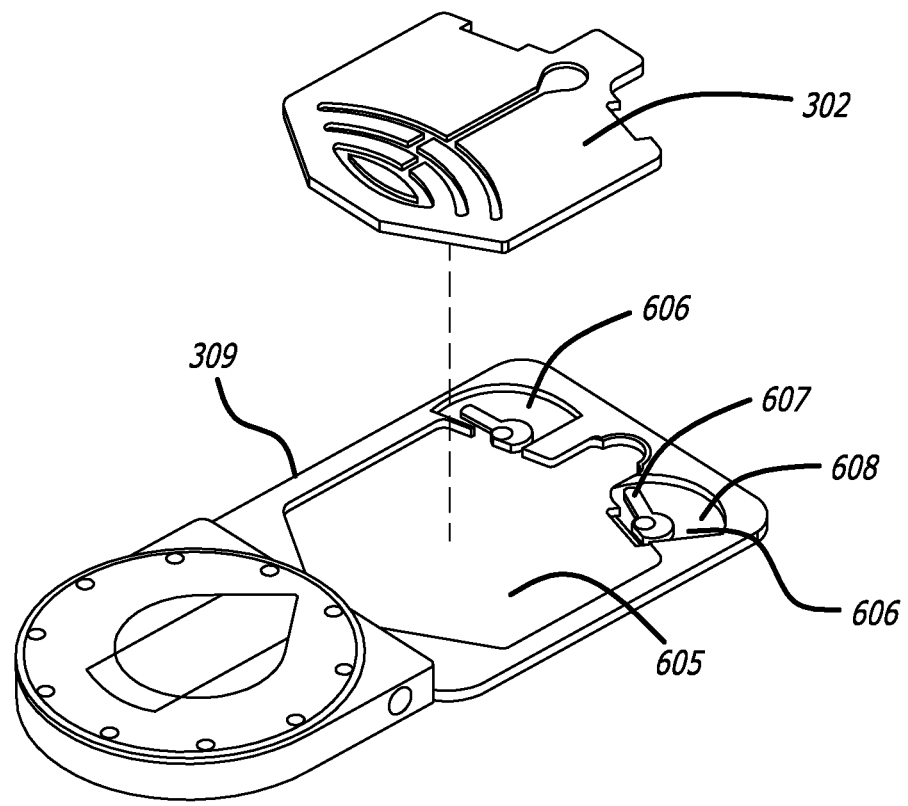

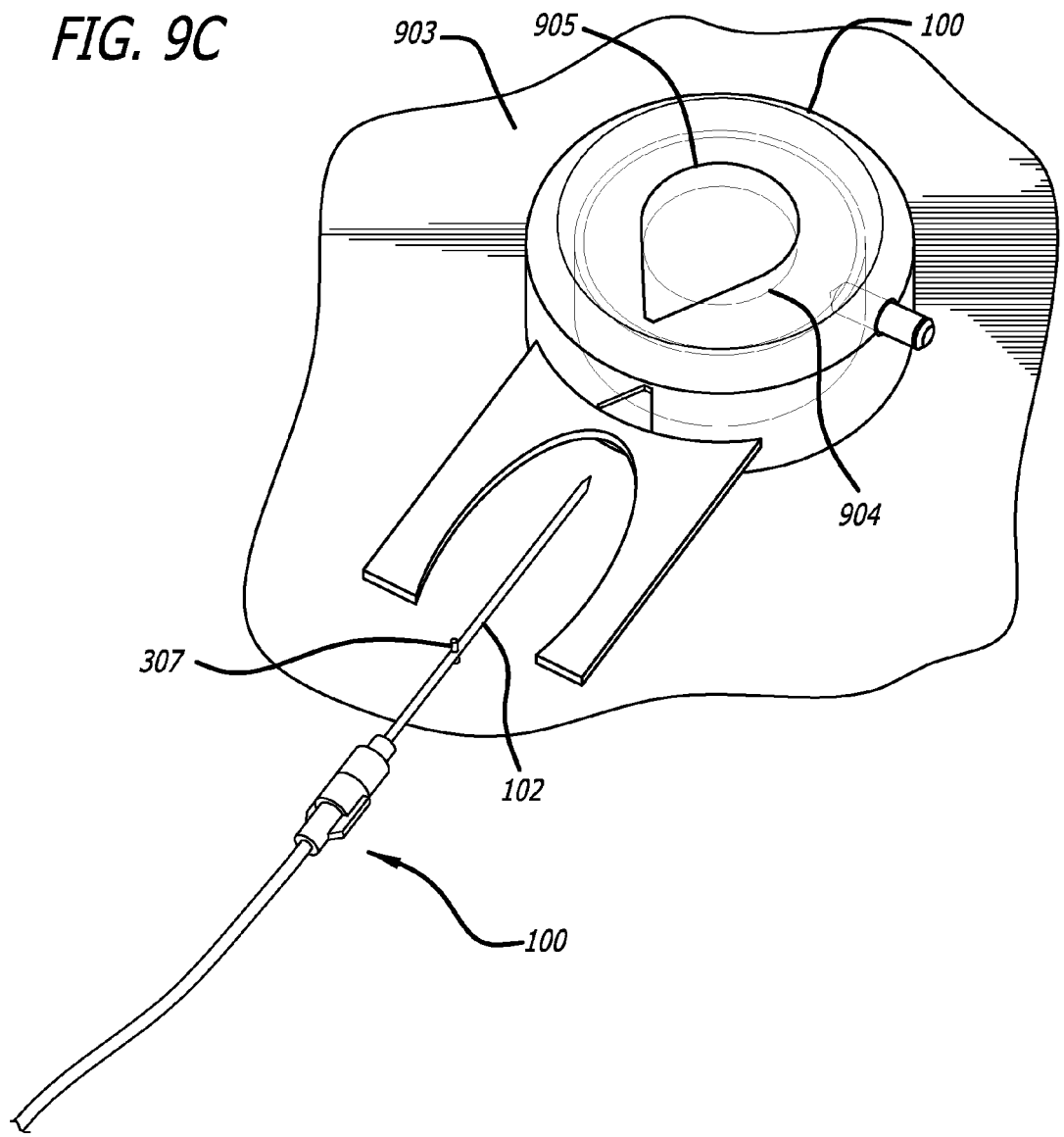

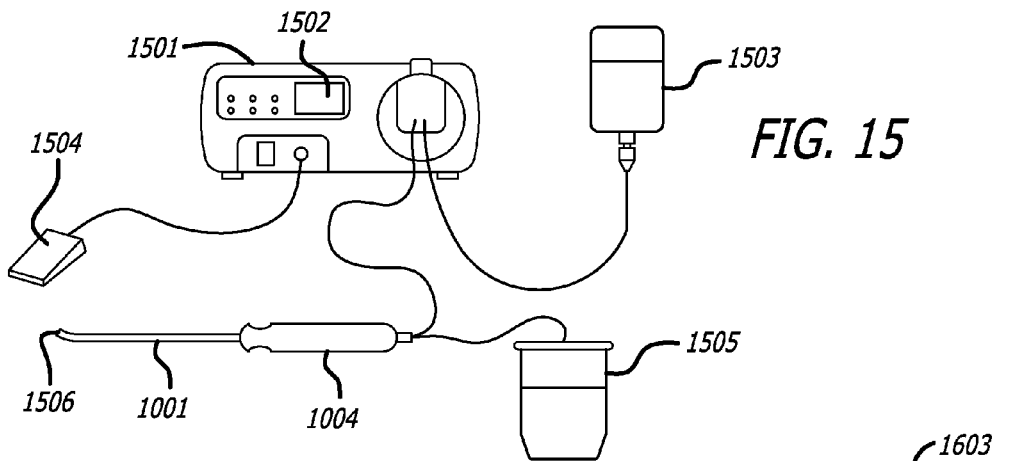
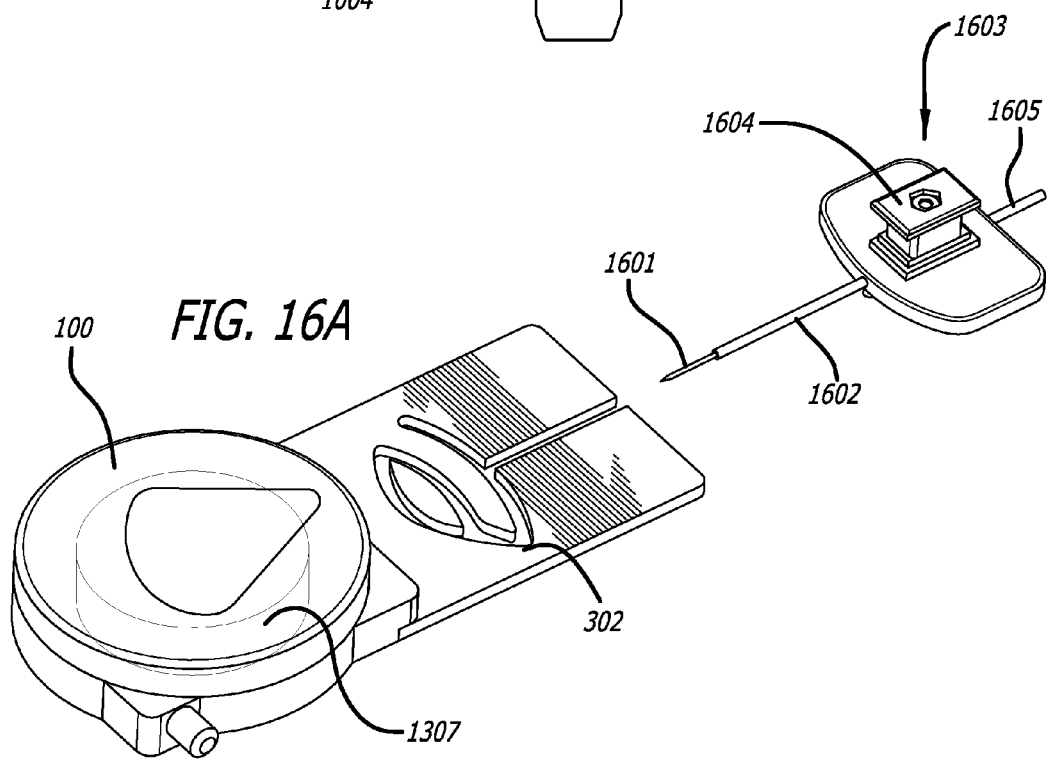
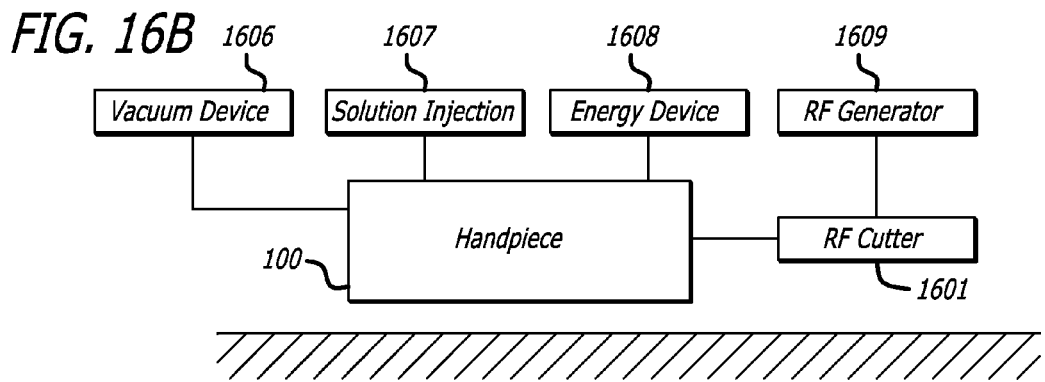

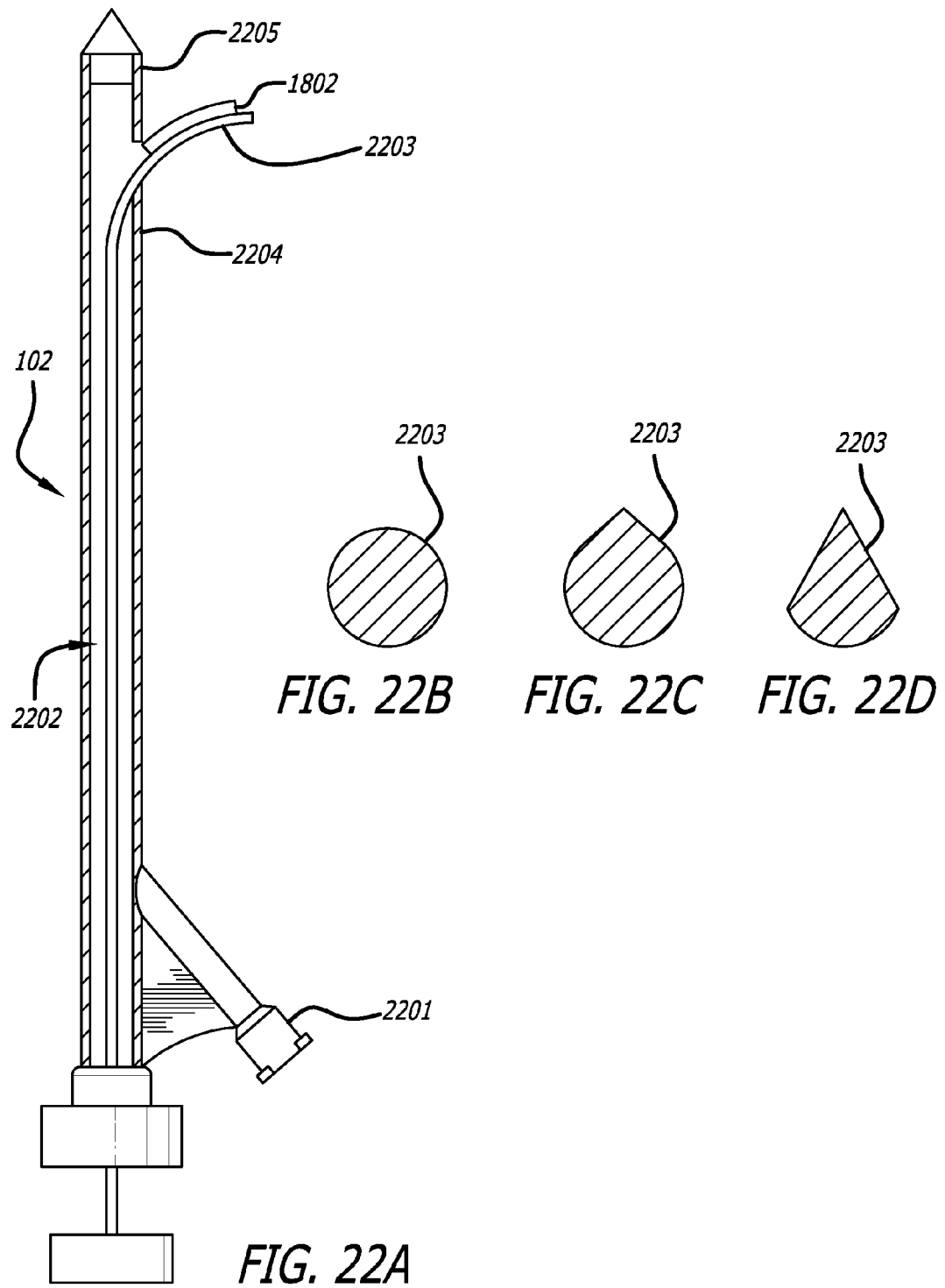

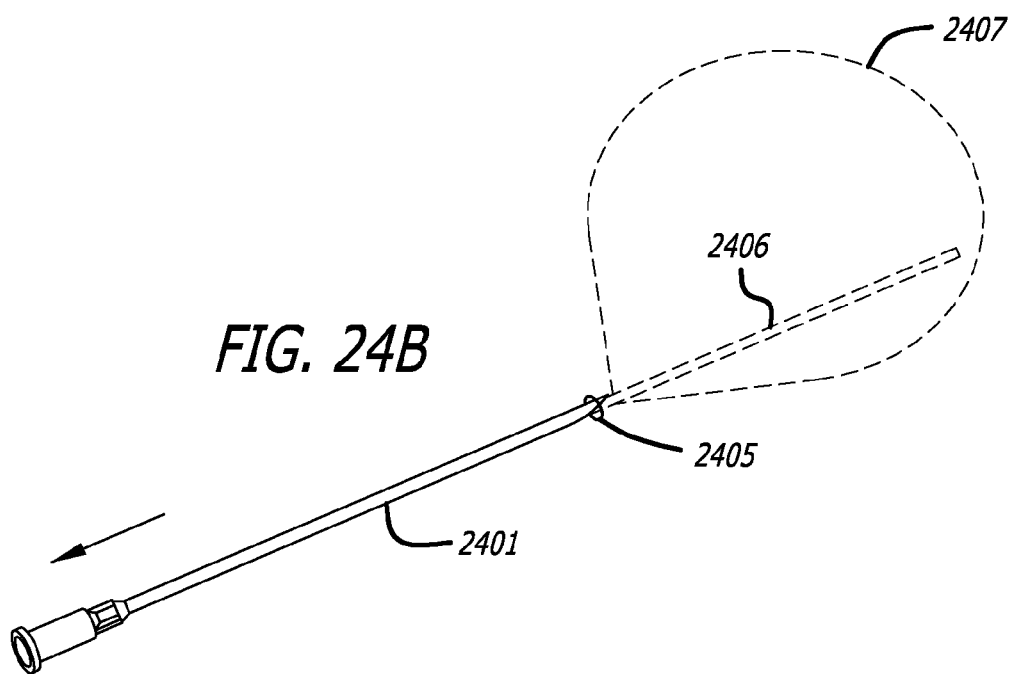
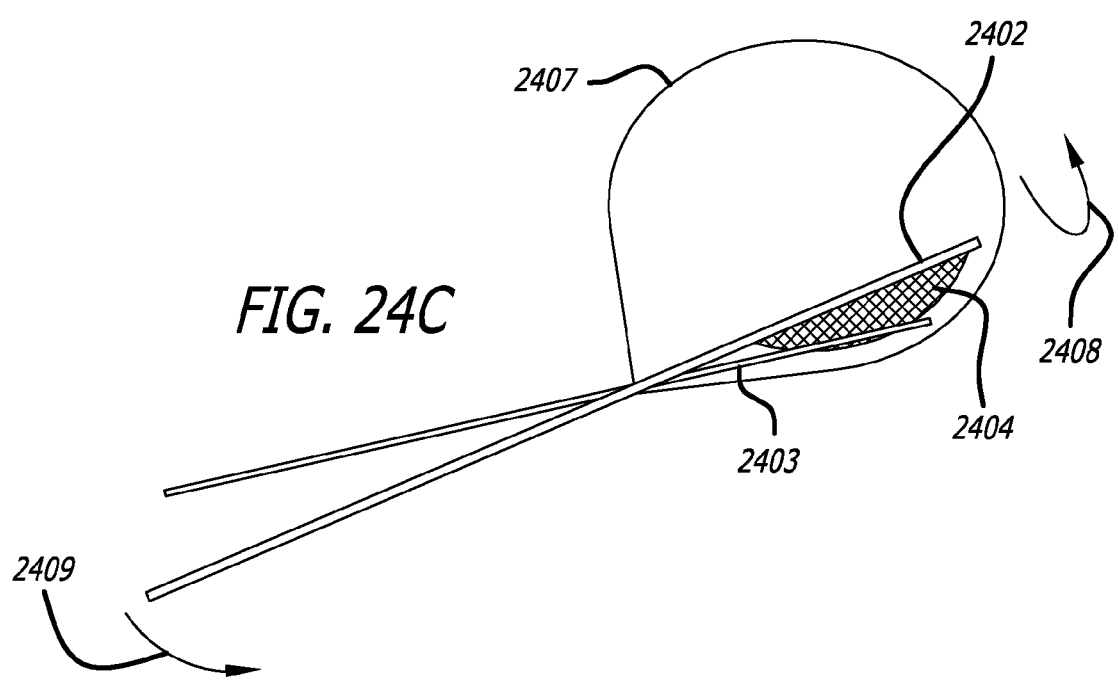

DISSECTION HANDPIECE AND METHOD FOR REDUCING THE APPEARANCE OF CELLULITE

CROSS-REFERENCES TO RELATED APPLICATIONS

This application is a continuation-in-part and claims priority from U.S. application Ser. No. 12/555,746, filed Sep. 8, 2009, which is a continuation-in-part and claims priority from U.S. application Ser. No. 11/515,634, filed Sep. 5, 2006, and U.S. application Ser. No. 11/334,794, filed Jan. 17, 2006 (now U.S. Pat. No. 7,588,547), both of which claim priority to U.S. Provisional Application No. 60/715,398, filed Sep. 7, 2005, and, all of which are incorporated by reference in their entirety. This application also is a continuation-in-part and claims priority from U.S. application Ser. No. 12/247,853, filed Oct. 8, 2008, which claims priority to U.S. Provisional Application No. 60/978,607, Oct. 9, 2007, both of which are incorporated by reference. Applicants claim priority to all of the applications in the chain.

This application also claims priority from U.S. Provisional Application No. 61/232,385, filed Aug. 7, 2009, and U.S. Provisional Application No. 61/286,750, Dec. 15, 2009, both of which are incorporated by reference in their entirety.

FIELD OF THE INVENTION

The present invention relates to surgical tools and implantable devices which modify subdermal structures for decreasing the appearance of cellulite.

BACKGROUND

Most aesthetic issues for which patients seek treatment from physicians today are "more than skin deep." For instance, gynoid lipodystrophy is a localized disorder of the subcutaneous tissue which leads to an alteration in the topography of the cutaneous surface (skin), or a dimpling effect. It is thought to be caused by increased fluid retention and/or proliferation of adipose tissue in certain subdermal regions, but known to be structure related. This condition, commonly known as cellulite, affects over 90% of post-pubescent women, and some men. Cellulite commonly appears on the hips, buttocks and legs, but is not necessarily caused by being overweight, as is a common perception. Cellulite is formed in the subcutaneous level of tissue, in the subdermal fat layer below the epidermis and dermis layers. In this region, fat cells are arranged in chambers surrounded by bands of connective tissue called septae. Cellulite is in part due to the parallel orientation of these fibrous septae structures. The fibrous structures being oriented in a parallel fashion (and perpendicular to the skin) is unique to women, whereas men typically have more random orientation of fibrous structures. This difference in fibrous structure may be in part or wholly responsible for the fact that men do not exhibit widespread cellulite in comparison to women. As the fat cells held within the perimeters defined by these fibrous septae expand they stretch the septae and surrounding connective tissue. Furthermore, adipocyte expansion from weight gain may also stretch the septae. Eventually this connective tissue contracts and hardens (scleroses) holding the skin at a non-flexible length, while the chambers between the septae continue to expand with weight gain, or water gain. This results in areas of the skin being held down while other sections bulge outward, resulting in the lumpy, 'orange peel' or 'cottage cheese' appearance on the skin surface. Even though obesity is not considered to be a root cause of cellulite, it can certainly worsen the dimpled appearance of a cellulitic region due to the increased number of fat cells in the region.

Over the years, a variety of approaches for treatment of skin irregularities such as cellulite and removal of unwanted adipose tissue have been proposed. For example, methods and devices that provide mechanical massage to the affected area, through either a combination of suction and massage or suction, massage and application of energy, in addition to application of various topical agents are currently available. Developed in the 1950's, mesotherapy is an injection of various treatment solutions through the skin that has been widely used in Europe for conditions ranging from sports injuries to chronic pain, to cosmetic procedures to treat wrinkles and cellulite. This treatment consists of the injection or transfer of various agents through the skin to provide increased circulation and the potential for fat oxidation, such as aminophylline, hyaluronic acid, Novocain, plant extracts, and other vitamins. Another treatment entitled Acthyderm (Turnwood International, Ontario, Canada) employs a roller system that electroporates the stratum corneum to open small channels in the dermis, followed by the application of various mesotherapy agents, such as vitamins, antifibrotics, lypolitics, anti-inflammatories and the like.

Various other approaches employing dermatologic creams, lotions, vitamins, and herbal supplements have also been proposed to treat cellulite. Private spas and salons offer cellulite massage treatments that include body scrubs, pressure point massage, essential oils, and herbal products using extracts from plant species such as seaweed, horsetail and clematis and ivy have also been proposed. Although a multitude of therapies exist, most of them do not provide a lasting effect on the skin irregularity, and some therapies may even cause the worsening of cellulite in certain patients. Yet other treatments for cellulite have negative side effects that limit their adoption. Regardless, most of these therapies require multiple treatments on an ongoing basis to maintain their effect at significant expense and with mixed results.

Massage techniques were tried as early as the 1930's as a method to increase lymphatic drainage and improve the appearance of cellulite. Mechanical massage devices, or Pressotherapy, have also been developed such as the "Endermologie" device (LPG Systems, France), the "Synergie" device (Dynatronics, Salt Lake City, Utah) and the "Silklight" device (Lumenis, Tel Aviv, Israel), all utilizing subdermal massage via vacuum and mechanical rollers. Other approaches have included a variety of energy sources, such as Cynosure's "TriActive" device (Cynosure, Westford, Mass.) utilizing a pulsed semiconductor laser in addition to mechanical massage, and the "Cellulux" device (Palomar Medical, Burlington, Mass.) which emits infrared light through a cooled chiller to target subcutaneous adipose tissue. The "VelaSmooth" system (Syneron, Inc., Yokneam Illit, Israel) employs bipolar radiofrequency energy in conjunction with suction massage to increase metabolism in adipose tissue, and the "Thermacool" device (Thermage, Inc., Hayward, Calif.) utilizes radio frequency energy to shrink the subdermal fibrous septae to treat wrinkles and other skin defects. Other energy-based therapies such as electrolipophoresis, using several pairs of needles to apply a low frequency interstitial electromagnetic field to aid circulatory drainage have also been developed. Similarly, non-invasive ultrasound is used in the "Dermosonic" device (Symedex Medical, Minneapolis, Minn.) to promote increased fat reabsorption and drainage of retained fluids and toxins.

Methods and devices using ultrasound to disrupt subcutaneous tissues directly has been described in the known art.

Such techniques may utilize a high intensity ultrasound wave that is focused on a tissue within the body, thereby causing a localized destruction or injury to cells. The focusing of the high intensity ultrasound may be achieved utilizing, for example, a concave transducer or am acoustic lens. Use of high intensity focused ultrasound to disrupt fat, sometimes in combination with removal of the fat by liposuction, has been described in the known prior art. Such use of high intensity focused ultrasound is distinguished from low acoustic pressure, therapeutic ultrasound.

Recently, it is has also become possible to exploit ultrasound waves for the purpose of disrupting tissue and tissue ablation without heating tissue to a level of tissue disruption. One such device is disclosed in U.S. Publication No. 2007/0055179 to Deem et al., incorporated herein by reference, which includes a method of infiltrating exogenous microbubbles into the target tissue, followed by applying low acoustic pressure ultrasound to the infiltrated tissue to cavitate the bubbles and destroy the target tissue without direct thermal injury to the dermis. Although low acoustic pressure ultrasound may somewhat heat tissue, the tissue is not heated sufficiently to cause direct tissue disruption or to enhance the ablation, and thus significantly reduces the risk of thermal damage to the dermis and associated structures (nerves, hair follicles, blood vessels). Liposonix (Bothell, Wash.) and Ultrashape (Tel Aviv, Israel) employ the use of focused ultrasound to destroy adipose tissue noninvasively. In addition, cryogenic cooling has been proposed for destroying adipose tissue.

Certain other techniques known as liposuction, tumescent liposuction, lypolysis and the like, target adipose tissue in the subdermal and deep fat regions of the body. These techniques may include also removing the fat cells once they are disrupted, or leaving them to be resorbed by the body's immune/lymphatic system. Liposuction is the most commonly performed cosmetic surgical procedure. Traditional liposuction includes the use of a surgical cannula placed at the site of the fat to be removed, and then the use of an infusion of fluids and mechanical motion of the cannula to break up the fatty tissue, and suction to "vacuum" the disrupted fatty tissue directly out of the patient. A variation on the traditional liposuction technique known as tumescent liposuction was introduced in 1985 and is currently considered by some to be the standard of care in the United States. It involves the infusion of tumescent fluids to the targeted region prior to mechanical disruption and removal by the suction cannula. The fluids may help to ease the pain of the mechanical disruption in some patients, while also swelling the tissues to make them more susceptible to mechanical removal. Various combinations of fluids may be employed in the tumescent solution including a local anesthetic such as lidocaine, a vasoconstrictive agent such as epinephrine, saline, potassium and the like. The benefits of such an approach are detailed in the articles, "Laboratory and Histopathologic Comparative Study of Internal Ultrasound-Assisted Lipoplasty and Tumescent Lipoplasty" Plastic and Reconstructive Surgery, Sep. 15, (2002) 110:4, 11581164, and "When One Liter Does Not Equal 1000 Milliliters: Implications for the Tumescent Technique" Dermatol. Surg. (2000) 26:1024-1028, the contents of which are expressly incorporated herein by reference in their entirety.

Traditional fat extraction techniques such as liposuction, target deep fat and larger regions of the anatomy and can sometimes worsen the appearance of cellulite. The subdermal fat pockets remain and are accentuated by the loss of underlying bulk (deep fat) in the region. Many times liposuction is performed and patients still seek therapy for remaining skin irregularities, such as cellulite. The tools used in these procedures often have cutting edges and are intended to dissect the subcutaneous tissue and fibrous sepatae. Representative of such conventional tools is the "Toledo" cannula, pictured in Toledo L S, Mauas R, Complications of Body Sculpture: Prevention and Treatment. Clin Plastic Surg. 2006:33; 1-11.

There are physicians who target the more shallow subdermal fat pockets with liposuction, but at a higher risk of directly creating surface irregularities rather than treating them. Liposuction is not considered a viable treatment for cellulite for these reasons.

Another issue that must be factored in with liposuction is the amount of drugs infused with the tumescent solution. With large volume liposuctions, the Lidocaine infusion (for pain) can get up as high as 50 mg/kg, well above the intravascular toxicity limit of 7 mg/kg. The reason why liposuction patients can tolerate such a large volume of lidocaine is that the lidocaine is injected subcutaneously, is highly diluted, and is absorbed slowly over time. Thus, the actual systemic level of lidocaine is lower. However, in some cases lidocaine can spill over into the circulation and has resulted in patient mortality. For this reason, physicians monitor the Lidocaine does closely and often limit the area or treatment as a result.

More recently, energy sources have been added to the cannula to assist in the break-up and liquefication of the fat which in turn improves the ease of use. The "Lysonix" system (Mentor Corporation, Santa Barbara, Calif.) and "Vaser" system (Sound Surgical, Louisville, Colo.) utilize an ultrasonic transducer within the suction cannula to assist in tissue disruption (by cavitation of the tissue at the targeted site). Laser assisted cannula are offered by several companies including "Smartlipo" (Cynosure, Westford, Mass.), "Slimlipo" (Palomar Medical, Burlington, Mass.), and "Smoothlipo"(Eleme Medical, Merrimack, N.H.).

Subcutaneous dissection without fat aspiration is another approach to the treatment of skin irregularities such as scarring and dimpling. A technique called "subcision" was described by Orentreich in 1995. See Orentreich D S, Orentreich N. Subcutaneous incisionless surgery for the correction of depressed scars and wrinkles Dermatological Surgery 1995 June; 21 (6): 543-9. This technique involves the insertion of a relatively large gauge needle subdermally in the region of dimpling or scarring, and then mechanically manipulating the needle below the skin to break up the fibrous septae in the subdermal region. In at least one known method of subcision, a solution containing an anesthetic (Lidocaine) and vasoconstrictor is injected into the targeted region and allowed to take effect. An 18-gauge needle is then inserted 10-20 mm below the cutaneous surface. The needle is then pulled back and directed parallel to the epidermis to create a dissection plane beneath the skin to essentially tear through, or "free up" the tightened septae causing the dimpling or scarring. Pressure is then applied to control bleeding acutely, and then by the use of compressive clothing following the procedure. While clinically effective in some patients, pain, bruising, bleeding and scarring can result. Other cutting implements include the aforementioned Toledo cannula, and several string or wire based cutting methods including the "Surgiwire" (Coapt Systems, Palo Alto, Calif.) and "ReleaseWire" (MicroAire, Charlottesville, Va.).

Cutting or relieving of the fibrous septae in the subdermal region by current subcision methods, is labor intensive, time consuming and techniques are highly variable. Significant physician time must be devoted to the procedure and there are technical limits as well as anesthetic limits to the size of a treatable area. There is a lack of clinical proof of that the techniques work for most patients and that the effects are lasting. For these reasons, and because of the potential side effects and extended time required for healing, subcision and liposuction have largely been abandoned as a treatment for cellulite in the United States.

In light of the foregoing, it would be desirable to provide methods and apparatus for treating skin irregularities such as cellulite and to provide a sustained aesthetic result to a body region, such as the face, neck, arms, legs, thighs, buttocks, breasts, stomach and other targeted regions. It would also be desirable to provide methods and apparatus for treating skin irregularities that enhance prior techniques and make them less time intensive, more controlled, minimally invasive, and subject the patient to fewer side effects. The present invention adds a minimally invasive device and method for skin treatment by providing a controlled and less traumatic means for subcutaneous dissection and cutting of the fibrous septae in the subdermal fat or in the layer between the subdermal fat layers and the dermis, responsible for the appearance of cellulite, as well as a controlled means of anesthetic delivery. Further enhancement of lasting effect is provided by insertion of fibrous mesh through a single needle hole to create a highly fibrous layer directly or through the wound healing processes. The device and method also provides an even level of cutting, parallel to the surface of the skin and with adequate skin traction, without further puncture or cutting of the skin. In addition to treating cellulite, this device and method may be used to treat hyperhidrosis, acne or other scars, and wrinkles This treatment may also be used in conjunction with known methods of removing fat, skin tightening, or dermal thickening.

SUMMARY OF THE INVENTION

A minimally invasive skin treatment device is disclosed. The device comprises a handpiece having a perimeter elevation and a top which cooperatively define a recessed area with an inner side of the perimeter elevation and the top defining an apposition surface facing into the recessed area; a conduit extending through a side of the perimeter elevation to the recessed area; a tool configured to at least partially extend through the conduit and into the recessed area; and a guidance track operably connected to the handpiece, wherein the guidance track is configured to constrain a portion of the tool in contact with the guidance track to move along a predetermined path to cooperatively move a distal end of the tool within the recessed area in a plane substantially parallel to the top of the handpiece and within a region of a predetermined shape defined by the predefined path.

In some aspects, the device further comprises an entry hole disposed on an inner side of the conduit and facing said recessed area, said entry hole defining a tool pivot point when a distal end of the tool is inserted through the conduit and into the recessed area, wherein the conduit widens outward toward an outer side of the perimeter elevation such that a distal end of the tool inserted through the entry hole moves in one direction when a proximal end of the tool outside the conduit moves in an opposite direction.

In some aspects, the device may also comprise a platform operatively connected to the handpiece, wherein the platform includes the guidance track; and a guide pin operably connected to the tool, said guide pin slidably engaging the guidance track such that the tool is constrained to move in accordance with the predetermined path. In some aspects, the platform can be fixed with respect to the handpiece and substantially orthogonal to a bottom edge of the handpiece. The guidance track may form a groove in a top of the platform, or, in some aspects, the guidance track is a contour formed from an edge of the platform. The guidance track may include an undercut portion and the guide pin can have an enlarged head such that the interference between the enlarge head and the undercut portion of the guidance track inhibits removal of the enlarged head from the guidance track while permitting the guide pin to be moved in accordance with the predetermined path.

In some aspects, the tool comprises a cutting blade and a reciprocating motor coupled to the cutting blade, said reciprocating motor reciprocating the cutting blade. The tool may further include a sleeve, wherein the cutting blade is at least partially slidably disposed within the sleeve. The tool may also include an injection device and a nozzle, wherein the nozzle is configured to discharge a fluid in a direction parallel to the top of the handpiece and configured to increase a kinetic energy of the fluid when the fluid is injected by the injection device through the nozzle.

In further aspects, the top of the handpiece is configured to be adjustable and configured to change the distance between an inner side of the top of the handpiece and a bottom edge of the perimeter elevation and changes a volume of the recessed area when the top is adjusted. In some aspects, the handpiece includes a reversible lid, and, the top of the handpiece being configured to be adjustable includes the reversible lid being configured to be disconnected from the handpiece, turned over, and reconnected. In certain aspects, the top of the handpiece includes a rigid upper lid and a rigid lower lid, the rigid upper lid being fixed with respect to the perimeter elevation, the device further including an inflatable bladder disposed between the rigid upper lid and rigid lower lid, wherein the rigid lower lid is configured to move up and down with respect to a wall of the perimeter elevation, the rigid inner lid being at its lowest point when the bladder is fully expanded, and being at its highest point when the bladder is deflated. In other aspects, the top of the handpiece is operably connected to a perimeter wall of the perimeter elevation by a threaded engagement, the top of the handpiece being rotatably mounted to the perimeter wall, and wherein rotation of the top relative to the perimeter wall adjusts the volume of the recessed area. The top of the handpiece may also include an upper rim disposed between an upper edge of an outer wall and an upper edge of inner wall, a recessed surface disposed at a bottom edge of the inner wall, a perimeter of the recessed surface being substantially defined by a bottom edge of the inner wall, and a first and second reference mark, the first reference mark being spaced a rotational distance from the second reference mark such that the rotational distance corresponds to predetermined vertical distance along the threaded engagement. An o-ring may be interposed between the top of the handpiece and the perimeter wall of the handpiece.

The device may also be configured to include an elastomeric septum, the elastomeric septum being configured to be pierced by the tool and to substantially self-seal when the tool is removed such as to substantially prevent a vacuum leakage from the recessed area when a vacuum is supplied to the recessed area. Other aspects may include the device comprising a support arm having a guide pin, the tool being mounted to the support arm, wherein the guidance track operably connected to the handpiece includes the guidance track being disposed on a surface of the top of the handpiece and slidably receiving the guide pin, the guidance track facilitating movement of the pin and support arm along the predetermined path.

In a yet further aspect, the tool is an elongate RF cutting probe. In this aspect, the device may further include an RF generator operably connected to and supplying a power to the RF cutting probe, and a circuit for measuring the impedance of a tissue disposed within the recessed area, wherein the RF generator includes a feedback control on the power supplied to the probe based on a measured impedance of the tissue such that the RF generator supplies a consistent power. In certain aspects, a temperature means on the RF cutting probe is also included. The temperature measuring means is used to communicate information indicative of a temperature of the tissue to the RF generator, wherein the feedback control stops supplying power to the RF cutting probe when a temperature of the tissue reaches a predefined threshold.

Some aspects of the device may include a vacuum fitting operably connected to one of the top and the perimeter elevation and in fluid communication with the recessed area. These aspects may also include a vacuum pump in fluid communication with the vacuum fitting, wherein the vacuum pump is configured to supply a suction force to the recessed area and configured to pull a tissue snugly and securely against the apposition surface when the recessed area is placed over the tissue.

It may also be desirable is some aspects to use the device to inject a solution. In some aspects, the tool may be a needle, and the device may further include a pump and a source of injectable fluids in fluid communication with the pump, wherein the needle is in fluid communication with the pump, and the needle is configured to inject the injectable fluids into a tissue disposed in the recessed area. In certain aspects, the needle may include a lumen, a tip for piercing a dermis, and at least two injection ports in communication with the lumen, wherein the ports are linearly disposed along an outer surface of the needle. In some aspects, the ports may be flush with a side of the needle. The ports may be configured to discharge a fluid in a direction substantially orthogonal to an axis of the needle and substantially parallel to the top of the handpiece. Some aspects of the foregoing may further include a microprocessor having a graphical user interface, wherein the pump is configured to communicate information specifying a volume of a fluid injected into the tissue to the microprocessor. The microprocessor can be configured to use the graphical user interface to prompt a user to enter information specifying at least one of a concentration of a component of the fluid and a weight of the patient, and the microprocessor can include logic for determining a maximum dosage of the fluid injected based on the weight of the patient, the concentration of the component of the fluid, and the volume of the fluid injected. In some aspects, the microprocessor is configured to cause the graphical interface to display at least one warning message when the volume of the fluid injected exceeds a predefined threshold which is less than the maximum dosage, and may also be configured to instruct the pump to terminate an injection when the volume of the fluid injected reaches the maximum dosage. In further aspects, the graphical user interface may be configured to enable the user to over-ride the maximum dosage such that the pump continues to inject the fluid once the maximum dosage has been reached. In yet further aspects, the microprocessor may be configured to track an amount of elapsed time since the pump initiated pumping the fluid and to calculate a recommended treatment end time using information selected from a group consisting of the volume of fluid injected and the elapsed time. In certain aspects including a vacuum pump, the vacuum pump may be configured to communicate with the microprocessor and the graphical user interface to display an elapsed amount of time a vacuum was supplied to the handpiece by the vacuum pump. The vacuum pump may also be, in some aspects, configured to communicate with the microprocessor and the graphical user interface to display a vacuum pressure. It is not necessary that these aspects regarding injection of a solution and microprocessor control be limited a device wherein the tool is a needle, but it may also be desirable to include these aspects and/or limitations in any of the aspects herein described.

Also disclosed is a method of treating cellulite, the method comprising the steps of (1) providing a handpiece having a perimeter elevation and a top which cooperatively define a recessed area, an inner side of the perimeter elevation and top defining a tissue apposition surface facing into the recessed area, and a conduit extending through a side of the perimeter elevation into the recessed area; (2) positioning the handpiece over a first treatment area located on a dermis; (3) applying a force to the handpiece to move a portion of the dermis into the recessed area to substantially fill the recessed area, such that a portion of the dermis is in contact with a substantial area of the tissue apposition surface and a subcutaneous tissue is disposed in the recessed area; (4) inserting a distal end of a tool through the conduit and through the dermis and into the subcutaneous tissue; and, (4) guiding the tool along a predetermined path of a guidance track to move a distal end of the tool in a plane parallel to the top of the handpiece and within the recessed area, to create a surgical lesion of a predetermined shape defined by the predefined path.

In certain aspects, the method may also include moving the distal end of the tool in an x and y direction along the plane parallel to the top of the handpiece. Certain aspects may also include providing a vacuum assisted suction force to the recessed area to move the dermis into the recessed area.

The method may include adjusting a height of the top of the handpiece in relation to an entry point of the conduit within the recessed area to adjust the volume of the recessed area and a depth of the subcutaneous tissue accessible by the tool when inserted through the conduit. In some aspects, the top includes a reversible lid, and the height is adjusted by disconnecting the reversible lid from the handpiece, turning it over, and reconnecting it to the handpiece. Some aspects of adjusting a height of the top of the handpiece may include rotating the top of the handpiece with respect to the perimeter elevation along a threaded engagement between the top of the handpiece and the perimeter elevation of the handpiece. In other aspects, the top of the handpiece may include a rigid upper lid and a rigid lower lid, the rigid upper lid being fixed with respect to the perimeter elevation, wherein adjusting a height of the top of the handpiece includes inflating a bladder disposed between the rigid upper lid and rigid lower lid to move the rigid lower lid up and down with respect to a wall of the perimeter elevation, the rigid inner lid being at its lowest point when the bladder is fully expanded and being at its highest point when the bladder is deflated.

Some aspects of the method may include the further steps of (a) removing the distal end of the cutting device from the subcutaneous tissue; (b) positioning the handpiece over a second treatment area located on the dermis, wherein the second treatment area is proximal the first treatment area; (c) applying a force to the handpiece to move a portion of the second treatment area of the dermis into the recessed area to substantially fill the recessed area, such that a portion of the second treatment area of the dermis is in contact with a substantial area of the tissue apposition surface and a second layer of subcutaneous tissue is disposed in the recessed area; (d) inserting a distal end of a tool through the conduit and through the dermis and into the second layer of subcutaneous tissue; and (e) guiding the tool along the predetermined path of the guidance track to move the distal end of the tool in the plane parallel to the top of the handpiece and within the recessed area, to create a second surgical lesion of the predetermined shape defined by the guidance track. In some aspects, the second treatment area may also at least partially overlap the first treatment area, and/or adjusting a height of the top of the handpiece in relation to an entry point of the conduit within the recessed area to change the volume of the recessed area and a depth of the subcutaneous tissue accessible by the tool.

In some aspects of the method, the tool is an elongated RF probe, and creating a surgical legion includes applying one of a RF energy or a heat to ablate a portion of the subcutaneous tissue. In further aspects, the portion of the subcutaneous tissue may include adipose tissue, or, include a fibrous septae and creating a surgical legion includes cutting the fibrous septae. In some aspects, the tool is a catheter having a high-pressure fluid jet, and wherein the method of creating a surgical legion includes injecting a fluid at a high pressure and parallel to the top of the handpiece to displace a portion of the subcutaneous tissue.

In yet further aspects of the invention, it may be desirable to deploy a mesh within the subcutaneous tissue or other treatment area. Thus, the method may include the further steps of (a) inserting a distal end of a shaft and a keeper rod through the conduit and into the surgical lesion, the shaft and keeper rod having a mesh furled around the distal end of the shaft and the keeper rod; (b) simultaneously rotating the shaft about its longitudinal axis while anchoring an edge of the mesh with the keeper rod and moving the distal end of the shaft away from the distal end of the keeper rod by pivoting the shaft about an entry point of the conduit to unfurl the mesh in the surgical lesion; and (c) withdrawing the shaft and the keeper rod from the surgical lesion and the recessed area.

In some aspects, a method of treating cellulite by deploying a mesh is disclosed. In this aspect, the method includes the steps of (1) providing a handpiece having a perimeter elevation and a top which cooperatively define a recessed area, an inner side of the perimeter elevation and top defining a tissue apposition surface facing into the recessed area, and a conduit extending through a side of the perimeter elevation into the recessed area; (2) positioning the handpiece over a first treatment area located on a dermis; (3) applying a force to the handpiece to move a portion of the dermis into the recessed area to substantially fill the recessed area, such that the portion of the dermis is in contact with a substantial area of the tissue apposition surface and a subcutaneous tissue is disposed in the recessed area; (4) inserting a cutting tool through the conduit to create a subdermal treatment area defined by a surgical lesion of a predetermined shape in the subcutaneous tissue, and inserting a mesh through the conduit and into the subdermal treatment area. In further aspects, inserting the mesh may include (5) inserting a distal end of a shaft and a keeper rod through the conduit and into a treatment area in the subcutaneous tissue and substantially parallel to the dermis, the shaft and keeper rod having a mesh furled around the distal end of the shaft and the keeper rod; (6) simultaneously rotating the shaft about its longitudinal axis while anchoring an edge of the mesh with the keeper rod and moving the distal end of the shaft away from the distal end of the keeper rod by pivoting the shaft about an entry point of the conduit to unfurl the mesh; and, (7) withdrawing the shaft and the keeper rod from the treatment area.

In at least one aspect of this method, a first end of the mesh is removably secured to the shaft through a first longitudinal slit in the distal end of the shaft, and a second end of the mesh is removably secured to the keeper rod through a second longitudinal slit in the distal end of the keeper rod, wherein withdrawing the shaft and the keeper rod from the open treatment area includes the mesh slipping off the first and second longitudinal slits. In some aspects, the method may further include securing the mesh within the open treatment area by suturing an end of the mesh to a portion of the subcutaneous tissue.

In further aspects, a method of treating cellulite by repositioning a dissection handpiece is disclosed. In some aspects, this method includes (1) positioning a handpiece having a recessed area over a first section of dermis; (2) applying a force to the handpiece to move a portion of the first section of dermis into the recessed area to substantially fill the recessed area, such that a portion of the first section of dermis is in contact with an inner surface of the handpiece and a first subcutaneous tissue is disposed in the recessed area; (3) inserting a tool through a conduit of the handpiece and through the first section of dermis and into the first subcutaneous tissue; and (4) cutting a first lesion in the first subcutaneous tissue at a first depth. In certain aspects of this method, it may be also desirable to include the further step of adjusting a cutting depth of the handpiece.

In some aspects this method may further include repositioning the handpiece over a second section of dermis, wherein the second section of dermis, applying a force to the handpiece to move a portion of the second section of dermis into the recessed area to substantially fill the recessed area, such that a portion of the second section of dermis is in contact with the inner surface of the handpiece and a second subcutaneous tissue is disposed in the recessed area, and cutting a second lesion in the second subcutaneous tissue at a second depth. In some aspects, the first and the second depths are substantially the same depth. In other aspects, the handpiece is adjusted such that the second depth is a different depth than the first depth. In one aspect, adjusting the depth may include applying a different force to move the portion of the second dermis into the recessed area than the force used to move the portion of the first section of dermis into the recessed area. In another aspect, adjusting the depth may include rotating a top of the handpiece along a threaded engagement. In a further aspect, the depth is adjusted by disconnecting a reversible lid from the handpiece, turning it over, and reconnecting it to the handpiece. In yet a further aspect, adjusting a cutting depth may include altering an atmospheric pressure inside the handpiece to move an inner surface at a top of the recessed area in a vertical direction relative to the handpiece.

BRIEF DESCRIPTION OF THE DRAWINGS

FIGS. 3A and 3B depicts a perspective view of the handpiece and motor controlled cutting mechanism;

FIGS. 5A and 5B depict an enlarged view of an embodiment the cutting tool used in connection with the motor controlled cutting mechanism;

FIGS. 6A and 6B depict the handpiece used in connection with a removable guidance track;

FIGS. 9A through 9C depict configuration and placement of the handpiece on a dermis of a patient and an alternate embodiment of the guidance track;

FIG. 15 depicts a microprocessor and display for use with the embodiments;

FIG. 16A depicts an embodiment of the cutting device, including an RF cutter;

FIG. 16B depicts a block diagram of system, including the handpiece and RF cutting tool;

FIGS. 22A through 22D depict another embodiment of the cutting tool;

DETAILED DESCRIPTION OF THE PREFERRED EMBODIMENTS

Figure 1A:
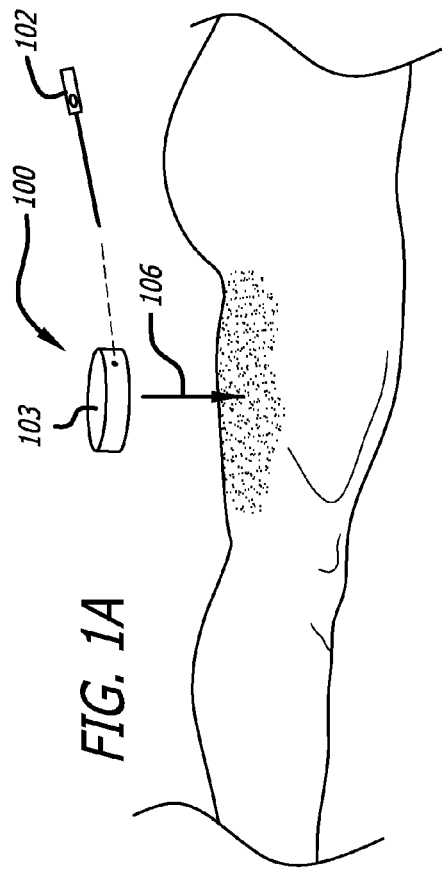
FIGS. 1A through 1C depict a dissection device, including a handpiece and a cutting tool.

As described herein, cellulite is due in part to the parallel orientation of fibrous structures in the subdermal fat layer. In general, the device and method described here is used to minimally invasively cut fibrous septae. One objective is to create a minimally invasive planar dissection at a defined depth below the dermis. In particular, the plane of dissection is created parallel to and at a predefined depth below the dermis. Throughout this application reference to a depth below the dermis or the like should be understood to refer to a depth measured orthogonally from the exterior surface of the skin. It should also be noted that the utility of the devices disclosed extends beyond treatment of cellulite. The device and method may, for example, be useful in treating acne scars by creating a very localized dissection releasing the dermis from the underlying connective tissue. If desired, a suitable filler may be injected into the dissection.

According to some embodiments it may be desirable to implant a mesh of fiber promoting material such as proteins, actin, collagen, or the like into the planar dissection. In the context of cellulite, it may be desirable to make a planar dissection within the shallow fat layer (3-15 mm below the dermis), at the fat/skin interface, or within the deeper fat layer 16-30 mm below the dermis to cut the fibrous septae and disrupt the chambers of fat cells. The introduction of a mesh implant into the situs of the planar dissection (subcision) may counteract the predominantly parallel structures of the fibrous septae in women and create a highly fibrous layer directly or through wound healing processes. This treatment may be used in conjunction with known methods of removing fat, skin tightening, or dermal thickening.

The devices and methods disclosed herein may also be used in a variety of applications where it is necessary to create a pocket in tissue for receiving an implant. Thus, a minimally invasively pocket may be created in the cheek, breast, or buttocks for receiving the implant.

The device and method is also applicable to the treatment of hyperhidrosis. Notably, a planar surgical lesion may be created within the lower level of the dermis or at the interface between the dermis and the shallow fat layer. This surgical lesion severs or damages the eccrine duct from the eccrine sweat gland and/or destroys the eccrine sweat gland.

According to some embodiments it may also be desirable to employ energy such as Radiofrequency (hereinafter "RF"), to provide the dissection means. The energy can be configured to provide coagulation or a controlled thermal injury, which in turn may provide fat cell damage/shrinkage or create a more fibrous layer directly or through wound healing processes. Thermal energy may enhance the effect of the treatment. For instance in the case of hyperhidrosis, thermal injury may increase the number of eccrine glands damaged in the procedure. This treatment may be used in conjunction with known methods of removing fat, skin tightening, or dermal thickening.

According to some embodiments it may be desirable to provide a controlled means of anesthesia delivery to the treatment area prior to the cutting mechanism.

It should be understood the term "may" as used throughout the specification refers to an optional feature or component.

Figure 1B:
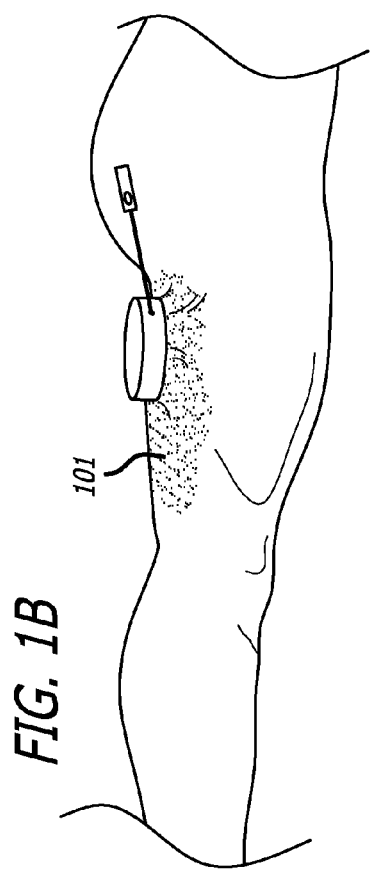
Figure 1C:
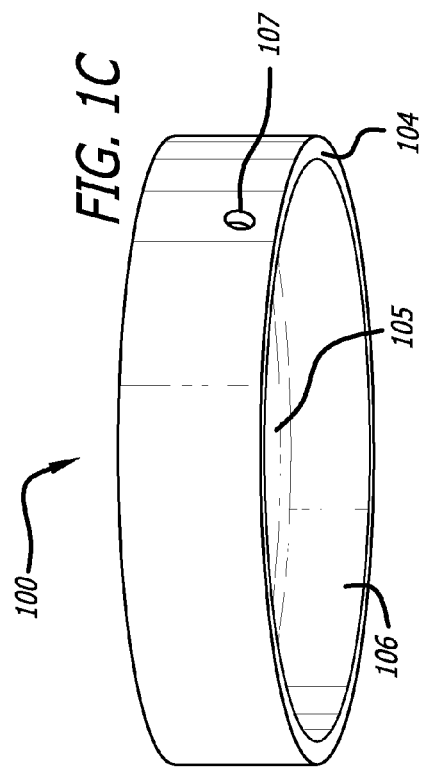

As illustrated by FIGS. 1A through 1C, the embodiments utilize a handpiece 100 to capture and control a location of the skin, or dermis 101, as well as precisely control use of a cutting tool 102. The handpiece preferably has a top 103 and a perimeter elevation 104 that cooperatively define a recessed area 105 which can be placed over the dermis of a patient. By applying a force 106 to the top of the handpiece or by a vacuum supplied to the handpiece, a portion of the dermis 101 can be moved into the recessed area to substantially fill the recessed area, thus capturing it within the handpiece and providing some control over the area of tissue captured. This allows a distal portion of cutting tool 102 or other suitable dissection device to be inserted through a conduit 107 extending through a side of the perimeter elevation of the handpiece, percutaneously through the tissue disposed in the recessed area, and into the subcutaneous tissues encompassed by the recessed area of the handpiece. Cutting tool 102 is maneuvered in such a way as to cut a surgical lesion of a predetermined shape inside the subcutaneous tissues within the recessed area and parallel to the top of the handpiece. The surgical lesion (dissection) is targeted to be in a range from as shallow as at 1 mm to 2 mm below the interface between the dermis and the shallow fat, to as deep as 20 mm below the skin/fat interface. Applicants hereby define percutaneous to mean a puncture or incision through the skin of between 0.4 mm and 4.0 mm. It should be understood that handpiece 100 may be used in conjunction with any of the dissection devices disclosed herein.

Figure 2A:
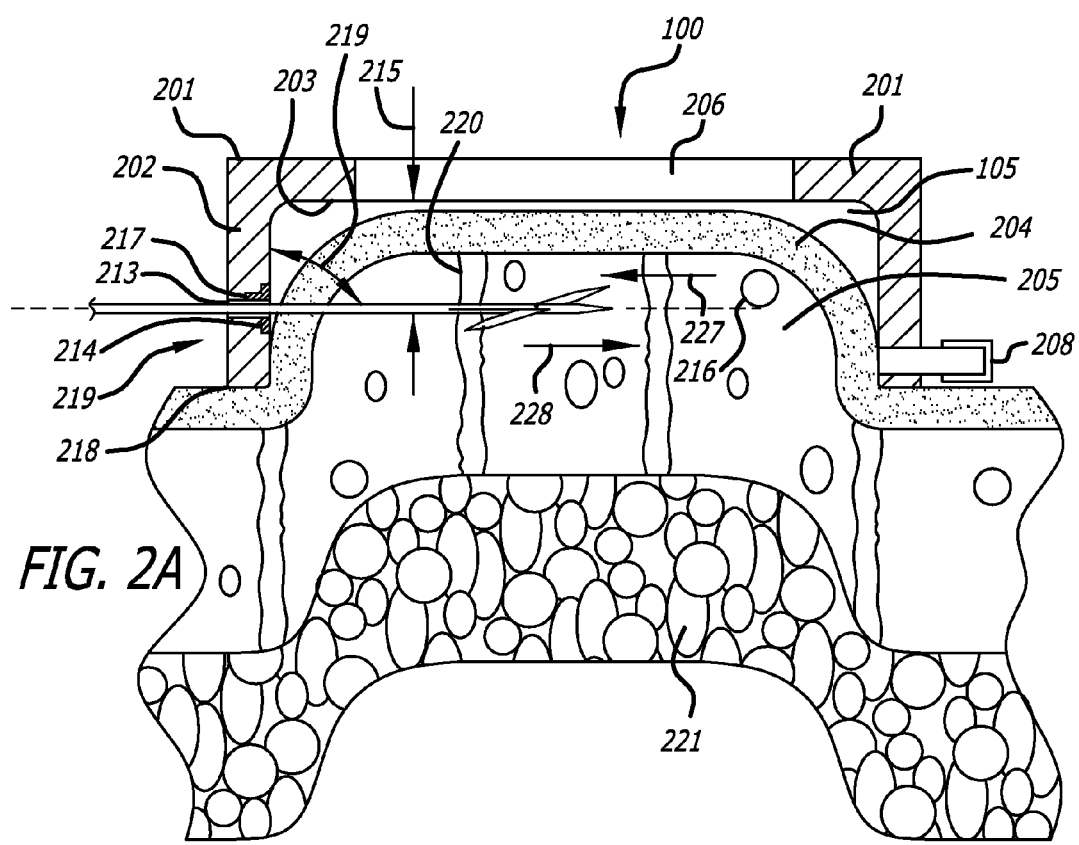
FIGS. 2A and 2B depict a cut-away side view and perspective view of the handpiece used in conjunction with a cutting tool.

Turning to FIG. 2A, a top wall 201 and perimeter wall 202 define a tissue apposition surface (tissue facing surface) 203 facing into recessed area 105. Tissue apposition surface 203 may be curved inward to the handpiece, or concave, or recessed, so that when handpiece 100 is disposed against an epidermis 204, further pressure against the handpiece 100 will cause the handpiece to encompass a subcutaneous level of tissue 205, particularly the subdermal fat layer below the epidermis and dermis layers, wherein these layers will be positioned within recessed area 105. In some embodiments tissue apposition surface 203 includes perimeter wall 202 as a relatively small inner wall around the perimeter of recessed area 105. In some embodiments, handpiece 100 may include a transparent cover 206 so that a physician can clearly see and verify that the dermis is properly positioned within the dissection region. In the depicted embodiments, the perimeter walls (sidewalls) of the handpiece are shown generally circular. However, one of ordinary skill in the art will appreciate that the handpiece can be any shape.

The device further allows for three-dimensional control of treatment or anesthetic solution delivery and dissection of subcutaneous tissues, not realized by present art. The device typically controls a depth 215 of between 4 mm and 20 mm below the surface of skin (measured orthogonally from the dermis); but a depth less than 4 mm or greater than 20 mm is also contemplated. Depth 215 is generally defined as being measured from tissue apposition surface 203. For the purpose of this disclosure, however, the measurement is taken when epidermis 204 is flush against apposition surface 203 and the thickness of epidermis is considered negligible. As such, depth 215 can also be considered to be a depth below the surface of the skin or a depth below epidermis 204. The range of motion in the lateral direction is controlled by the length and movement of the cutting blade and/or RF probe, however, typically encompasses a length of between 2 mm and 100 mm in either direction. As the needle/blade/probe is disposed further into the skin larger arcs are achieved.

Generally, device 100 is pressed against the tissue to move the subcutaneous layer 205 into recessed area 105 and against tissue apposition surface 203. In some embodiments, vacuum (suction) is used to enhance the capture of the tissue. A vacuum source 1606 (FIG. 16B) may be placed in fluid connection with handpiece 100 via an optional vacuum port 208 on handpiece 100. The vacuum source may include a vacuum pump in fluid communication with recessed area 105. Vacuum pump 1606 supplies suction to the recessed area to pull tissue snugly and securely therein. In some embodiments, the vacuum pump is configured to communicate with a microprocessor 1501 (e.g., FIG. 15) and the graphical user interface 1502 to display a vacuum pressure. The system may further include a display indicating the elapsed amount of time vacuum was supplied to the handpiece by the vacuum pump. The vacuum pump may also modulate the suction such that a higher suction force is applied initially to pull the tissue into the recess, and a somewhat lower suction force is used to maintain/hold the tissue in place thereafter.

Vacuum port 208 may be located in the top wall 201 and/or the perimeter wall 202 of handpiece 100. In some embodiments, tissue apposition surface 203 includes two or more vacuum ports 208 disposed on its surface and configured to apply suction from the vacuum source to the recessed area and to the tissue from different locations of the handpiece.

Figure 2B:
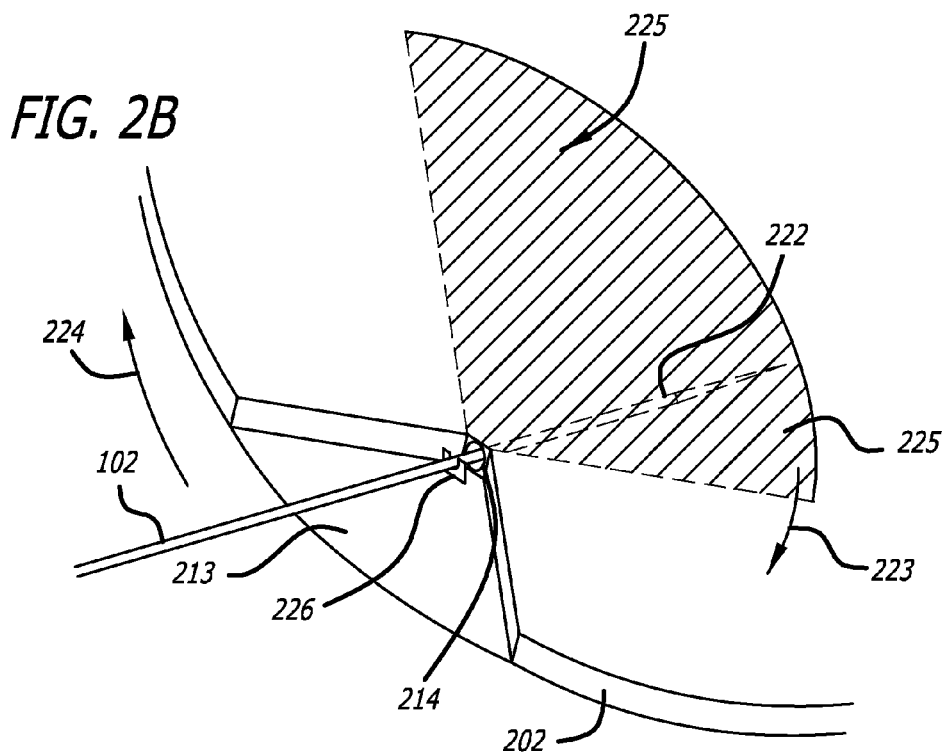

In the embodiment depicted by FIG. 2A, handpiece 100 is seen in use with a vacuum pressure (suction) applied to a portion of skin 101. Suction applied at vacuum port 208 causes skin 101 to be pulled up into contact with apposition surface 205 of handpiece 100. By applying a sufficient suction force, a portion of epidermis 204 is pulled into the chamber of vacuum handpiece 100 and conforms to inner recessed area 105. While the surface of the skin 204 is tightly positioned against top wall 201 and perimeter wall 202 of recessed area 105, fat layer 205 (subcutaneous tissue) is also drawn into the chamber. A cutting tool 102 (e.g., a cutting blade or RF probe, or needle), can be inserted through a conduit 213 in a side of handpiece 100 and through entry hole 214, through the skin, and into the subcutaneous tissue. Significantly, the handpiece enables the cutting tool to be consistently inserted at desired treatment depth 215. Handpiece 100 thus provides for precise control of the depth of the dissection plane and allows for cutting and/or movement of tool 102 substantially parallel to the surface of the tissue along a plane 225 (FIG. 2B).

A membrane 217 formed of a flexible and resilient material may also be applied to the perimeter wall (sidewall) across the proximal (away from the recessed area) or distal ends (closer to the recessed area) of the conduit 213 to minimize vacuum leakage there through. The membrane 217 preferably is sufficiently resilient to seal around the cutting tool as it pierces (self-sealing) therethrough and minimize vacuum leakage. Membrane 217 may be formed of silicone. However, one of ordinary skill in the art will appreciate that other materials may be use to create the self-sealing membrane.

Conduit 213 is disposed in sidewall 202 of handpiece 100, preferably, adjacent bottom or side portion of tissue apposition surface 203. In some embodiments conduit 213 is a through hole defined in perimeter wall 202 or in top wall 201. In other embodiments, conduit 213 is a tube-like member inserted into and/or mounted to a through hole in the perimeter or top wall. Conduit 213 is configured to allow passage of a hypodermic needle, subdermal catheter, cutting tool (as described above), deployment applicator, or other appropriately configured tool through the conduit and into recessed area 105 of the device. The tool may pass through conduit 213 just enough to penetrate the tissue.

Conduit 213 is preferably located proximate a bottom edge 218 of perimeter wall (sidewall) 202 to allow a cutting tool or needle to be inserted into the tissue (captured in the recessed area) in a plane parallel to the dermis. In some embodiments conduit 213 supplies an angle of penetration 219 so that the tool inserted through the conduit will penetrate into tissue disposed within the recessed area, and substantially parallel to the surface of the tissue and parallel to the surface of top wall 201 at depth 215. Specifically, this configuration may provide stability of the tool to maintain an even level, e.g., when the cutting tool is cutting the fibrous structures 220 between the epidermis 204 (and dermis) and the subdermal fat 221. In some embodiments, conduit 213 provides an angle of entry to bias the plane of dissection toward or away from the dermis.

As depicted in FIG. 2B, entry hole 214 is preferably disposed on an inner side of the conduit and facing the recessed area. Conduit 213 preferably widens outward toward an outer side of the perimeter elevation such that a distal end 222 of the cutting tool inserted through the entry hole moves in one direction 223 when a proximal end of the cutting tool outside the conduit moves in an opposite direction 224. Entry hole 214 thereby defines a cutting tool pivot point when a distal end 222 of cutting tool 102 is inserted through conduit 213 and into recessed area 105, and the tool moves primarily in an x-y plane 225 parallel to the top surface of the handpiece. In some embodiments entry hole 214 may include an optional locking mechanism 226 that locks the tool in place upon insertion into the conduit. In some embodiments in which a vacuum is supplied to the recessed area, an optional gasket or seal 217 (not shown in FIG. 2B) may be placed within, in front of, behind, or around entry hole 214 to minimize vacuum leakage.

In some embodiments conduit 213 constrains side-to-side movement of a tool such that movement of the tool through the conduit is limited to a backward direction 227 and forward direction 228. In some embodiments conduit 213 constrains upward and downward movement of a tool such that movement of the tool to maintain the tool in a plane parallel to the surface of the skin 225. In other embodiments, conduit 213 is configured to allow the cutting tool to be moved in an arc 223 parallel to the recessed area of the tissue facing (apposition) surface so as to allow cutting within a subdermal area substantially the size of the recessed surface area.

In some embodiments, conduit 213 has a tool control mechanism (not shown) which allows cutting tool 102 or other tool appropriately configured device, to be controlled by a microprocessor. In such an embodiment handpiece 100 and/or the microprocessor (not shown) controls cutting device 102 to precisely cut an area of tissue disposed within recessed area 105. The area being cut is predetermined and programmed into the microprocessor by the operator of the handpiece.

Figure 3B:
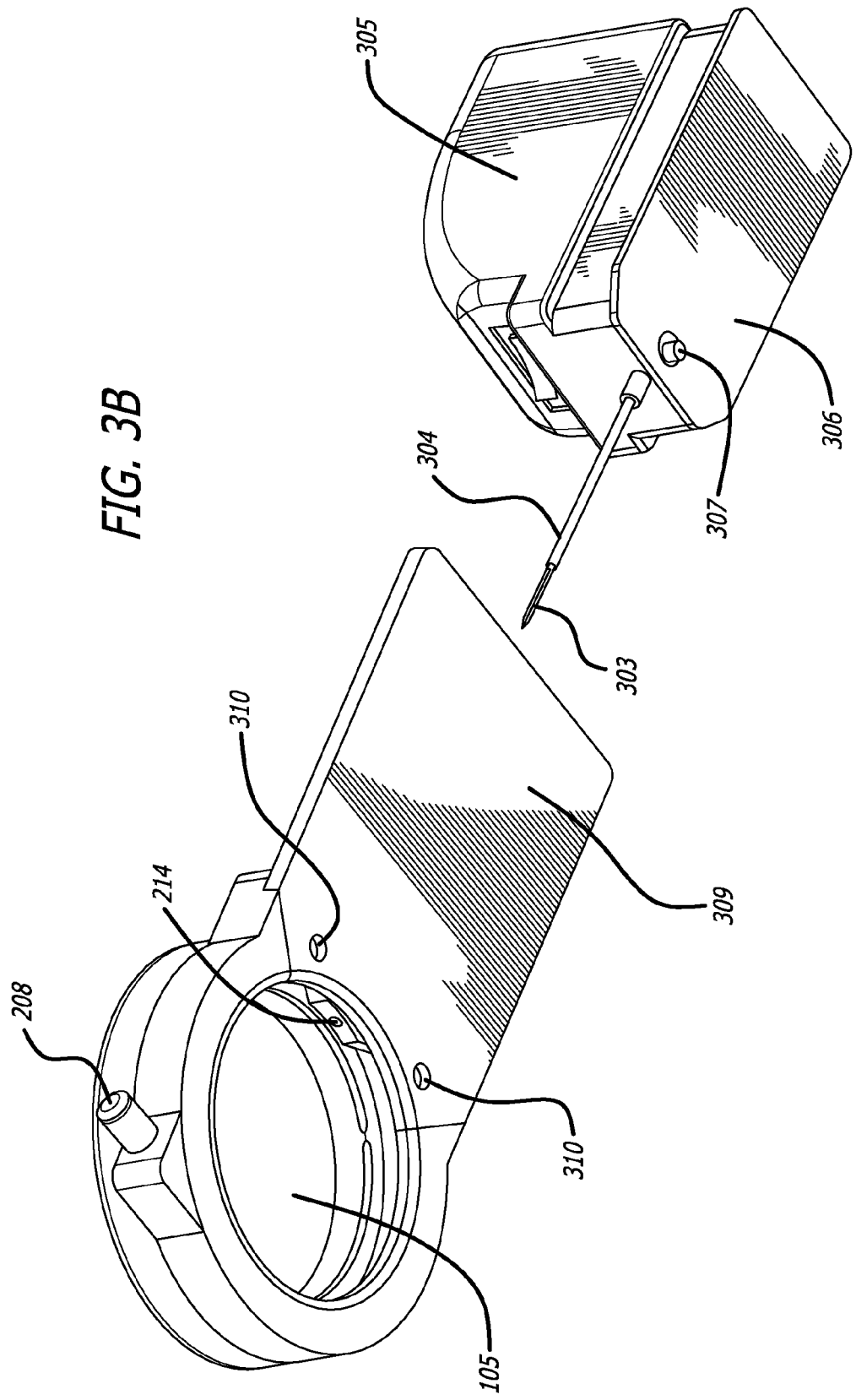

As depicted in FIGS. 3A and 3B, the dissection system may include a motor controlled cutting module 301 and a guidance 302 track operably connected to handpiece 100. In this embodiment, the cutter module includes an embodiment of cutting tool 102 (a reciprocating cutting blade 303 disposed in a sleeve 304) and a housing 305 and a base 306. Guidance track 302 is generally configured to constrain a portion of the cutting module guide pin 307 in contact with the guidance track to move along a predetermined path. Thus, a distal end of the cutting tool, passing through entry hole 214, cooperatively moves within recessed area 105 in a plane substantially parallel to the top of the handpiece and within a region of a predetermined shape defined by the predefined path. Motor operation of cutting module 301 is preferably controlled manually by an electric switch or button 308, but may also be activated by electrical or other contact means known in the art within the guidance track.

Figure 4:
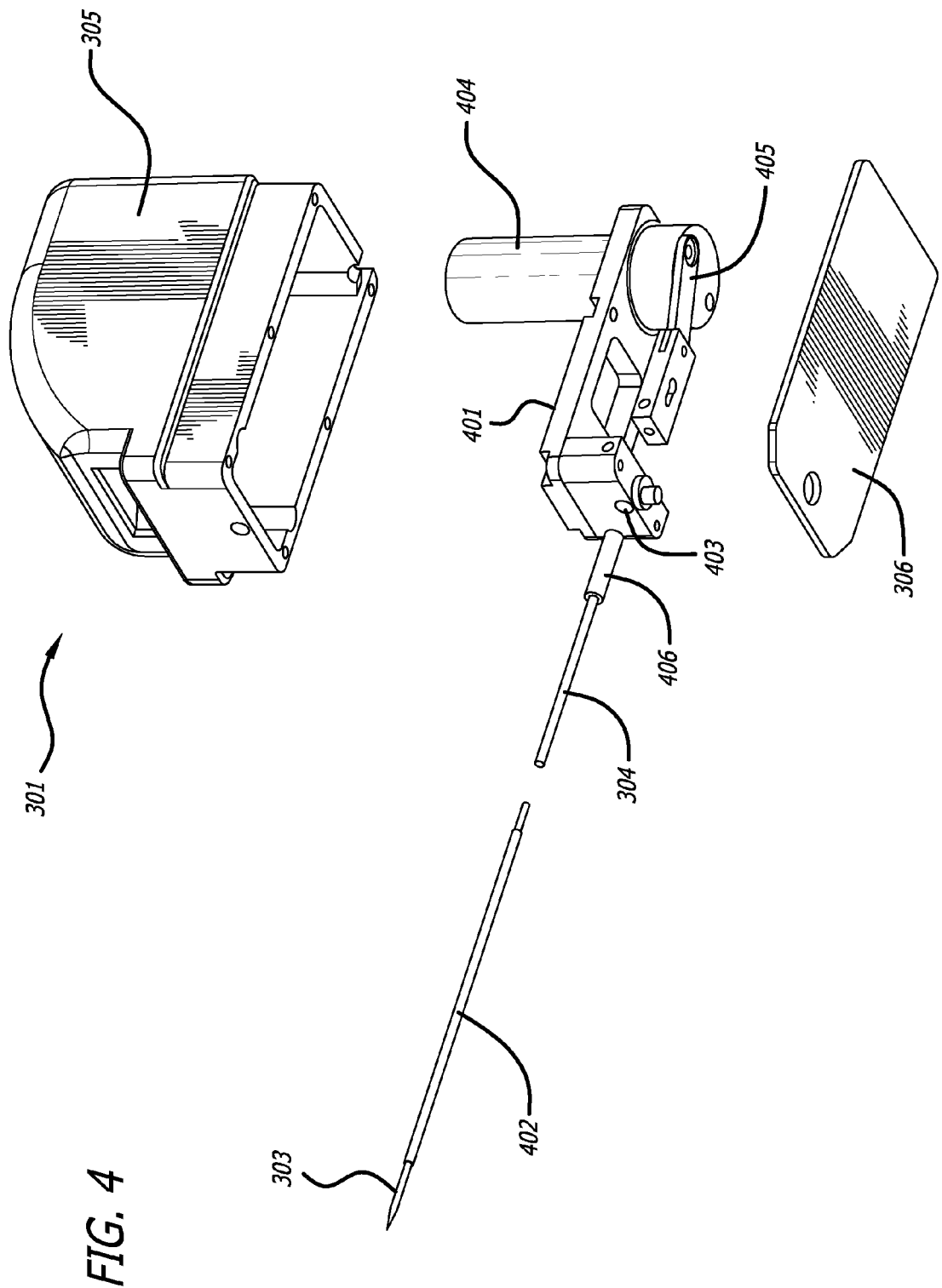
FIG. 4 is an exploded view of the motor-controlled cutting mechanism.

FIG. 4 depicts an exploded view of cutting module 301. Cutter module 301 includes housing enclosure 305 and base 306, motor assembly 401 mounted on the base and enclosed by the housing, and a reciprocating cutting blade 303 operably connected to motor assembly 401. Cutting blade 303 is slidably disposed within sleeve 304. Sleeve 304 minimizes the amount of tissue in direct contact with the shaft 402 of the cutting blade 303 to minimize drag and or tugging on the tissue. Sleeve 304 also enables the isolation and/or capture of any fluid that may travel along the shaft of blade 303.

A motor assembly 401 is enclosed in enclosure 305 and base 306. Sleeve 304 is affixed at a distal end 403 of motor assembly 401. In one embodiment, motor 404 is a DC motor which may incorporate a gear reduction. In the depicted embodiment, a crank slider 405 converts motor rotation to cutter reciprocation. However, it should be understood that other designs which convert rotary to reciprocating motion (e.g., Scotch yoke) may also be employed. Motor 404, within enclosure 305 moves reciprocating cutter blade 303 within sleeve 304. As the motor turns, crank slider 405 moves cutter 303 back and forth within sleeve 304. Cutter blade 303 may include a needle or a bayonet which may further include one or more sharp edges.

As depicted by FIGS. 5A and 5B, sleeve 304 does not reciprocate and is typically comprised of a thin-walled polymer tube and is sterile for single patient use. Sleeve 304 and cutter blade 303 are typically disposable. Sleeve 304 may be affixed to cutter module 301 (and/or crank slider 405) by means of connection point 406. Connection point 406 may be a disposable protective connector keeping cutter module 301 and gear motor assembly 401 in fluid isolation from sleeve 304 and cutting blade 303. For instance, connector 406 may also include a barrier (not shown) enclosing cutting module 301 during operation of the device. In this manner, cutting blade 303 and sleeve 304 could be disposed along with connection point 406 after each procedure. Correspondingly, cutting module 301 including motor assembly 401 and base 306 could be reused in subsequent procedures. In another embodiment, cutting blade 303, sleeve 304, and crank slider 405 may be incorporated into base 306 such that the combined assembly is separate from and operably coupled to the motor 404. In this manner the assembly could be disposed of after each procedure. Radio frequency identification (RFID) or other interlock could prevent re-use of the blade assembly. In some embodiments cutting blade 303 is a bayonet. In other embodiments, a cutting means, such as an RF cutting device, harmonic scalpel, or similar cutting means may be substituted for or used in conjunction with the blade and/or bayonet. If an RF cutting device is used then the device is operably connected to an RF amplifier (see FIG. 16B).

Figure 12A:
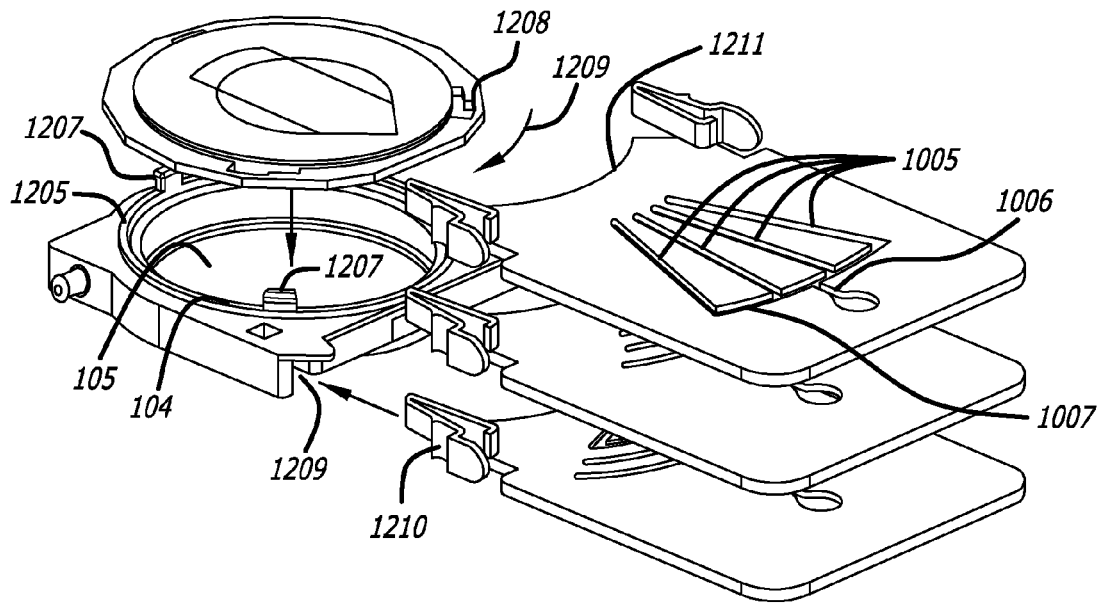
FIGS. 12A and 12B depict the handpiece with a reversible lid and an embodiment of a detachable guidance track.

With reference to FIGS. 3A and 3B, the handpiece also preferably includes a platform 309 integral with or affixed to a proximal side of handpiece 100. Platform 309 may be affixed to handpiece 100, for example, by screws 310 (e.g., Allen screws), a clip mechanism 1209, 1210 (FIG. 12), or any other similar fastening means. Platform 309 preferably includes guidance track 302, wherein guidance track 302 is used to position, guide, and support cutting module 301 by means of a guide pin 307. Guide pin 307 moves within and along the path of guidance track 301 to stabilize the cutter module at a proper position proximate to handpiece 100. FIG. 3B depicts the bottom portions of the handpiece 100 and cutter module 301. Guide pin 307 is located on a side of base 306 proximal to sleeve 304. In the depicted embodiments, guide pin 307 is an protruding feature that interfaces with, or is received by, guidance track 302; however, guide pin is defined herein to be any feature which engages guidance track 302 such as to provide a defined movement of the cutting tool along a predetermined path. For example, guide pin may be a recess or groove wherein guidance track is a raised edge or ridge along guidance track 302 so that the cutting module rides along the raised guidance track to move the cutting tool along the predetermined path.

In this embodiment, guide pin 307 protrudes through base 306 of cutter module 301, however, in other embodiments guide pin 307 may be part of base 306 or cutting module 301. The guide pin may serve dual purposes. Guide pin 307 serves to guide the disclosed cutting module embodiments to create a surgical lesion defined by the path of guidance track 302. Additionally, the guide pin may include a feature such as an enlarged head or the like which interacts with guidance track 302 and prevents cutting module 301 from being lifted off the platform 309 and/or supports cutting module 301 at a predefined planar orientation relative to platform 309. In the drawings, guidance track 302 holds cutting module 301 such that the cutter blade 303 creates a lesion parallel to tissue apposition surface 203, i.e., parallel to the dermis. However, the guidance track 302 could also hold the cutting module such that the cutting blade creates a lesion at a different predefined orientation relative to the dermis. In another embodiment, the guide pin could be motorized and assist or automate the movement of the cutting module through the guidance track.

Turning now to FIGS. 6A and 6B, in one embodiment, the path of guidance track 302 is defined by a central channel 601 passing through multiple arcs 602, the arcs each having a radius measured from a center point located beyond the guidance track in a direction toward the portion of the cutting tool that will provide the cutting action. Moving toward the center point, each successive arc 602 decreases in length and grows smaller. In this embodiment, the penultimate arc is joined with a final inverted arc 603 of the same size to create a closed loop between the penultimate arc and final inverted arc. Central channel 601 does not intersect with inverted arc 603, but, rather, guide pin 307 moving along the path of central channel 601 will move into the final inverted arc by traveling along and beyond an end of the penultimate arc. In the depicted embodiment there are three primary arcs, the last joining the inverted arc. Central channel 601 also has an enlarged opening 604 at its starting position, furthest from the arcs, wherein the central channel is in the form of an elongated substantially straight track moving toward the arcs. This straightened portion allows the cutting module to be positioned within the track at its beginning and to move in a forward direction to insert the cutting tool through the conduit and entry point and into the recessed area. Central channel 601 is also staggered between the first and second arcs and between the second and third arcs to prevent a cutting module traveling along the guidance track from slipping further forward to the last arc before providing the operator of the cutting module the opportunity to move the cutting module in the entire range of the predefined path. In those embodiments in which guide pin 307 has an enlarged head, enlarged opening of the center channel is suitable for receiving the enlarged head, and guidance track 302 includes an enlarged underside for passage of the enlarged head along the path while preventing the cutting module from being lifted off platform 309 and/or supports cutting module 301 at a predefined planar orientation relative to platform 309. In an alternate embodiment, the arcs of guidance track 302 are connected at the outer edges to allow alternate movements of the cutting module between the tracks. This is particularly useful once the dissection is complete so that the motor can be easily moved from the last inverted act to central channel 601.

In alternate embodiments, with continued reference to FIGS. 6A and 6B, guidance track 302 may be removable and replaced with a different pattern which creates a different dissection profile. For instance, a variety of guidance track inserts may be provided so the physician can tailor the procedure to the patient's anatomy and/or the size of the lesion to be created. Guidance track 302 may be inserted into a predefined indentation or cutout 605 in platform 309 and constrained by a locking mechanism 606. The mechanism may include the platform having pivoting arms or levers 607 which rotate within an indentation 608 to overlap a portion of guidance track 302 to constrain it within the platform cutout. FIG. 6A depicts one embodiment of the platform having a removable guidance track 302 with a predetermined path for use with a cutting tool to cut a predetermined shape defined by the predefined path. FIG. 6B depicts an embodiment of the platform having a removable guidance track with a predetermined path for use with an injection device to coordinate movement of a complimentary device having a hypodermic needle or other injection device to inject a solution within a tissue disposed within the recessed area in a treatment area defined by the predefined path.

Figure 12B:
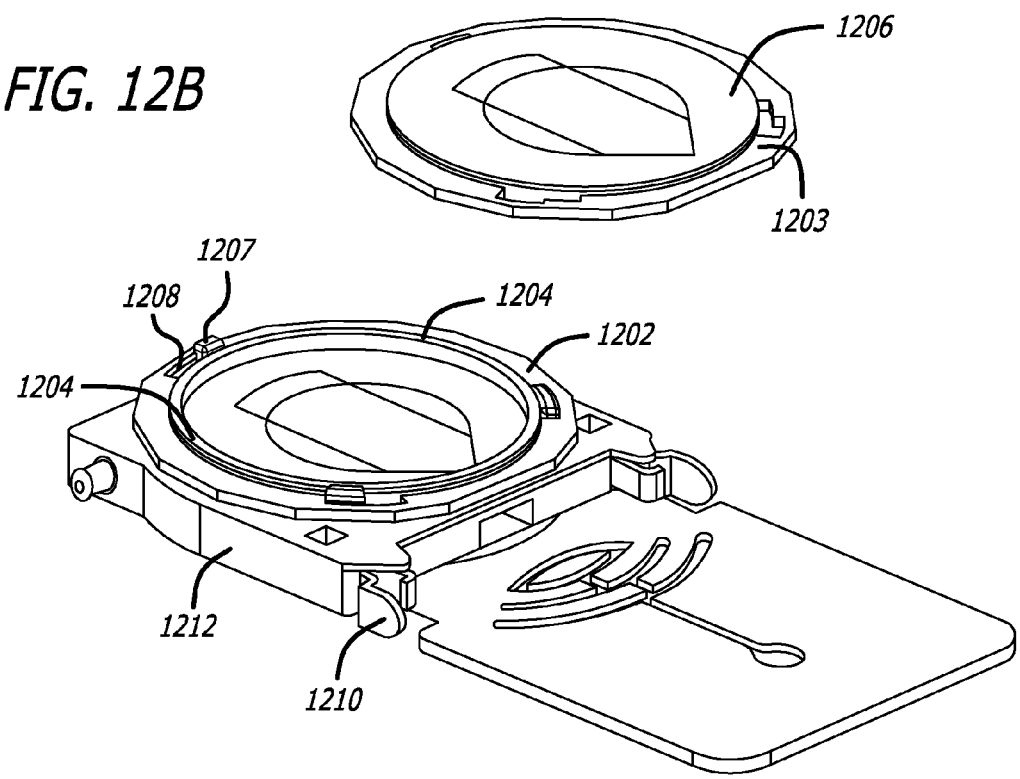

Turning briefly to FIG. 12, platform 309, including guidance track 302, may also be removably detachable from handpiece 100 by a clipping mechanism. In this embodiment, handpiece may include locking receiving spaces 1209 configured to receive complementary insertable clips 1210 affixed to platform 309. Clips 1210 may be made of a bendable material (e.g., plastic or flexible alloy) and face outward from platform 309 at its handpiece facing end 1211. Handpiece is formed such that receiving spaces 1209 are integrally formed from the body 1212 of handpiece 100, in a gap left open between the perimeter wall 104 and recessed area 104 and an outer surface of body 1212. A user wishing to attach or detach platform 309 from handpiece 100 need only cooperatively squeeze clips 1210 inward while inserting or removing them from receiving spaces 1209. Releasing clips 1210 while they are inserted in receiving spaces 1209 will lock platform 309 against handpiece 100.

Figure 7:
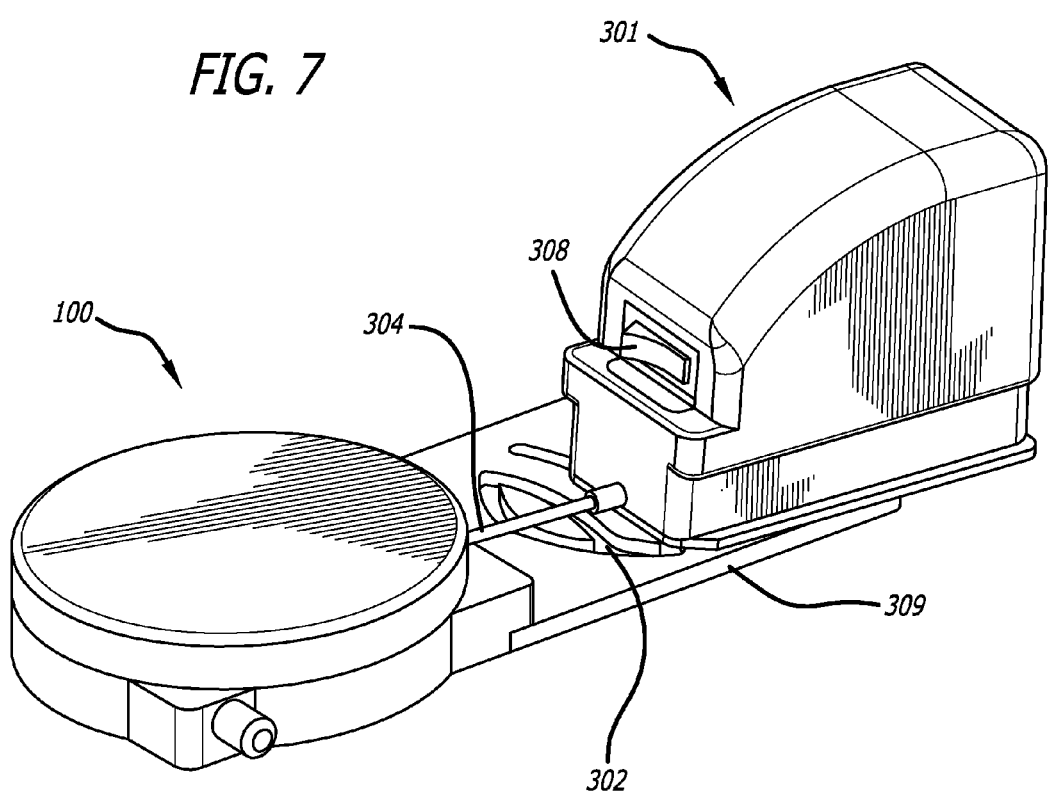
FIG. 7 depicts a perspective view of the handpiece and motor controlled cutting mechanism used in connection with the method.

FIG. 7 depicts the cutting module in use with the guidance track to cut within subcutaneous fat layers 205 at depth 215. Sleeve 304 passes through entry hole 214 of handpiece 100, effectively creating a pivot at the point 801 of contact with the skin. With additional reference to FIGS. 8A through 8C, conduit 213 is wider at a point furthest from entry hole 214. This allows cutting implement 102 or cutting module 301 to pivot about entry hole 214 and move within the desired treatment area 802. Guide pin 307 on the underside of cutting module 301 is engaged into guidance track 302 of platform 309. Accordingly, the bottom of cutter module 301 remains in contact with platform 309 during operation, thus constraining the cutter to operate only in a plane at the desired depth. Engagement between pin and track, combined with pivot at shaft entry hole 214, constrains the cutter to only operate within the desired region. Guide track 302 may be constructed in any number of ways consistent with the practice of the invention. The shape of guide track 302 is not limited to those illustrated by the accompanying figures herein. In some embodiments guide track 302 may be undercut and guide pin 307 may include a flange such that the interface between the flange and the undercut prevents cutter module 301 from being lifted off from platform 309 and/or handpiece 100.

Figure 8A:
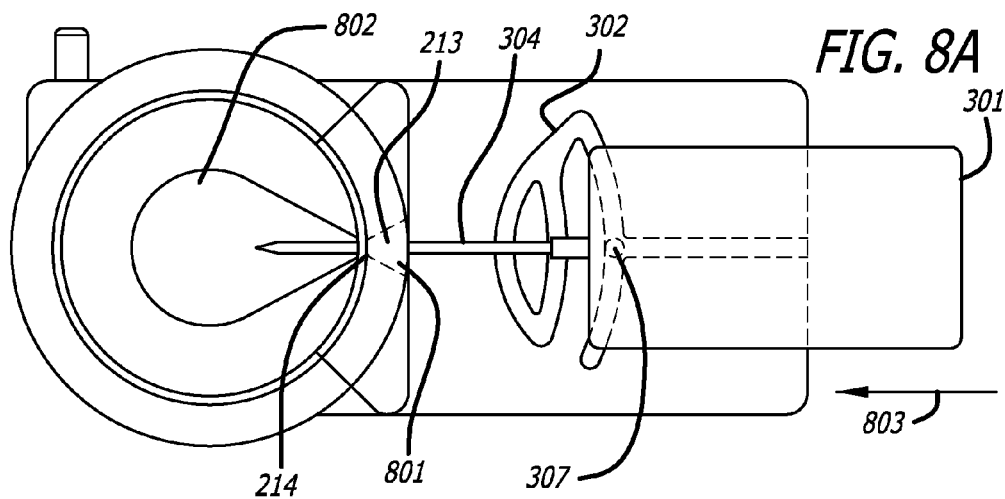
FIGS. 8A through 8C depict the operational range of the handpiece and motor controlled cutting mechanism used in connection with an embodiment of the guidance track.

Cutting region 802 is dependent upon conduit 213 such that, as cutting device 102 is constrained by entry hole 214, it is also constrained by guide pin 307 to move along guidance track 302. Accordingly, the cutting tool moves in a side to side fashion to allow a distal end of the device (including a cutting device, e.g., needle, blade, RF cutter, water jet, laser, ultrasonic or harmonic scalpel) to move along the maximum boundary (laterally and longitudinally) of cutting region 802. FIG. 8A shows the cutting blade entering into cutting region 802. Guide pin 307 is engaged in guidance track 302 as cutting module 301 is advanced in the Y direction 803 until guide pin 307 reaches the proximal arc of the track. At this point, the cutting blade is through the skin and the motor is energized to commence reciprocation of the blade. In further embodiments, the guidance track incorporates a contact (e.g., a sensor) to prevent premature powering of the motor module, or automated powering of the motor module when the motor module has reached the appropriate portion of the guidance track.

Figure 8B:
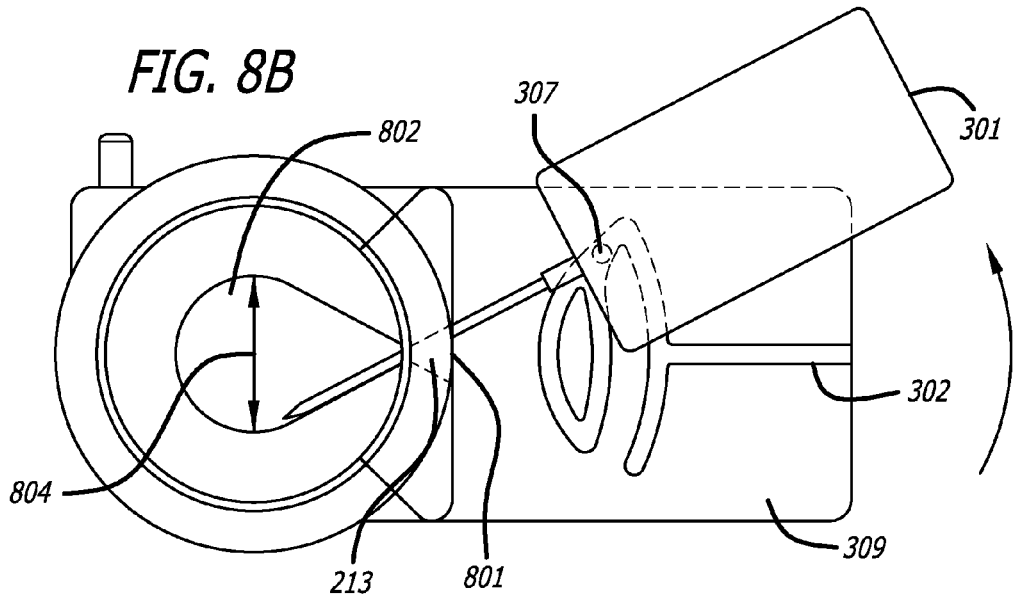

As cutter module 301 is advanced toward the handpiece pin 307 moves along and is restricted by guidance track 302, such that, as depicted by FIG. 8B, as guide pin 307 moves within guidance track 302, a distal end of the cutting tool will move from side to side inside cutting region 802 in a controlled fashion. The path of guidance track 302 defines the size and shape of region 802. Taking the z-axis as the centerline of the handpiece from top to bottom, the path preferably restricts movement of the cutting module, and, thus, the cutting tool moves in an x an y direction within a plane parallel to the top of the handpiece. The interaction between pin 307 and track 302 defines a maximum width 804, or x direction. A physician moves cutting module 301 along the track by beginning the cutting just inside the skin and, following the track to work inward, the fixed (non-cutting) portion of the shaft is always within a region where the tissue is separated; otherwise, the unseparated tissue will prevent the shaft from pivoting freely over the desired region.

Figure 8C:
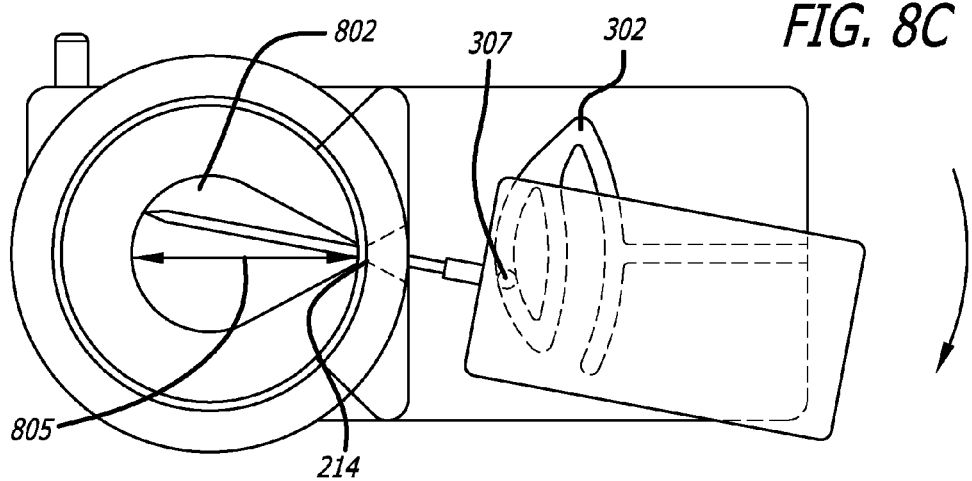

As shown in FIG. 8C, interaction between the pin 307 and the track 302 also defines a maximum length 805, or y direction, of the region 802. The path of guide track 302 preferably defines the region in which the cutting tool will move within the recessed area of the handpiece. The geometry of the track in conjunction with the length of the blade and reciprocation stroke defines the dissection area. After following the entire track the motor is turned off and the cutter is removed. After the power is turned off and prior to removal of the cutter, the dissection can be confirmed by retracing the path with the motor module off. The power may be turned back on to cut any areas not previously released. This same method would apply to any cutting instrument disclosed herein. In the depicted embodiment, the overall resulting region 802 is teardropped shaped. However, the path of guidance track 302 and/or conduit 213 and/or entry point 214 can be altered to modify the shape of region 802 to take the form of any shape.

An alternate range of motion may be enabled by selection of the guidance tracks illustrated in FIGS. 6A and 6B. A physician may also choose to restrict the motor module within the multiple arcs 602 and not complete the outer regions of any one of the arcs. The staggered central track 601 may still be used to advance the module toward the final inverted arc 603. In a further method, the physician may choose to not complete successive arc(s). Thus, by these methods, a reduced area of dissection can be created.

Figure 9A:
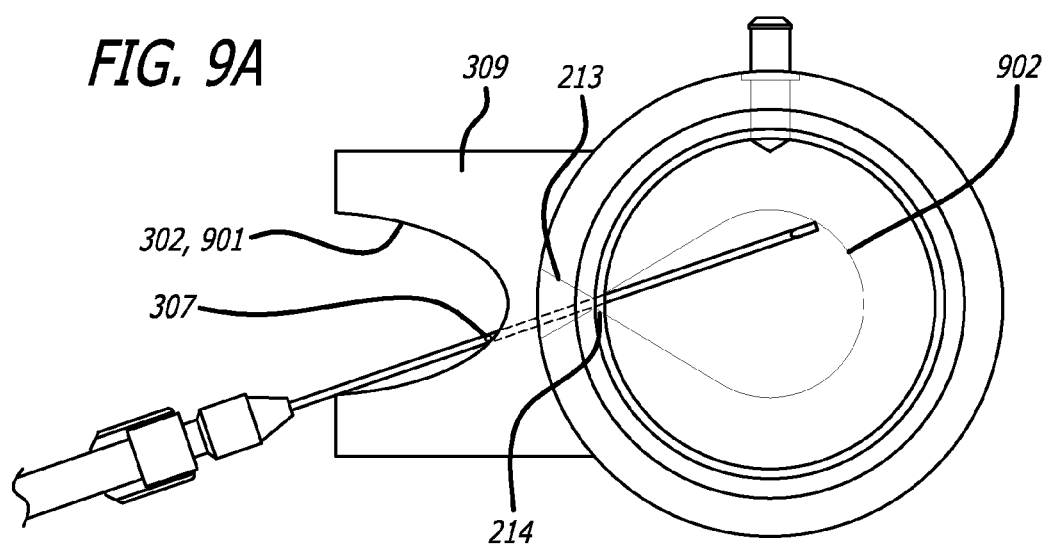
Figure 9B:
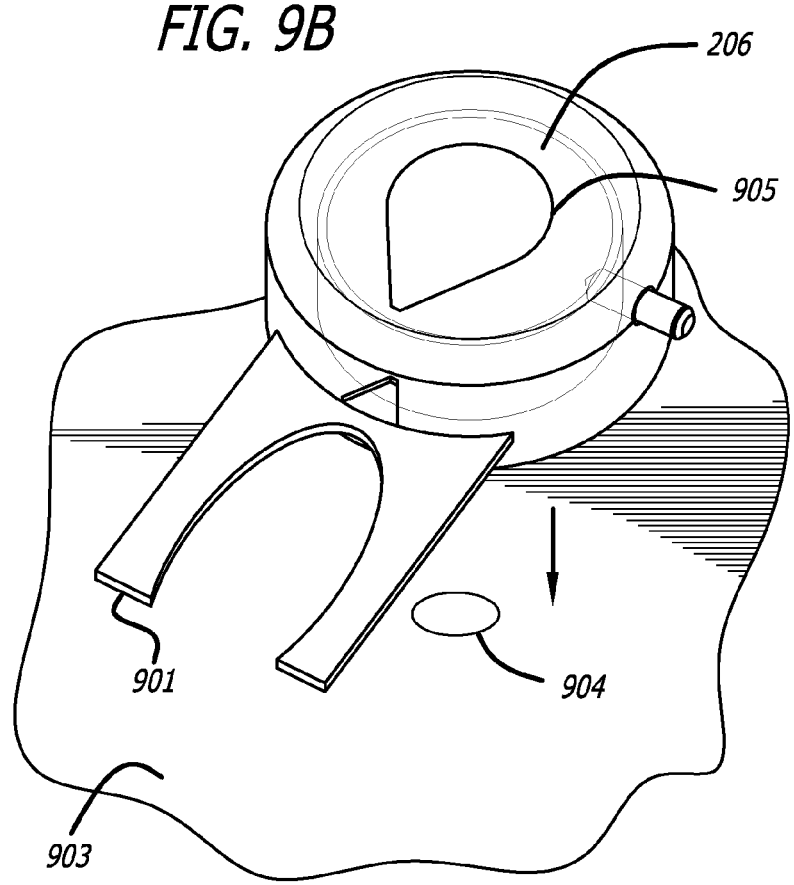

FIGS. 9A through 9C depict an embodiment of platform 309 and guidance track 302. In this embodiment guidance track 302 is a semi-ovoid shape formed along an outer edge 901 of platform 309. Guide pin 307 is positioned on a side of the cutting device (e.g., cutting implement 102 or sleeve 304) such that guide pin 307 moves along the curvature of guidance track 302 and such that the dissection can only occur within the defined boundary 902 (similar to FIGS. 8A to 8C). Although FIGS. 9A through 9C depict the guidance track used with an anesthesia needle, it should be recognized that the depicted guidance track (or any guidance track disclosed herein) can be used with either an anesthesia needle or any cutting instrument disclosed herein.

Figure 10A:
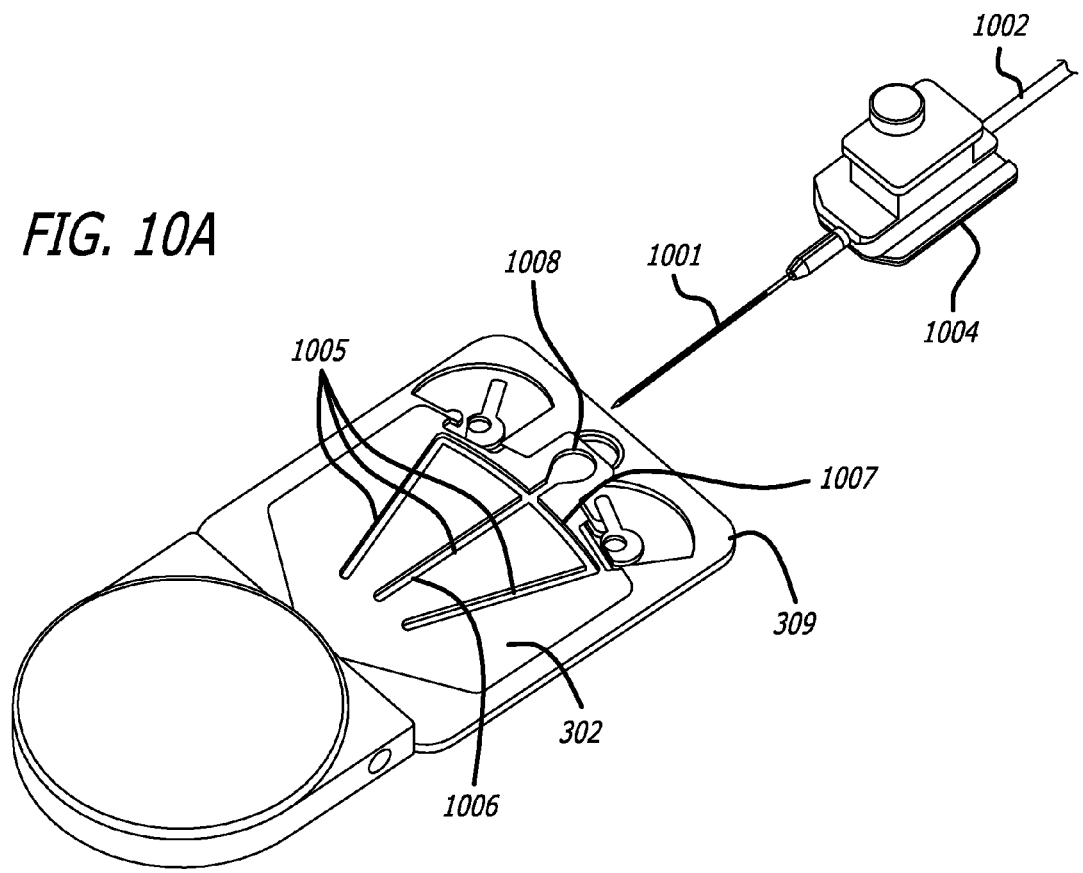
FIGS. 10A and 10B depict an embodiment of the guidance track, including a syringe pump connected to needle or cannula and a source of injectable fluids.
Figure 10B:
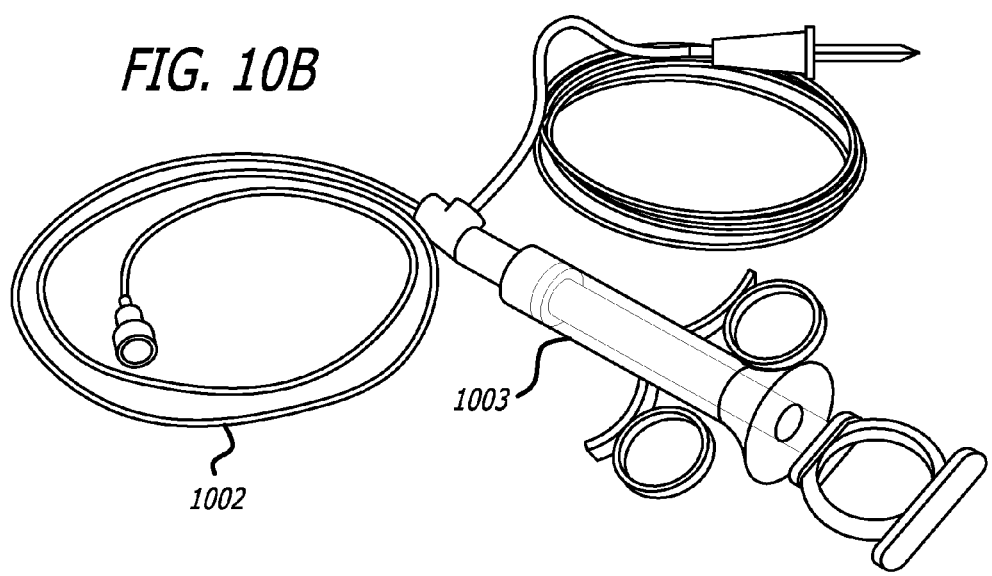
Figure 11A:
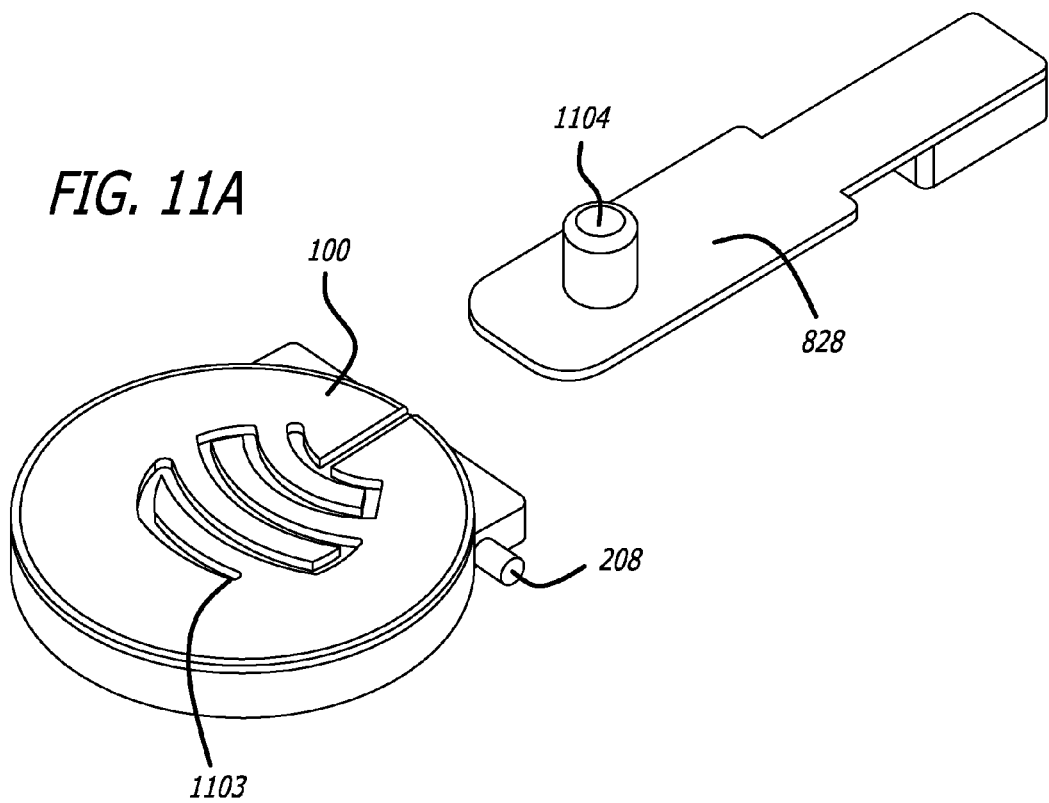
FIGS. 11A through 11D depict an embodiment of the dissection device and cutting tool, including a guidance track positioned on the top of the device.
Figure 11B:
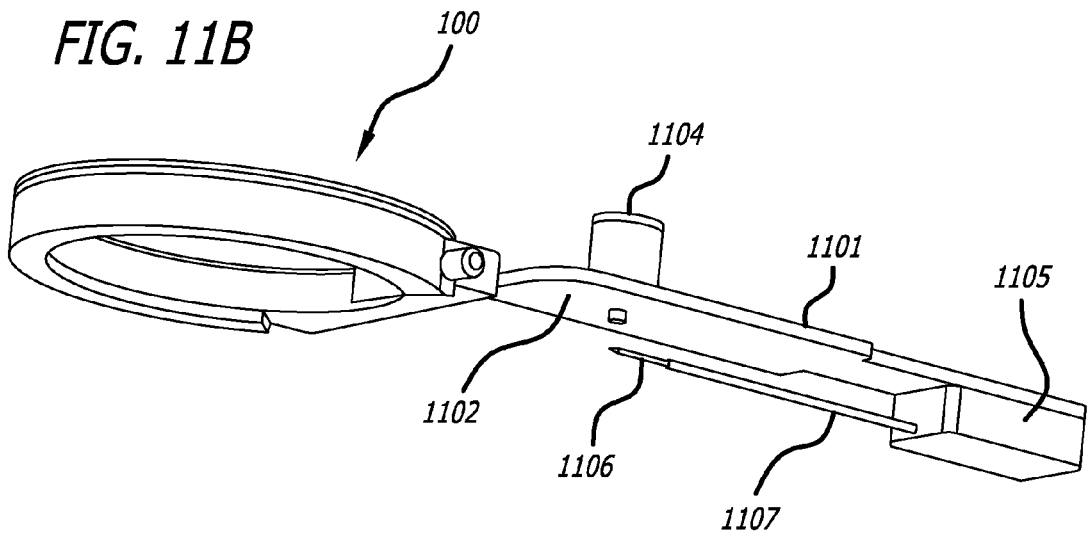
Figure 11C:
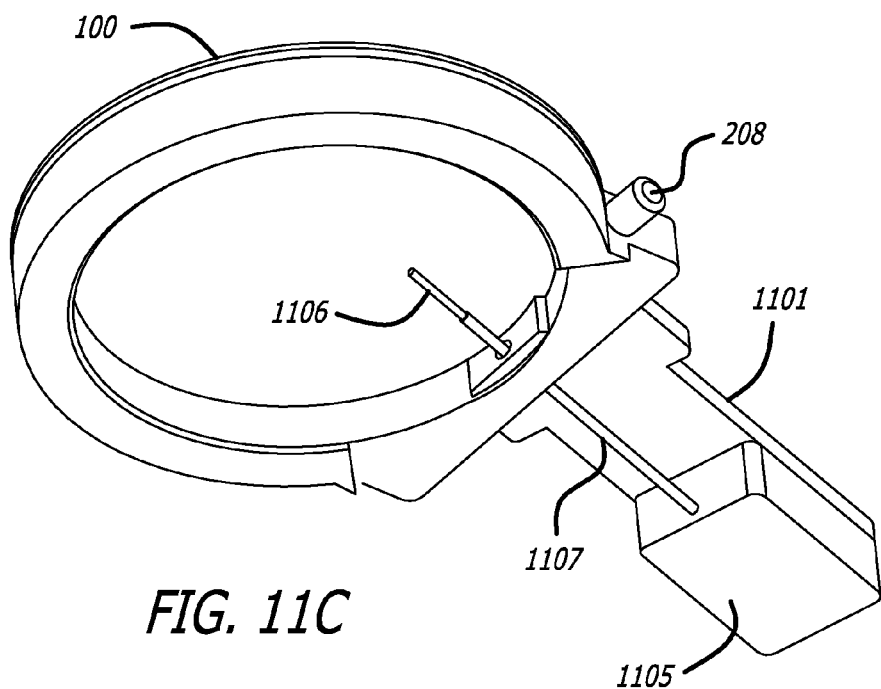
Figure 11D:
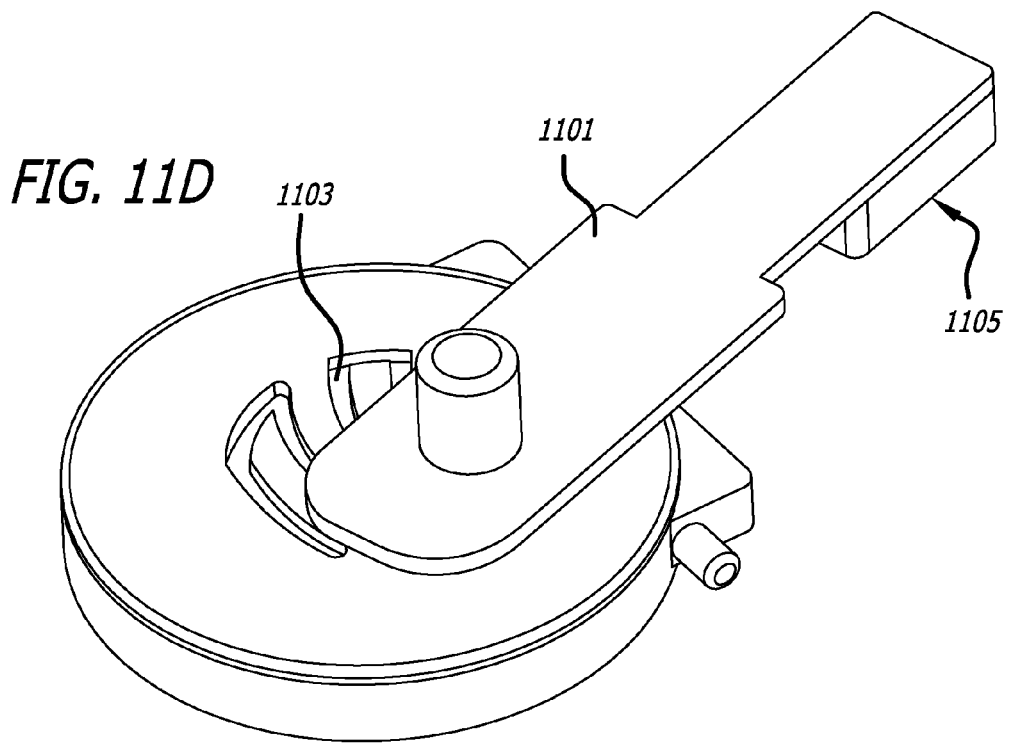

In a further embodiment of platform 309, depicted by FIGS. 10A and 10B, guidance track 302 is configured to provide a controlled delivery of treatment solution through needle 1001. Needle 1001 may be a tube, an hypodermic needle and may have a multitude of holes for increased lateral fluid dispersion. A supply tube 1002 provides fluid connection of needle 1001 with a syringe 1003, syringe pump, roller pump or other injection mechanism known in the art. In certain embodiments, a needle control module 1004 is included to house needle 1001 and to provide support for movement along guidance track 302. Movement of needle 1001 along guidance track 302 provides delivery of the treatment solution in precise locations of the dissection region and minimizes the amount of infusion solution required for a single treatment and/or over multiple treatment sites. Needle control module 1004 preferably includes a guide pin to be engaged into guidance track 302 of platform 309. The guide pin guides the needle/cannula to insure that the injectable fluid is injected into the tissue at the desire depth and desired locations within a predefined treatment area defined by the path of guidance track 302.

An embodiment of guidance track 302 for use with needle control module 1004 includes three radial channels 1005 converging toward a center point located beyond the guidance track in a direction toward the portion of the needle delivering the solution to the treatment area. A central channel provides a straightened portion 1006 that allows the guide pin of needle control module 1004 to be positioned within the track at its beginning and to move in a forward direction to insert needle 1001 through conduit 213 and entry point 214 and into the recessed area. Downward from the starting position of the central channel, the central channel intersects and passes through a cross channel 1007. In this embodiment, cross channel 1007 is in the shape of a wide arc having a center in a direction toward the center point. A radial channel begins at each end of the cross channel such that a guide pin moving along the path of the cross channel will move into a radial channel by traveling along and beyond an end of the cross channel. Each radial channel converges toward the central channel as the needle control module moves in a direction toward the center point. An enlarged opening 1008 of the central channel marks the starting point of the central channel. In those embodiments in which the guide pin has an enlarged head, the enlarged opening of the center channel is suitable for receiving enlarged head, and the guidance track has an enlarged underside for passage of the enlarged head along the path while preventing the cutting module from being lifted off platform 309 and/or supports the needle control 1004 module 1004 at a predefined planar orientation relative to platform 309.

In one embodiment, with continued reference to FIGS. 10A and 10B, when the guide pin on needle control module 1004 reaches cross path 1007 along the central channel 1006, the needle has pierced the skin captured in recess 105. When the guide pin is moved along cross channel 1007, the needle rotates within the pierced area, but does not move forward or exit the skin. Therefore, when the needle is moved by control module 1004 down a converging radial channel and back, cross channel 1007 provides a stop which maintains the needle within the skin. In this manner, solution may be infused over the entire area through a single needle puncture. In a further embodiment, with reference to FIG. 12A, central channel 1006 stops at cross path 1007, and four converging radial channels 1005 can be used for fluid infusion. In this manner, all the converging channels 1005 start and stop, and cross path 1007 prevents the needle from being withdrawn from the skin by requiring the guide pin on control module 1004 to move directly across cross path 1007 from a radial channel to central channel 1006.

FIGS. 11A through 11D depict a yet further embodiment of the platform. In this embodiment, platform 309 of the previous embodiments is replaced by support arm 1101 movably coupled to handpiece 100. Support arm 1101 includes a guide pin 1102 which interacts with a guidance track 1103 defined in the top portion of the handpiece 100. A handle 1104 is used to advance support arm 1101 as guided by the interaction of the guide pin 1102 and guidance track 1103. Guide pin 1102 moves within and along guidance track 1103 to stabilize a cutter module 1105 at a proper position proximate to handpiece 100. Cutter module 1105 can be adapted to use any cutting mechanism disclosed herein. In one aspect cutter module 1105 may include cutting implement 102. In another aspect cutting module 1105 is manually controlled. In the depicted embodiment cutting module 1105 is motor controlled and includes a housing, a gear motor, cutting blade 1106, and sleeve 1107 similar to the embodiment depicted by FIGS. 3 and 4. Guide pin 1102 is located on a lower side of support arm 1101 proximal to sleeve 1107. Cutting module 1105 is fixed to support arm 1101 and thus the support arm is moved to advance cutting blade 1106. In certain aspects cutting module 1105 may include an RF cutter. The compact size of this third embodiment is particularly suited to facial applications.

In further embodiments of the platform, the handpiece may not have a perimeter wall and/or a defined recessed area. In such embodiments, handpiece 100 may include an apposition platform for covering a portion of the dermis to be treated. The apposition platform may include a guidance track 1103 and support arm 1101 to support the cutting tool from above. In some embodiments the perimeter wall does not encompass the entire perimeter of the device, but, rather, encompasses only what is necessary to support conduit 213 and/or entry hole 214. In some embodiments, the platform and guidance track are omitted completely, and, stability and control of cutting tool and cutting below the apposition platform is achieved by manual operation and skill of the medical practitioner operating the device.

Some embodiments of handpiece may include an adjustable top or lid to change the distance between an inner side of the top of the handpiece and the bottom edge of the perimeter elevation of the handpiece. Moreover, in such embodiments, the top of the handpiece 100 is adjustable in relation entry point 214 of conduit 213 to adjust the volume of recessed area 105 and the depth 215 at which cutting tool 102 cuts the subcutaneous tissue when inserted through conduit 213.

In some embodiments, depicted by FIG. 12, the handpiece includes a reversible lid 1201. In the depicted embodiment, lid 1201 has a recessed side 1202 and a raised side 1203. Both sides of lid 1201 are configured to fit snuggly over perimeter wall 104 such as to be easily removed yet maintain a airtight seal to prevent vacuum leakage when a vacuum is supplied to handpiece 100. Depending on which side of lid 1201 is positioned over perimeter wall 104, depth 215 of recessed area 105 will vary. Recessed side 1202 has a shallow rim 1204 which is sized to fit the profile of a top 1205 of perimeter wall 104. When lid 1201 is secured to handpiece 100 with recessed side 1202 faced downward and toward recessed area 105, depth 215 is increased and the volume of recessed area 105 is correspondingly enlarged. Conversely, raised side 1203 has a platform 1206 which is sized to snugly fit within the profile of top 1205 of perimeter wall 104. When lid 1201 is secured to handpiece 100 with raised side 1203 faced downward and toward recessed area 105, depth 215 is decreased and the volume of recessed area 105 is correspondingly reduced. As in the depicted embodiment, handpiece may further include latches 1207, spaced about the perimeter of top 1205 of perimeter wall 104 to securely fasten lid 1201 to handpiece 100 via corresponding locking apertures 1208. Each corresponding locking aperture 1208 is configured to receive a latch 1207 such that when latch 1207 is inserted into aperture 1208 and lid 1201 is subsequently rotated 1209, latch 1207 becomes locked within aperture 1208, and lid 1201 is secured with respect to the latch-aperture communication.

Accordingly, lid 1201 is reversible so that to change depth 215 the operator of the handpiece needs only remove the lid, flip it over, and re-attach it. In some embodiments, an o-ring (not shown) or rubber-like material may optionally be interposed on lid 1201 about rim 1204 and/or platform 1206, or about top 1205 of perimeter wall 104, to provide a secure fit and/or prevent vacuum leakage. In further embodiments, several lids may be provided with multiple and varying recess areas to allow depth to be changed, whether the lids are reversible or not.

Figure 13A:
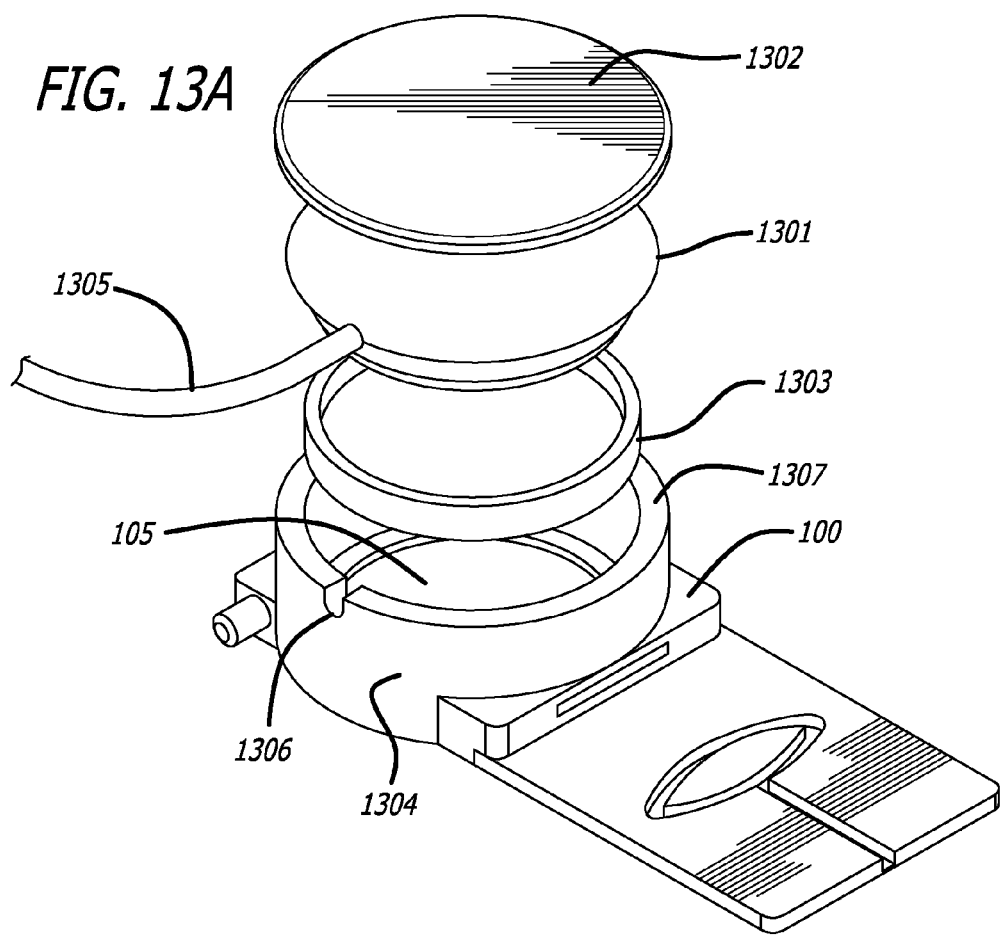
FIGS. 13A and 13B depict exploded and cut-away views of the dissection handpiece, including an inflatable bladder for controlling cutting depth.
Figure 13B:
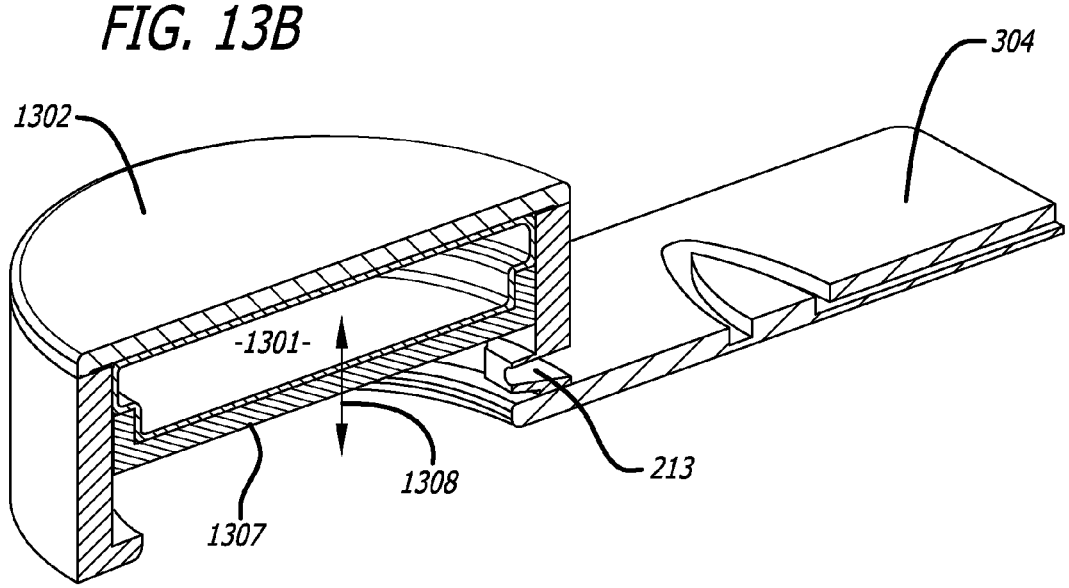

In a further embodiment, depicted by FIGS. 13A and 13B, an inflatable bladder 1301 conforms to the inner diameter of handpiece 100 and is disposed between a rigid outer lid 1302 and a rigid inner lid 1303 Inner lid 1303 is slidably disposed inside the circumference of handpiece 100 whereas rigid outer lid is rigidly mounted to the perimeter wall 1304. Tubing 1305 fluidically connects bladder 1301 to pressure source (not shown) for inflation of bladder 1301. Inflatable bladder 1301, rigid outer lid 1302, and rigid inner lid 1303 are then positioned to fit into the top of handpiece 100, with tubing 1305 protruding through a port or an upper indentation 1306 located along the upper rim portion 1307 of perimeter wall 1304. These components fit together such that rigid outer lid 1302 is coupled to perimeter wall 1304 of handpiece 100, and enclosing bladder 1301 and rigid inner lid 1303 are slidably disposed within handpiece 100. As can be seen by FIG. 13B, adjustment of pressure in bladder 1301 causes inner lid 1303 to raise or lower 1308, correspondingly, thereby changing the volume of recessed area 105 and allowing for selection of a desired dissection depth.

Figure 14A:
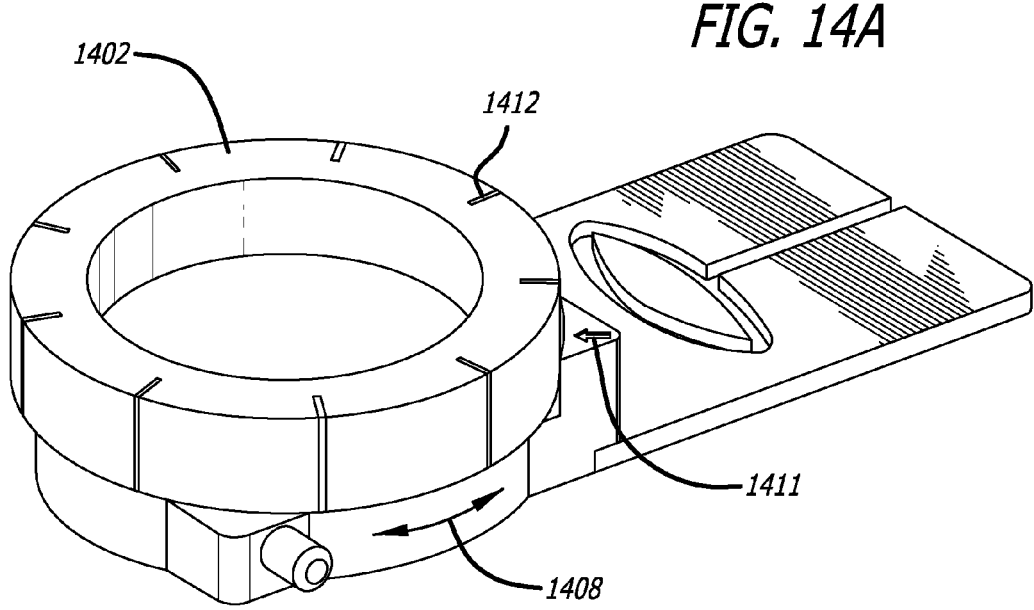
FIGS. 14A and 14B depict exploded and cut-away views of the dissection handpiece, including a threaded engagement for controlling cutting depth.
Figure 14B:
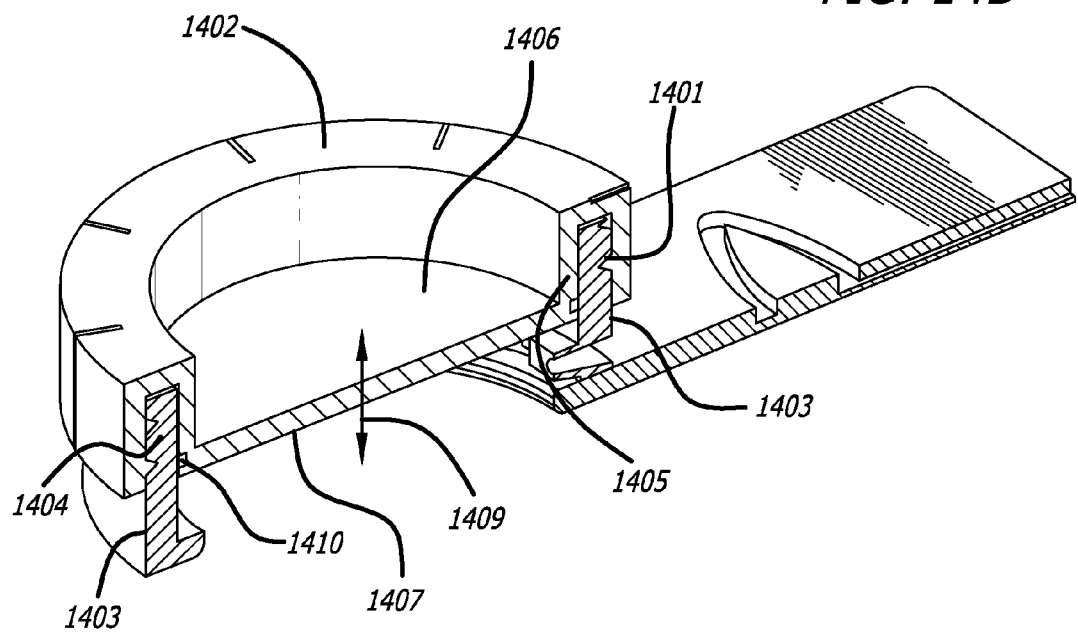

In a yet further embodiment, depicted in FIGS. 14A and 14B, the handpiece includes a threaded engagement 1401 between a threaded lid 1402 and open perimeter wall 1403 of the handpiece. Lid 1402 is threaded onto the upper rim 1404 of wall 1403 similar to a food jar. Lid 1402 includes an outer edge and an inner edge 1405 which grasps rim 1404. Lid 1402 may further include a recessed area 1406 defined by the circumference of inner edge 1405. An interior side 1407 of recessed area 1406, along with an associated portion of perimeter wall 1403 makes up previously described tissue apposition surface 203. Rim 1404 is threaded such that, as lid 1402 is rotated 1408, recessed area 1406 (including tissue apposition surface 203) moves in direction 1409 (orthogonal to the dermis) to a desired depth within handpiece 100. An optional o-ring 1410 may be positioned along the outer circumference of inner edge 1405, between inner edge 1405 and an inner side of rim 1404 to prevent leaking of vacuum applied to the device. Threaded lid 1402 may further include reference numerals (e.g., 9 mm, 10 mm, etc.) defining the depths of tissue apposition surface 203 as lid 1402 is rotated. A reference mark 1411 is placed on the body of handpiece 100 to mark and indicate the current depth setting. Lid 1402 may include further complimentary markings 1412 to be aligned with mark 1411 at various depths.

In a yet further embodiment, the depth is adjustable by way of a sliding platform that moves the entry of the tool device up or down relative to the inside of the lid. Based on the depicted embodiments, one of ordinary skill in the art will appreciate that there are other ways to construct a variable depth vacuum assisted handpiece and such designs fall within the scope of the device and method disclosed herein.

Turning back to FIGS. 10A and 10B, the device and system may further include a syringe pump 1003 connected to needle or cannula 1001 and a source of injectable fluids. The treatment solution may be injected prior to or after deployment of the cutting tool. The treatment solution may include a local anesthetic or pain relieving solution, a vasoconstrictor, an antibiotic, a steroid in normal or buffered saline, or a combination of treatment solutions useful in similar medical procedures. The needle or cannula 1001 can be used to inject the injectable fluid into the tissue prior to, during, or after the creation of a surgical incision. Accordingly, the needle or cannula may be inserted through conduit 213 and through entry hole 214, through the skin, and into the subcutaneous tissue. The needle or cannula may optionally be disposed on a needle control module 1004 for use with an embodiment of guidance track 302.

In some embodiments, needle 1001 includes multiple injection ports along a side of the needle and flush with its outer surface. The ports are configured to discharge a fluid in a direction substantially orthogonal to an axis of the needle and substantially parallel to the top of the handpiece. Multiple ports are used to allow a broader distribution of fluid delivered by needle control module throughout the area of treatment during an injection. The solution will infuse into the subcutaneous tissues, including the subcutaneous fat and adipose tissue. The ports may, in one embodiment, be aligned on a side of needle 1001 so that when needle 1001 is positioned in the subcutaneous treatment area it can be further oriented such that the infusion occurs predominately in the plane of tissue, parallel to the surface of the skin, ensuring that the fluid is further distributed over the largest possible area. In other embodiments, the ports may be staggered. One particular advantage of a staggered configuration is an increased mechanical strength. Another advantage is the ability to infuse solution throughout the treatment area without necessitating perfect alignment of needle 1001. In a further embodiment, the needle may include a partially crimped tip for piercing a dermis while maintaining the ability to discharge the treatment solution from the crimped tip while allowing a simultaneous discharge from the injection ports on its side.

As depicted by FIG. 15, the system may further include a microprocessor unit 1501 having a graphical user interface 1502 to be operably connected to and used with injection device 1003, 1004, a source of injectable solution 1503, a microprocessor controller 1504, and, an optional waste reservoir 1505. A microprocessor and software (not shown) may be included and used to control microprocessor unit 1501 to meter the infusion according to parameters set by the physician. The system can display drug dose or other infusion information and provide warnings or alarms. The needle injection module 1002 and/or a syringe pump 1003 communicates with the microprocessor unit 1501 information specifying the volume of injectable fluids injected into the tissue. The graphical user interface may prompt a user to enter information specifying a concentration of the injectable fluid and a weight of the patient. The microprocessor may include logic for determining a maximum safe dosage of the injectable fluid based on the weight of the patient and the concentration of the injectable fluid. In one aspect, the microprocessor may also cause graphical user interface 1502 to display at least one warning message when the volume of fluid injected by the syringe pump exceeds a predefined threshold which is less than the maximum safe dosage and may instruct the syringe pump to terminate injection when the volume of fluid injected by the syringe pump reaches the maximum safe dosage. In yet a further aspect, the graphical user interface may enable the user to over-ride the maximum safe dosage such that the syringe pump continues injecting the injectable fluids once the maximum safe dosage has been reached.

The graphical user interface also optionally displays an elapsed amount of time since the injection control module and/or syringe pump initiated pumping injectable fluids. In some aspects, the microprocessor tracks the amount of elapsed time since the system initiated pumping injectable fluids and may calculate a recommended treatment start time and a recommended treatment end time. For example, if the injectable fluid includes anesthesia and or a vasoconstrictor, the microprocessor indicates when the surgical incision can be created, i.e., when the anesthesia is effective. Microprocessor may also use information such as the volume of injectable fluids pumped by the syringe pump and elapsed time since the syringe pump initiated pumping injectable fluids to determine the treatment start time and a recommended treatment end time. Microprocessor 1501 and graphical display 1502 can be further configured in some embodiments to control and/or display other information regarding the use of the handpiece or cutting tool. For example, microprocessor 1501 may control the vacuum pump used to capture the tissue in the treatment area and graphical display 1502 may be used to display a vacuum pressure or an elapsed time a vacuum has been supplied to handpiece 100 by the vacuum pump.

In a further embodiment, the device and method may be configured to use a high-pressure stream of fluid such as saline to create the lesion or to sever fibrous septae or disrupt the subcutaneous fat. A cutting device suitable for use with some aspects of the present invention is commercially marked by HYDROCISION™. HydroCision's proprietary FLUIDJET™ technology is the basis of a new surgical modality, HydroSurgery. HydroSurgery uses a controlled hair-thin supersonic stream of water in a precise manner to provide an effective cutting, ablation, and collection system for medical applications. HydroSurgery has the power density of laser and radio frequency technologies without causing collateral damage to tissue. HydroSurgery also has the unique benefit of simultaneously cutting, ablating, and removing the targeted tissue and debris.

In some embodiments needle 1001 is configured to increase a kinetic energy of the solution when it is injected by injection device 1004. Injection device 1004 is guided along guidance track 302 to inject a solution at a high pressure orthogonal to the surface of the dermis, and at depth 215, to cut fibrous septae 220 located in a treatment area located in the subcutaneous tissue 205. It has been determined that a pressure of between 20 and 60 Bar a water jet with sufficient cutting power to cut 8 mm into subcutaneous tissue in one single pass or rotation of the needle. Deeper cuts can be achieved by repeated application on the same cut. Water-jet dissection can also lead to a water uptake of the cut tissue. Morphologically all the vessels, lying in the cut are undamaged if the pressure doesn't exceed 40 Bar pressure range. Preferably, the pressure is thus set to be above 50 bar (in the 50 to 60 bar range) to ensure that fibrous septae 220 located in the treatment area is cut. In this embodiment, needle 1001 includes a nozzle 1506 at a distal end of the needle. Preferably, nozzle 1506 is configured to increase a kinetic energy of a solution injected by the injection device through the needle. In some embodiments, the nozzle is a convergent nozzle. Thus, the throat of the nozzle converges toward the tip of the needle. In other embodiments the nozzle may be a divergent nozzle and/or be configured to slow the kinetic energy of the solution injected.

In a yet further embodiment, the device and method may also use the device and high powered pressure burst described in, and incorporated by reference from, patent application Ser. No. 12/555,746, filed Sep. 8, 2009, which is a continuation-in-part and claims priority from U.S. application Ser. No. 11/515,634, filed Sep. 5, 2006, and from U.S. application Ser. No. 11/334,794, filed Jan. 17, 2006, now U.S. Pat. No. 7,588,547, both of which are incorporated by reference in their entirety.

FIG. 16A depicts an embodiment of the cutting mechanism. In this embodiment, an RF cutter 1601 is used. In other embodiments, another cutter such as a harmonic scalpel (e.g. Ultracision® harmonic scalpel) or the like may also be used. RF cutter 1601 may be positioned in an insulating sleeve 1602 that electrically insulates RF cutter 1601 from the body of RF cutting module 1603. In some embodiments, the shaft or non-cutting portion of RF cutter 1601 may also be coated with an electrically insulating coating. The body of cutter module 1603 may include a handle 1604 which is also electrically insulated from RF cutter 1601. Cutter module 1603 may include a guide pin 307 (as in FIG. 3B), and handle 1604 may be used to guide cutter module 1603 along guide track 302. This embodiment illustrates a specialized handle and RF cutting mechanism for use with the guidance track 302 and handpiece 100. Similar to FIGS. 10, and 11A through 11C, guidance pin 814 moves within guidance track 822 to properly position the RF cutter 1301 within the cutting region. The handle may have control buttons (not shown) which activate the coagulation or cutting modes of the RF energy. In some embodiments, the use of a reciprocating motor such as illustrated by FIG. 4 may be used to reciprocate, move, or vibrate RF cutter 1601. It should also be understood that, in some embodiments, the RF cutter may be provided with a reciprocation mechanism or motor control for reciprocating the RF cutter similar to cutter module 301 depicted in FIG. 4.

In some embodiments, RF cutter 1603 may include a bayonet and/or blade at least partially coated with an insulative coating. For example, if the blade/bayonet is two-sided, the insulative coating may cover only one side, leaving the other side exposed. An additional benefit of leaving the side facing the dermis exposed would be to direct additional energy upward for skin tightening. An electrical connection point 1605 connects RF cutter 1601 by means of an electric cable (not shown) to an RF generator 1609 (FIG. 16B).

FIG. 16B depicts a block diagram of a system for reducing the appearance of cellulite in a patient. The system includes an RF cutting probe 1601, a vacuum assisted handpiece 100, and an RF generator 1606. The handpiece 100 supports the RF probe such that the probe creates a planar surgical lesion at a predefined depth below the dermis through a minimally invasive puncture between 0.4 mm and 4.0 mm in diameter. In other words, the surgical lesion is created without exposing the wound or creating a skin flap. Handpiece 100 has a tissue-engaging surface defining a recess configured to capture a predefined thickness of tissue. RF cutter 1601 is percutaneously inserted into the tissue captured within the recess such that the planar surgical lesion is created at a depth defined by the height of the recess. RF generator 1609 supplies power to the RF cutting probe and includes an impedance measuring circuit for measuring the impedance of the tissue. The RF generator includes feedback control logic which may include a hard-wired electronic circuit and/or software or microcode on a RAM (random-access memory) or ROM (read-only memory) chip executed by a microprocessor or the like within the RF generator. The feedback control logic optimizes the power supplied to the probe based on the measured impedance such that the RF cutting probe cuts efficiently.

The aforementioned system may further include a thermistor or thermocouple (not shown) which may, for example, be provided on the RF cutting probe 1601. In certain embodiments, the thermistor or thermocouple is preferably operably coupled to RF generator 1609 and communicates information indicative of a temperature of the tissue. The feedback control stops the RF generator from supplying power to the tissue when a temperature of the tissue reaches a predefined threshold.

The aforementioned system may contain controlled infusion of a conductive fluid, like saline, to provide additional dispersion of the RF energy, maintain tissue impedance, and/or provide anesthetic benefit.

In some embodiments, a monopolar RF electrode may also be used with handpiece 100 as the return electrode. In this embodiment the system includes an active electrode 1601, an RF amplifier 1609, a vacuum assisted handpiece 100, and a vacuum pump 1606. In one embodiment, handpiece 100 may include an electrically conductive layer (not shown) attached to the interior surface 203 of the handpiece such that, in use, the conductive layer is placed in electrical contact with the skin 204. The conductive layer can be a mesh screen affixed to the handpiece or can be a layer which is sputtered or vacuum deposited on the interior surface of the handpiece. According to some embodiments the conductive layer may be translucent or transparent.

The conductive layer is electrically coupled to RF generator 1609 and thus a conductor electrically coupled to the conductive layer passes through an opening in the handpiece or under the handpiece. The conductive layer may span the entire interior surface of the handpiece or may include one or more windows used to visualize positioning of the handpiece. The conductive layer may be composed of any electrically conductive material, such as copper or aluminum, and/or incorporating an electrically conductive gel. Certain conductive materials may be sputtered or vacuum deposited on the handpiece, providing and additional advantage of being optically transparent (e.g., indium tin oxide (ITO)).

According to one embodiment, the system includes a handpiece fluidically coupled with a vacuum pump 1606 (FIG. 16B), and a needle-like RF electrode 1601 (FIG. 16A) which is inserted through conduit 213 in the handpiece for creating a lesions parallel to the surface of the skin and at a depth 215 defined by the handpiece (FIGS. 2A and 2B). RF electrode 1601 is coupled to RF generator 1609 which includes impedance feedback control logic which may be embodied in software and/or hardware or firmware. The impedance feedback control logic monitors the impedance of the tissue and modulates the power delivered to the electrode to prevent the tissue from desiccating, i.e., preventing a premature impedance spike.

In the disclosed embodiments herein, a subdermal pocket is created using the aforementioned vacuum handpiece in combination with various cutting modalities including cutting blade, laser, high pressure fluid injection (e.g., hydrocision), or RF electrode. After the subdermal pocket is created, the cutting tool is swapped for an RF electrode which is operated in a coagulation mode (as opposed to a cutting mode) to stop any bleeding. Use of the RF electrode in the coagulation mode may result in contraction of collagen in the tissue leading to skin tightening and may lyse some of the tissue. Thus, if the subdermal pocket is created within the shallow fat layer then operation of the RF electrode in the coagulation mode may lyse some adipose tissue. Use of the RF electrode in the coagulation mode may increase the healing response time and may lead to less bruising.

In the aforementioned embodiment, the same RF electrode 1601 may be used both to create the subdermal pocket and to induce haemostasis. Namely, RF electrode 1601 may be operated in a cutting mode to create the subdermal pocket and then may be operated in a coagulation mode to create or induce haemostasis.

Figure 17:
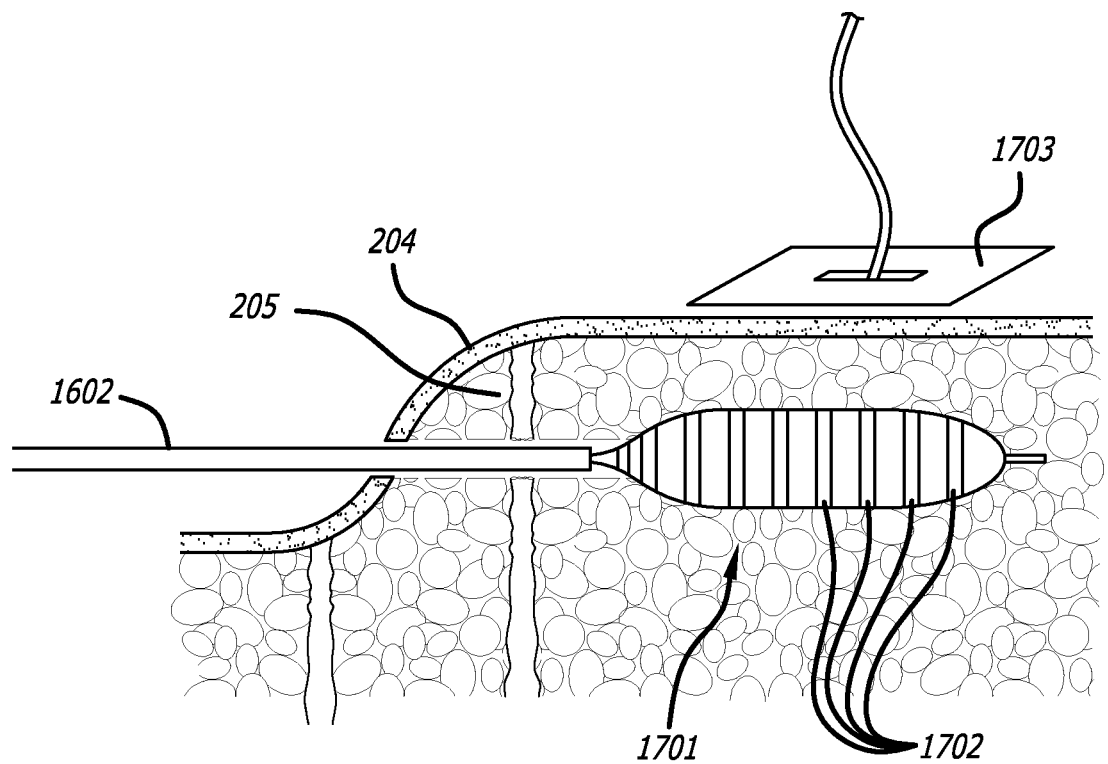
FIG. 17 depicts an embodiment of an RF device, including an inflatable member having an RF electrode provided on an exterior surface.

In one embodiment, depicted by FIG. 17, an inflatable member 1701 having an RF electrode 1702 provided on an exterior surface thereof is used to facilitate coagulation. More particularly, a subdermal pocket below dermis 204 is created using the handpiece 100 in combination with any of the aforementioned cutting modalities including cutting blade, laser, high pressure fluid injection (e.g., hydrocision), or RF electrode. Inflatable member 1701 is inflated within the subdermal pocket and electrode 1702 attached thereto is operated in a coagulation mode to stop any bleeding. It should be understood that the device may also utilize a return electrode 1703 placed in contact with the patient's tissue. In some embodiments, return electrode 1703 may be placed in a location remote from the treatment site. In the depicted embodiment, electrode 1702 includes multiple circular bands disposed about the circumference of inflatable member 1701. However, it should be recognized that the electrode may take the form of other configurations, for example, one or more linearly disposed bands along the length of inflatable member 1701. As described above, the vacuum handpiece may include a return electrode, or the return electrode can be a discrete item separate and remote from the handpiece.

In a further embodiment, the cutting member (i.e., any tool disclosed herein capable of cutting tissue or creating a lesion within tissue) may include an electrode or a heating element. In an embodiment where the cutter includes an electrode, the cutter itself may be the electrode or the cutter may be a discrete element provided on and electrically insulated from the rest of the cutter. In an embodiment where the cutter includes a heating element such as a resistive heating element, the heating element may be provided on a surface of the cutter or may be fully or partially embedded within the cutter. In all such embodiments, the cutter may include a thermocouple to measure the temperature of the cutter and/or tissue. The electrode/heating element may be used to coagulate the tissue, minimize bleeding/bruising, and/or to provide skin tightening.

Figure 18:
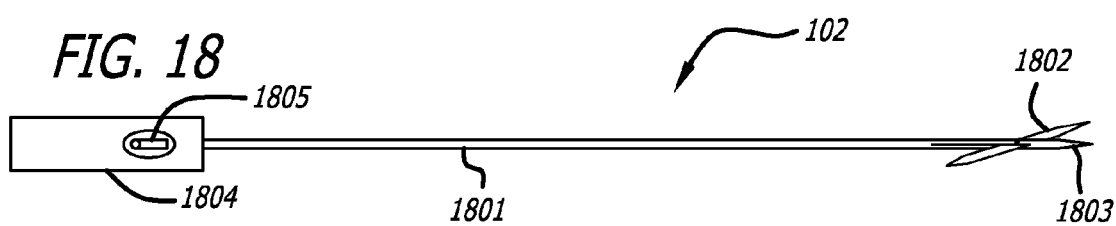
FIG. 18 depicts an embodiment of a cutting tool.

Referring back to FIG. 2A, cutting tool 102 is configured to cut the fibrous septae 220 at the interface between the dermis and the fat layer, within the shallow fat layer 205 which applicant defines as the layer 0-10 mm below the dermis, or, in the deep fat layer 221 defines as the layer 10-30 mm below the dermis, e.g., between the subdermal fat layers and the skin 204, at depth 215. Previously described embodiments included a mechanical or motor-controlled bayonet-like device, RF cutter, a high-pressure injection system, needle-type injection, and the like. Turning now to FIG. 18, the cutting tool 102 may also include an elongated thin hollow subdermal catheter-like instrument 1801 having a retractable cutting blade 1802.

The term "subdermal catheter" is used herein to describe any elongated object which can be used to penetrate the skin or be placed through a hole in the skin, including, but not limited to, a hypodermic needle, a cutting tool, a catheter, or other device that can puncture or be placed through the surface of the skin. The subdermal catheter is inserted through an incision (made by a sharpened distal end of the catheter or other cutting device) between 0.4 and 4 mm because to avoid or minimize residual scarring which are undesirable in a aesthetic procedure. Subdermal catheter 1801 can be rigid or flexible, and may be made of a stainless steel alloy, metal, plastic, or any other material known in the art.

The distal end 1803 of subdermal catheter 1801 is preferably configured to be percutaneously inserted into a treatment area and to move within the treatment area in a manner substantially parallel to the surface of the skin. In some embodiments, distal end 1803 of subdermal catheter 1801 may be honed, composed of a separate sharp tip such as a trocar tip, or may be equipped with unbeveled blunt-tip. It may be placed through the skin with an introducer.

Retractable cutting blade 1802 includes one or more blade members 1804 deployable from a collapsed position to an extended, lateral position. In some embodiments the one or more blade members 1804 are deployable from one or more sides of subdermal catheter 1801 at or near a distal end 1803. In this embodiment, cutting tool 102 preferably maintains a narrow profile, taking on the dimensions of a relatively large gauge needle, so that when blade members 1804 are fully collapsed it may be percutaneously inserted into the subcutaneous level of tissue, in the subdermal fat layer below the epidermis and dermis layers. Blade members 1802 are preferably configured to remain substantially parallel to the surface of the skin when in the extended position. Once deployed, the blade members 1802 can be used to shear fibrous septae 220 which form the aforementioned chambers of fat cells contributing to the appearance of cellulite in the subdermal region by manipulating the device in a forward and backward motion parallel to the epidermis to create a dissection plane beneath the skin. The device has been shown to especially useful in breaking up fibrous structures that are oriented in a parallel fashion (and perpendicular to the skin).

Figure 19A:
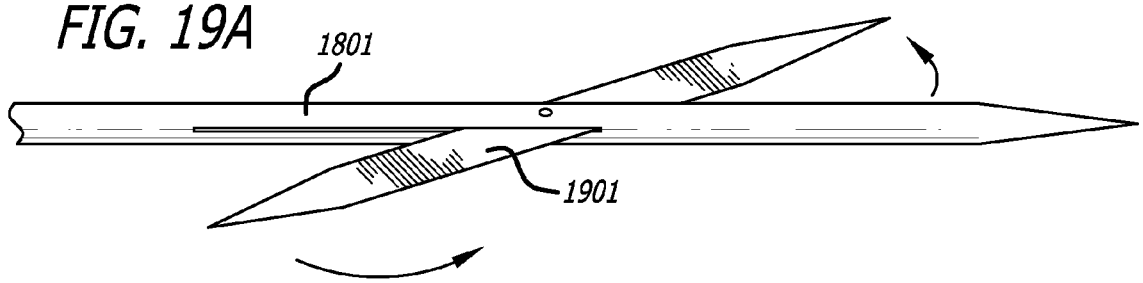
FIGS. 19A through 19C depict embodiments of the cutting tool with one or more retractable blade members.
Figure 19B:
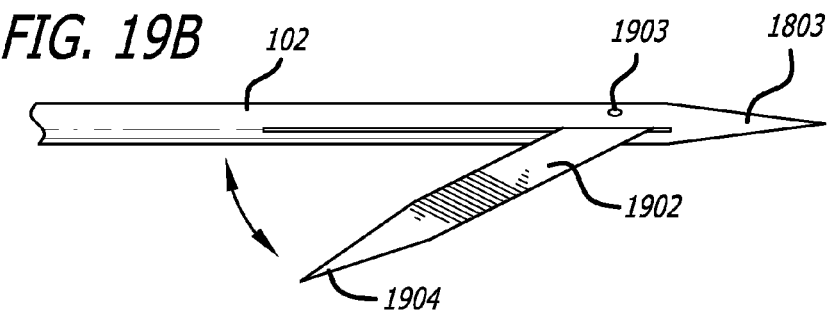

In one embodiment, depicted by FIG. 19A, a single blade member 1901 is pivotably associated with cutting tool 102 at or near a distal end of the cutting tool such that when blade member 1901 is collapsed or retracted it is parallel to the device, and when it is deployed the ends of the blade member extend laterally away from the device. In another embodiment, as shown by FIG. 19B, a single blade member 1902 is pivotably connected at a proximal pivot point 1903 of the blade member such that the blade member 1902 foldably pivots from a closed position wherein the unconnected (distal) end 1904 is proximate to, or inside, subdermal catheter 1801, to an open position wherein the unconnected end 1904 of the blade member extends outward from the pivot point 1903.

Figure 19C:
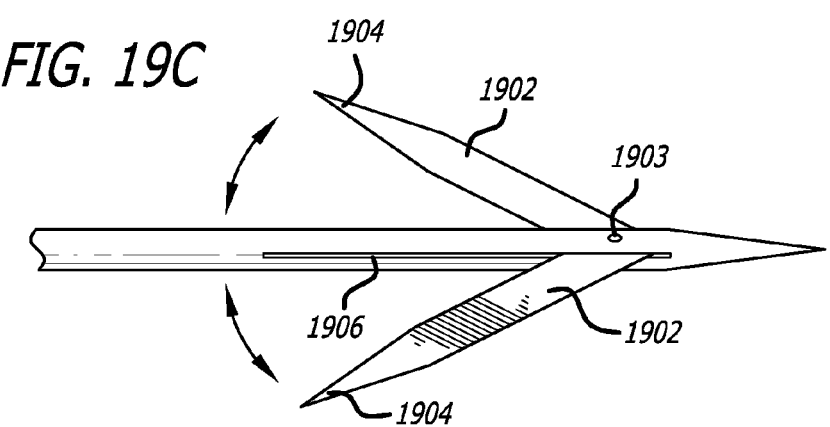

In a further embodiment, as shown by FIG. 19C, the device includes two blade members 1902 pivotably connected at an (proximal) end of each blade member such that the blades foldably pivot from a closed position wherein the unconnected (distal) ends 1904 are proximate to each other, to an open position wherein the unconnected ends 1904 extend outward from pivot point 1903. In one aspect of this embodiment, the two blade members 1902 are connected together at common pivot point 1903. In another aspect, the blade members 1902 may be connected at independent pivot points (each blade having its own pivot point 1903) attached to, or associated with, a common rigid member. As shown by the illustrative embodiments the one or more blade members may be collapsed to and from subdermal catheter 1801 by way of an elongated opening 1906 on each respective side of the device.

Figure 20:
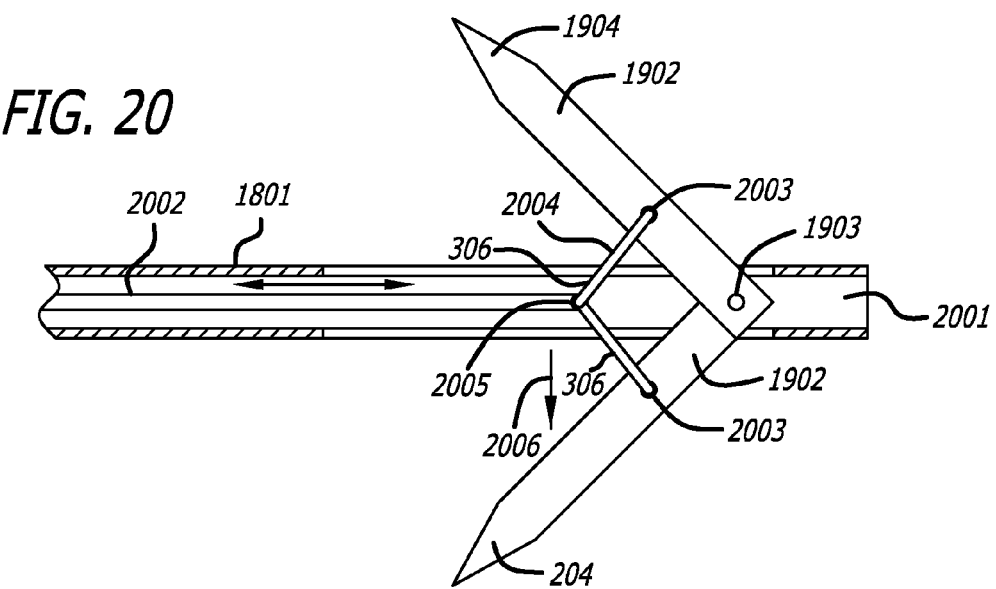
FIG. 20 depicts a blade support mechanism.

In some embodiments, as depicted by FIG. 20, the blade members 1902 are associated with a supporting structure 2001. Supporting structure 2001 may include a hollow tube or may be a flat support surface on which the blade members are pivotably affixed. In some embodiments subdermal catheter 1801 may comprise at least a portion of supporting structure 2001. A deployment member 2002 may move inside subdermal catheter 1801 and/or be associated with supporting structure 2001. In some embodiments, the pivot location of one or more blade members (comprising a common pivot point or a common rigid member having multiple pivot points) is connected to, or associated with, supporting structure 2001 and elongated deployment member 2002 for deploying the blades. Deployment member 2002 moves to release the blade from a constrained position, and may move to retract the blade members from a deployed position. Deployment member 2002 is preferably rigid and can be made of stainless steel, metal alloy, plastic, or any other similar material. The material of deployment member 2002 may also be non-rigid or semi-rigid depending on the embodiment and the application of the device.

Because of the device's narrow profile and protracted cutting blades it is preferable to provide a maximum supporting force for each blade member against the internal lever force imposed on the blade members when coming into contact with and/or cutting through the fibrous septae. Thus, two embodiments of mechanisms that provide efficient deployment and support are explained for illustrative purposes.

With continued reference to FIG. 20, pivot location 1903 is fixed at a point near or at the end of the device. A distal end 2003 of a collapsible support member 2004 is connected to a respective blade member at a location between its pivot point 1903 and distal end 1904 of respective blade members 1902. A proximal end 2005 of support member 2004 is located proximal to device 102 and tracks parallel to the device such that moving proximal end 2005 of the support member 2004 toward fixed pivot location 1903 applies an outward force 2006 on blade member 1902 to move the blade member outwardly from the device.

In some aspects, deployment member 2002 may be associated with proximal end 2005 of support member 2004 from a location distal from pivot location 1903 to a location proximal to pivot location 1903. The support member may have a self-locking mechanism which selectively locks/unlocks the support member in place once it has extended the blade member to the desired location. The self-locking mechanism can be any means known in the art. For example, the self-locking mechanism may lock and unlock by sudden force on the common joint of the support member as a result of an equal force placed on the deployment member.

As the support beam is collapsed, typically by moving deployment member 2002 in a backwards direction, it acts on the blade member to move the blade member from a deployed position to a collapsed position. In embodiments where there are two blade members, support member 2004 may be comprised of two rigid members 2004 pivotably joined together at, and collapsible from, a common center by a common joint 2005, and connected to the respective blade members 1902 at the opposite ends 2003 of rigid members 2004. The proximal end of each rigid member 2004 is located proximal to the device and tracks parallel to the device such that moving center joint 2005 deploys or retracts each blade member simultaneously in a manner similar to that described with one blade member. The two rigid members may lock into a straight rigid position when fully deployed.

In another embodiment, each respective blade member may be deployed using a channel and pin mechanism. A pin may be associated with the blade member near the pivot point. As the deployment member is moved from a proximal to distal position the pin associated with the respective blade moves within a respective channel disposed on a supporting structure. The channel may widen at the distal end to open the blade member into a fully deployed position. In some aspects, the pivot location may also move proximally as the blade member opens and distally as the blade member closes. In some aspects, one or more of the channels may have a lock to secure the blade member via the pin when a respective blade member is in the deployed position. In other aspects, the subdermal catheter or other supporting structure may have a lock channel at a distal end into which the blade member will snap into as it completes deployment. The lock channel may be on a bottom or a top of the supporting structure and the blade member and/or the pivot location may be driven into the lock channel by a spring or by the linear curvature and/or resilient flexibility of the deployment member or any other method known in the art. In some aspects, the deployment member may have a locking mechanism to secure the deployment member in position, and consequently secure the blades in either a retracted or deployed position. The locking mechanism may be actuated from a control located at or near a proximal end of the cutting tool. In these embodiments, support members 301, 306 may be optional.

The descriptions of the above support mechanisms are not intended to be exhaustive or to limit the invention to these precise forms of support disclosed. Other similar support mechanisms found to be technically useful in micro-devices may also be constructed. For example, the blades may use a switchblade-like mechanism for quick deployment with a counter-lever for collapsing the blades, or an electric motor to move the blades between a collapsed and extended position.

In some embodiments, for example, referring back to FIGS. 19A to 19C, the one or more blade members may be collapsed to and from the subdermal catheter device by way of an elongated opening 1906 on each respective side of the device. Elongated opening 1906 may be narrow enough that the opening and closing mechanism (e.g., as illustrated in FIG. 20) and internal area of the subdermal catheter 1801 are substantially protected from the outside. Enclosing the blade members within subdermal catheter 1801 during deployment enables the subdermal catheter to be inserted or withdrawn from a patient minimally invasively. A thin membrane (not illustrated) may be disposed on either or both sides of the opening such as to protect body fluids from entering into the subdermal catheter. In some embodiments the aforementioned membranes may overlap each other to provide better closure. The membrane can be made of any biocompatible material known in the art, e.g., any of the non-absorbable polymeric materials described above.

In some embodiments, the deployment member 2002 and the cutting blades 1902 are deployable from inside the body the subdermal catheter 1801. In these embodiments the blades 1902 may be deployed from a collapsed position from at or near the distal end 1803 of the subdermal catheter. In these embodiments, blades 1902 lie proximal each other inside hollow shaft 2001 and move to an outward position outside shaft 2001. The mechanics of blade members 1902 may be fully or partially exposed, thus not requiring the elongated openings 1906 along the side of the device. In yet further embodiments the elongated openings 1906 are not required, or the device may have partial elongated openings along the side of the cutting device.

In some embodiments the blade members will collapse in a way that they will substantially or completely overlap each other from end to end in the collapsed position. In other embodiments, where the blade members 1902 do not have the same pivot location, the blade members may collapse in a way that, when in the collapsed position, the blades are parallel and adjacent each other from end to end, e.g., as depicted in FIG. 21. The angle of deployment for each blade member may range between 0 degrees in a fully collapsed position to 90 degrees in a fully deployed position. Depending on the stability of the support beam or other locking mechanism it may be more preferable to allow a range between 45-75 degrees so that the device can maintain a narrow profile during deployment, and to maintain maximum stability of the blades during forward and reverse cutting action. Other angles, including an angle greater than 90 degrees are possible depending on various factors, including the skin-type or fat-density of the patient to be treated.

In the illustrated embodiment, device 102 has a handle 1804 located at or near a proximal end of the device for control and positioning the device 102. The handle 1804 preferably includes at least one control wire or rod for actuating the deployment and retraction of the retractable cutting blade 1802. The control wire extends through a lumen in the catheter from the handle 1804 to cutting blade 1802.

The device preferably has a deployment button or similar control 1805 located at the proximal end of the device which actuates the control wire and/or deployment member 2002 to move the blade members from a deployed and collapsed position. The deployment control may, for example, include a control rod or wire which extends through a lumen in a catheter. The lumen supports the lateral sides of the control wire thereby enabling the wire to exert a pushing force without buckling Pushing the deployment control 1805 may collapse the blades while pulling the control may deploy the blades. In some embodiments pushing the control may deploy the blades while pulling the control may collapse the blades. In other embodiments pushing or pulling the control may do both. In some embodiments the cutting device may have a handle or a handpiece at a proximal end of the deployment member.

In some embodiments the device, including the subdermal catheter, will have a round cross-section, while in other embodiments the device will maintain a flat or oval profile. Generally, the cutting device preferably maintains a narrow profile such that it can be percutaneously inserted with minimal invasion to the treatment area. The nominal outer diameter of the cutting device typically ranges from 0.5 mm to 3.5 mm (25 gauge to 10 gauge), but can be smaller or larger depending on the tolerance of the patient. Each of the embodiments disclosed herein include a cutting blade.

Generally, the cutting blades have a nominal width from about 0.5 mm to 3.3 mm and a nominal thickness from about 0.1 mm to 0.8 mm, however, the blade can have a smaller or larger width and/or thickness depending on several factors, including the area to be treated or skin type. For the purposes of illustration, the blade members are substantially flat. Other embodiments may include blade members that are curved, bowed, or angled, or any other design which could be useful in improving the cutting action.

In each of the embodiments described herein the cutting blade includes a shaft portion and a cutting portion where the shaft is defined as that portion which does not contribute to the tissue cutting and the cutting portion is the active and/or sharpened portion of the cutting blade. The length of the cutting blade may vary depending on the specific application and the material properties of the blade. Generally, the longer the cutting blade the more difficult it is to prevent bending or deflection (which is undesirable). For facial treatment applications (acre scar treatment) the cutting blade may range from 2 mm to 5 mm in length; whereas for a cellulite treatment the cutting blade may range from 5 mm to 25 mm in length.

In each of the embodiments described herein the blades may have a sharp or a blunt edge to separate the fibrous septae. In some embodiments the blades are double sided thereby having an edge on each of the longer sides. In other embodiments the blades are single sided. In some embodiments the distal and/or proximate ends may have a sharp edge and/or may come to a point. For instance, the end proximal to the pivot location may be pointed such that the pointed end near the pivot location can be used as a spear to puncture the skin when inserting the device into a treatment area.

One or more of the blade members 1902 may be an RF electrode (monopolar or bipolar). If the blade members are RF electrodes they may be electrically insulated from one another by providing an electrically nonconductive coating on portions of the blade members 1902.

The term cutting blade as used herein should be understood to include an RF electrode, harmonic scalpel or the like useful in cutting tissue in a minimally invasive manner. Thus the cutting blade may or may not include sharpened edges and/or a sharp tip. The term cutting blade may be a single blade having one or more cutting surfaces and also encompasses two or more blades. An RF electrode-cutting blade may be monopolar or bipolar such as such terms are commonly understood in the medical device arts.

Figure 21A:
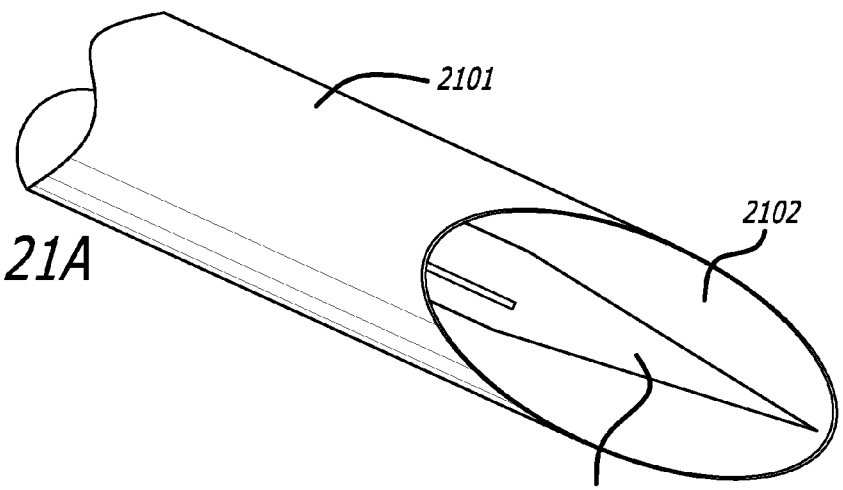
FIGS. 21A and 21B depict embodiments of the cutting tool.
Figure 21B:
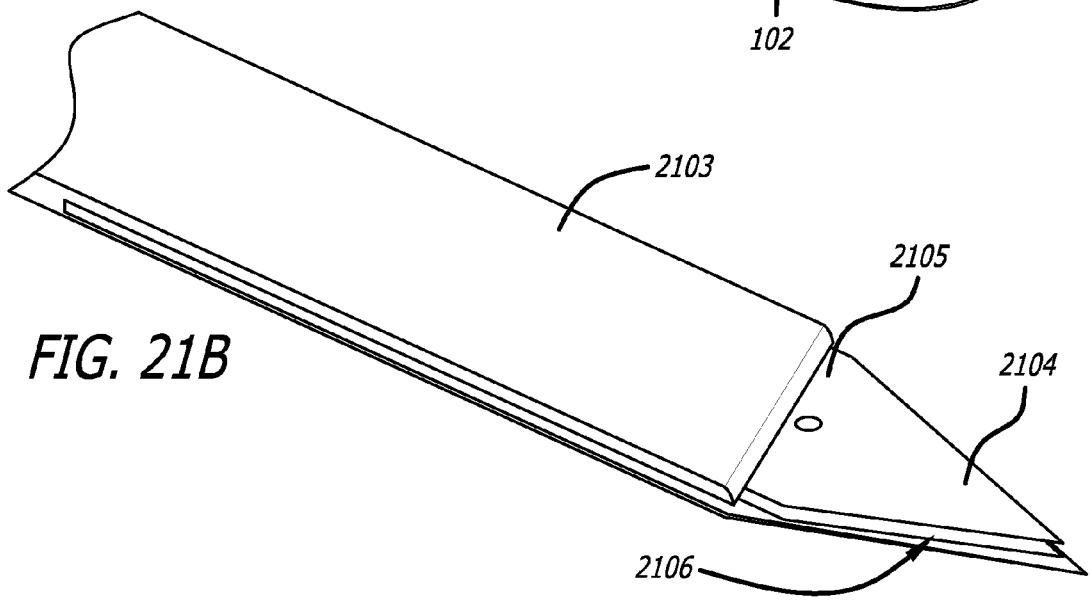

As depicted by FIGS. 21A and 21B, in some embodiments, subdermal catheter 1801 may include an outer housing 2101 that is part of, or associated with, the cutting tool and/or other blade mechanisms herein described. In some aspects subdermal catheter 1801 may also include an outer housing 2101 that is part of, or associated with, a mesh deployment applicator (described below). Subdermal catheter 1801 may be used in conjunction with a handpiece 100. Moreover, the vacuum assisted handpiece supports the cutting tool thereby facilitating a planar dissection parallel to the dermis. In one embodiment, the cross sectional profile of the subdermal catheter is substantially flat so as to maintain a low profile when inserted between the skin and fat layers. In other embodiments the cross sectional profile of the subdermal catheter may be round, square, triangular, hexagonal or any other shape configured for the embodiments described herein.

In one embodiment, cutting device 102, is enclosed in a hollow shaft 2101 which includes a hypodermic needle or skin penetrating means 2102 located at the distal end of the shaft. Needle 2102 is sufficiently rigid to allow skin perforation. In the illustrated embodiment the shaft 2101 of hypodermic needle has a nominal inner diameter sufficient to enclose cutting tool 102, including the blades and their respective deployment mechanism. In some embodiments, hollow shaft 2101 includes at least a portion of subdermal catheter 102. In one embodiment, as depicted by FIG. 21B, the penetration means may include a sheath or slotted needle 2103 such that the end of the blades 2104 protrude from a distal end 2105 of the device and form at least a portion of the penetrating means. Each blade may have a pointed proximal end such that when the blade is collapsed the combination of blade members forms a cutting edge 2106. In a further embodiments the retractable cutting blade members may ride atop supporting structure 2103 near its distal end.

FIGS. 22A through 22E illustrate a further embodiment of cutting tool 102 for creating a plane of dissection which cuts or resects the fibrous septae responsible for creating the chambers of fat cells. FIG. 22A depicts an embodiment of the cutting device including a fluid injection port 2201 in fluid connection with a lumen 2202 in the subdermal catheter. Fluid injection port 2201 may be used for injecting a treatment solution such as an anesthetic and/or a vasoconstrictor into the cutting area before, during, or after the tool is being used in the treatment area. A thin tube may be disposed inside the subdermal catheter (or a lumen may be defined in a wall of the catheter) along with the other mechanics of the cutting device. The thin tube (or lumen) can then be attached to a fitting at the proximal end of the subdermal catheter for fluid connection with a syringe, syringe pump or other injection mechanism known in the art. In certain embodiments the treatment solution can be injected using the subdermal catheter. The treatment solution may include a local anesthetic or pain relieving solution, an antibiotic, or a combination of treatment solutions useful in similar medical procedures. In some embodiments it may further be desirable to substitute port 2201 with an aspiration port operably connected to a vacuum source to aspirate fluid and minimize the accumulation of fluid.

FIGS. 22B through 22D illustrate how the wire may be sharpened or formed to a blade. It is possible for blade 1802 to be made of a sharpened wire 2203, where the wire diameter is from 0.5 mm to 3.3 mm and, as best seen in FIG. 22D becomes a non-circular cross-section after sharpening. FIGS. 22B-22D show how the cross section of the wire changes from circular (FIG. 22B) to non-circular (FIGS. 22C and 22D) as the wire is sharpened. In some embodiments, the pre-sharpened wire may also have rectangular cross-section, and one or more of the edges of the rectangle may be sharpened (not illustrated). FIG. 22A shows the wire implementation, where the wire is deployed to one side 2204 and exits proximal of the distal end 2205 of cutting tool 102. Preferably, the location of wire 2203 exit may range from distal end 2205 to about 3 cm proximal the distal end of the catheter. In one embodiment, the sharpened aspect of the wire faces distal end 2205 of cutting device 102, and the cutting function occurs when the device is pushed in the distal direction. In a further embodiment, the sharpened aspect of the wire faces toward the proximal end, opposite distal end 2205, and the cutting function occurs when the device is pulled back from the distal position. Optionally, both edges of the wire may be sharpened for cutting in either direction. Cutting wire 2203 may also be optionally gradually deployed in a series of cutting sweeps, where with each sweep the wire is deployed further to achieve a wide dissection plane. FIG. 22B represents a non-sharpened portion of the wire, FIG. 22C represents a semi-sharpened portion, and FIG. 22D depicts a fully sharpened end for cutting when deployed from device 102. Port 2201 may dispense for dispersing a solution into the treatment area or remove tissue from the treatment area as the device is used to cut fibrous structures and/or destroy adipose tissue.

Sharpened cutting wire 2203 may also form an RF cutter include an RF (radiofrequency) electrode connected to an RF amplifier (see FIG. 16B). As previously described embodiments, insulating coating may be applied to the length of the electrode, leaving only a relatively small exposed (active) portion at or near the distal end of the wire. Wire 2203 may be used with or without activating the RF energy. Thus the RF may assist in the cutting. RF energy may be supplied to wire 2203 in either a cutting or coagulation mode as desired. It may be desirable to activate the RF energy only after wire 2203 is positioned subdermally at the desired depth to prevent or minimize injury to the skin. Moreover, the wire electrode 2203 may be used to confirm resection by sweeping the unpowered wire electrode through the cutting plane. RF amplifier 1609 supplies RF energy to the probe 2203 or any of the other RF probes disclosed herein.

Throughout this disclosure the term mesh will be used to refer generally to any generally planar foreign body sheet of material which is implanted into subcutaneous tissue. The mesh may be composed of sutures, filaments, fibers, fibrous structures, scaffolding, quills or the like. The mesh used in any of the embodiment described herein may be bioabsorbable such that the mesh dissolves or is otherwise absorbed by the body over time. Each of the embodiments disclosed herein may be used to treat targeted areas, such as the upper leg below the buttocks where cellulite is most visible.

The mesh may be implanted under the skin in order to promote increased connections between the skin and the fat and increase the durability of the reduced dimpling cellulitic appearance. In one embodiment the mesh may be made of any of a range of materials including but not limited to polypropylene, nylon, collagen, polymers of polyester, glycolide, or other suture materials. The mesh may either be absorbing or non-absorbing. The thickness of the mesh can vary from 0.01 mm to 0.05 mm and the area of the mesh may range from 1 mm to 100 mm. The mesh may be formed in squares, circles, rectangles, or irregular shapes that are custom cut to the patient needs.

In the embodiments disclosed herein it is preferred that the mesh include a plurality of pores to promote the in-growth of tissue. More particularly, the pores preferably have a pore size ranging from 50 μm to 5 mm such that it can become ingrown with tissue at that site to serve a useful therapeutic purpose. The pore size is patient dependant, and different pore sizes will be indicated for different patients. The goal pore size is as small as possible to create a smooth appearance and a maximum amount of fibrous attachment through the mesh; however, large enough to promote rapid attachment of cells and maintain a highly flexible and natural looking appearance.

In one embodiment, the implantable mesh is reticulated, such that it is comprised of an interconnected network of pores, either by being formed having a reticulated structure and/or undergoing a reticulation process. This provides fluid permeability through the implantable mesh and permits cellular in-growth and proliferation into the interior of the implantable mesh. In further embodiments the mesh may include quills, sutures or other structures which bind into the surrounding tissue.

The mesh may be textured or treated on one side to promote binding to either the skin or the fat side. The mesh may be textured or treated on both sides to promote binding to both the skin side and the fat side. The treatment on the mesh may be a growth-promoting chemical to encourage rapid in-growth into the mesh from the body, and/or biologically acceptable glue may be used to bind one or both sides of the mesh.

The mesh may be composed of stiff materials or flexible materials. Preferably, the mesh is highly flexible and easily contours to any curvature. The mesh may be made of component material that is elastic or non-elastic. In addition to being flexible, it may be desirable for the mesh to be composed of elastic materials. Moreover, according to one embodiment the mesh may be attached to tissue on both upper and lower planar sides (parallel to the dermis) thereof. Attachment of the mesh may be by way of adhesive glue or the like, sutures, staples, barbs, hooks or the like. In the case of non-elastic material, the mesh will likely need to be bound on one side and free to move on the other side. Upon implantation, the mesh reduces dimpling by creating a substantially high density of attachments (new fibrous septae) between the skin and the fat, thus reducing the appearance of dimples and heterogeneity on the skin surface. Over long term, e.g., 3-6 months after implantation, the mesh promotes more fibrous tissue which further reduces the appearance of cellulite.

In some embodiments, a self-expandable frame is used to deploy the mesh into its correct position and orientation. The mesh may be removably attached to a self-expandable frame for delivery into the subcutaneous tissue, either in the subdermal fat or in the layer between the subdermal fat and the skin. The self-expandable frame can be constructed of any self-expandable material, such as a nickel-titanium alloy (e.g., NITINOL®). The mesh can be attached to the frame by any suitable method known in the art, e.g., it can be sutured to the frame with a biocompatible suture material, glued to the frame using biocompatible glue, or even heat-bonded to the frame, where the frame has been pre-coated with a suitable heat-activated polymer or adhesive. In certain embodiments the implantable device (mesh and/or frame) can be constructed to conform to different shapes and sizes to accommodate a range of patient skin types, weight, height, diameter, or the like. The intention is to remove the frame after the mesh is delivered.

The implantable device may also include a biocompatible, reticulated (i.e. resembling or forming a net), resiliently compressible elastomeric material that is generally flat, flexible, and can recover its shape and most of its size after compression. In some of these embodiments the elastomeric material may be comprised of a bioabsorbable polymeric material.

In some embodiments, the implantable device (frame and/or mesh) has a resilient compressibility that allows the implantable device to be compressed under ambient conditions, e.g. at 25° C., from a relaxed configuration to a first, compact configuration for in vivo delivery via a delivery-device and to expand to a second, working configuration, in situ. The implantable device can be suitable for long-term implantation and having sufficient porosity to encourage cellular in-growth and proliferation, in vivo. Preferably, the implantable device is constructed such that it may be encapsulated and ingrown within the treatment area, and does not interfere with the function of the regrown cells and/or tissue, and has no tendency to migrate.

In some embodiments, the period of implantation will be at least sufficient for cellular in-growth and proliferation to commence, for example, in at least about 4-8 weeks. In these embodiments, the device may be sufficiently well characterized to be suitable for long-term implantation by having been shown to have such chemical, physical and/or biological properties as to provide a reasonable expectation of biodurability, meaning that the device will continue to exhibit biodurability when implanted for extended periods of time, e.g. the device may include a biocompatible elastomer that may be considered biodurable for the life of a patient.

Furthermore, in certain implantation applications, it is anticipated that implantable device will become in the course of time, for example, in 2 weeks to 1 year, completely absorbed, encapsulated by tissue, scar tissue or the like, or incorporated and totally integrated into, e.g., the fibrous septae repaired. In some embodiments the implantable device is completely biocompatible such that the probabilities of biochemical degradation or release of undesired, possibly nocuous, products into the host organism may be attenuated if not eliminated.

As shown by FIGS. 23A through 23E, the system may include a mesh deployment applicator 2301 to deploy a fibrous mesh 2302 through a single needle hole in a dermis to create a highly fibrous layer directly or through wound healing processes. The implantable mesh may be self-expandable, and is generally flat, flexible, and can recover its shape and most of its size after compression. In other embodiments mesh 2302 may be detachably coupled to a resiliently compressible self-expandable frame (not illustrated). In a first embodiment, implantable mesh 2302 is preferably disposed at or near a distal end 2303 of deployment applicator 2301. The applicator is inserted percutaneously through the skin using a subdermal catheter such as that described above, or by itself through a hole in the skin, to deploy the implantable mesh located at or near its distal end to a treatment area in the subdermal fat or in the layer between the subdermal fat and the skin. It should be noted that the mesh applicator may be combined in a kit or a system with any of the dissection devices and/or the vacuum-assisted hand piece described herein. Specifically, the mesh applicator may be included with handpiece 100 to be deployed through conduit 213. The dissection devices disclosed herein may be used to create a subdermal pocket sized to receive the mesh.

Figure 23A:
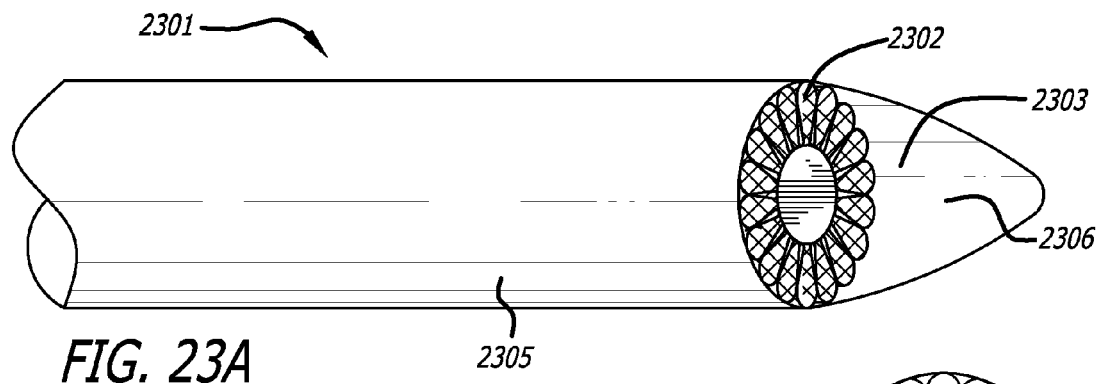
FIGS. 23A through 23E depict a first embodiment of a mesh deployment applicator.
Figure 23B:
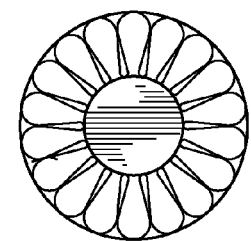
Figure 23C:
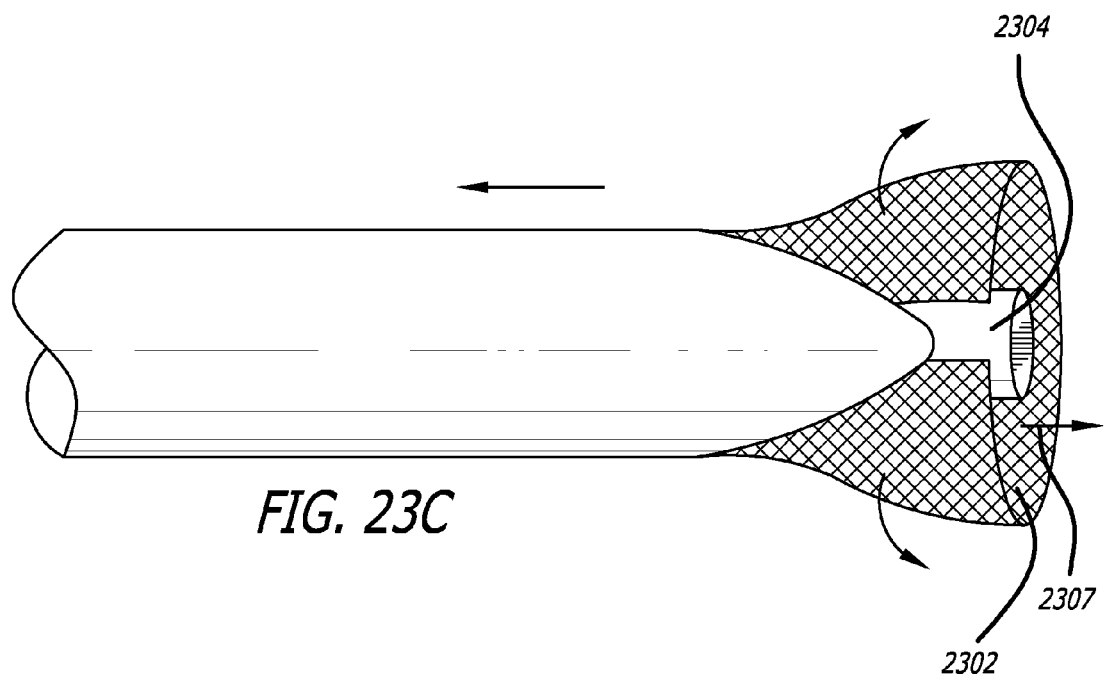
Figure 23D:
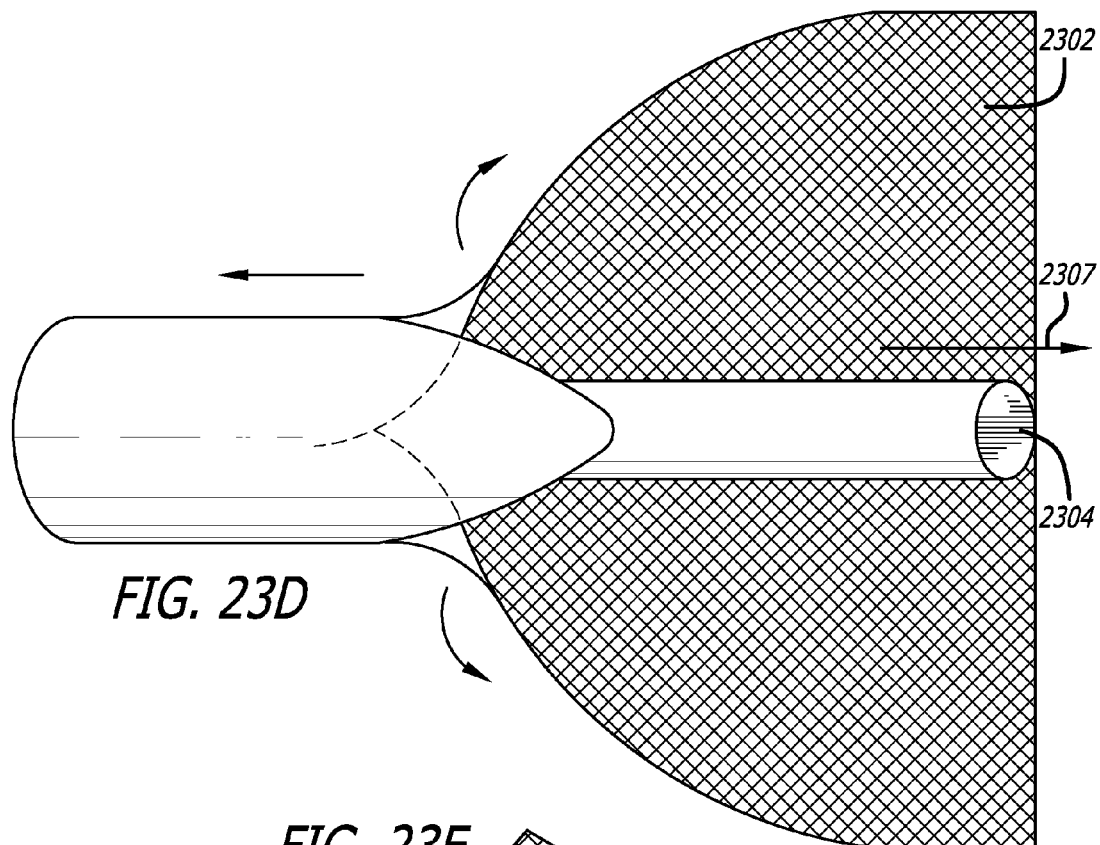

As depicted in FIGS. 23A through 23C, implantable mesh 2302 can be folded and/or stretched on a guide-wire (not illustrated) or on an internal sheath 2304 (that may also harbor a guide wire) in order to attain a cross section narrow enough to be preloaded into a second sheath 2305, this external second sheath includes a hollow portion 2306 of deployment applicator 2301, or similar delivery catheter associated with deployment applicator 2301.

In one embodiment, depicted by FIGS. 23A through 23B, the implantable device may be folded onto internal sheath 2304 and disposed within external sheath 2305, and is deployed when the device becomes unrestrained by external sheath 505.

In other embodiments, depicted by FIG. 23C, implantable device 2302 may be rolled onto itself and disposed within external sheath 2305. Implantable device 2302 may be deployed by removal of the external sheath 2305. For example, the apparatus may be deployed by pushing internal sheath 2304 or guide wire in a distal direction 2307 out from device 2301.

In some embodiments, deployment applicator 2301 may include a restraining member that is actuated by heat, electricity, or other means known in the art to release the mesh apparatus from its collapsed and restrained position to its relaxed and expanded position.

In one embodiment external sheath 2305 may include the subdermal catheter 1801 previously described or may be positioned within subdermal catheter 1801 along with cutting blade members 1902. In this embodiment cutting tool 102 includes a hollow end depicted in FIG. 21A.

Preferably, the collapsed applicator has a sufficiently narrow profile to be threaded through deployment applicator 2301 or subdermal catheter, previously described. The applicator is preferably inserted percutaneously through the incision made by cutting tool 102, or other hole or incision in the skin created by the various dissection devices described herein. While applicator 2301 may be used with handpiece 100, applicator 2301 can be deployed through any needle hole in a dermis. In one embodiment, the thickness of the implantable device when in a collapsed form, i.e., when folded, rolled, and/or stretched to be accommodated by the applicator, has an outer diameter of from about 0.65 mm to about 2.2 mm. Suitable delivery sheaths 2305 can have an outer diameter from about 1 mm to about 3.3 mm. In other embodiments, the outer diameter of the deployed device or delivery sheaths can be greater or smaller depending on the configuration of the dissection needle.

Figure 23E:
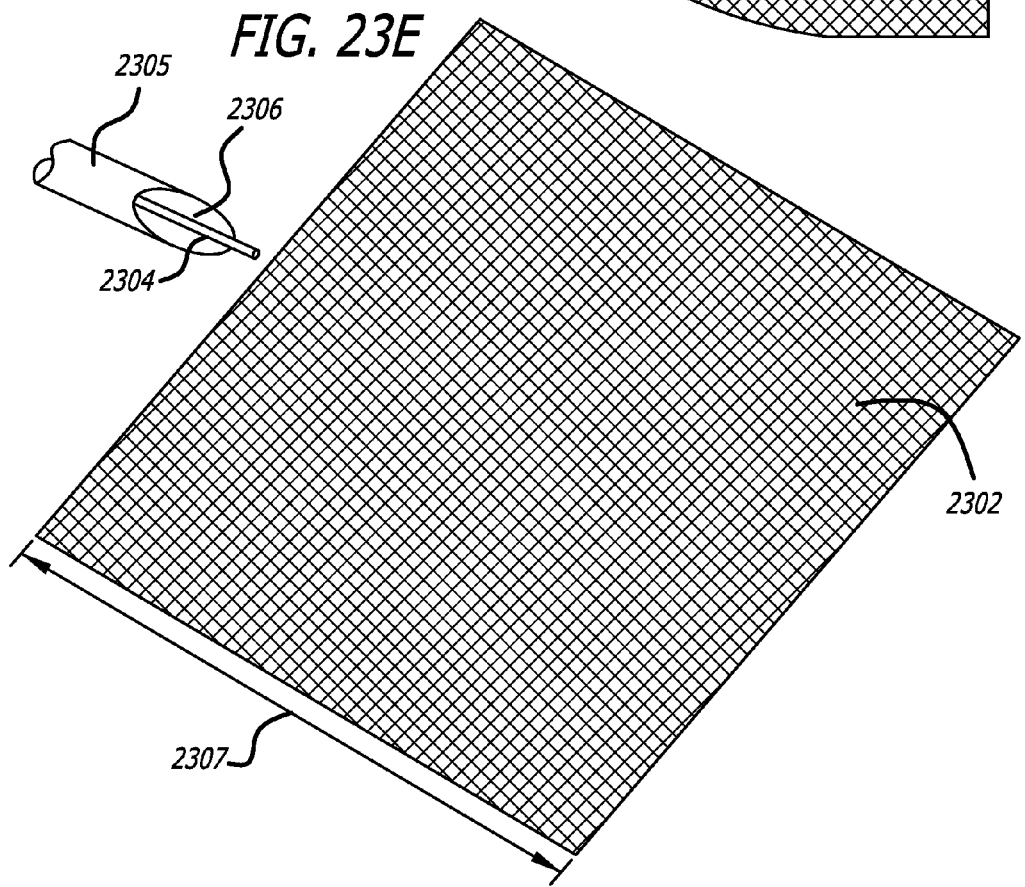

As illustrated by FIG. 23E, mesh 2302 (with or without a corresponding frame (not shown)), when in a relaxed and expanded form, has a length and/or width 2307 typically in a range from about 1 cm to about 5 cm. In other embodiments, the range may be up to 10 cm or higher depending on the size and configuration of the deployment applicator and dissection needle. Mesh 2302 is depicted as substantially square, but can be any shape suited to be placed in the subdermal fat or in the layer between the subdermal fat and the skin. For instance, and without limitations, the fully expanded mesh can be circular, rectangular, triangular, hexagonal, or even irregularly shaped.

Figure 24A:
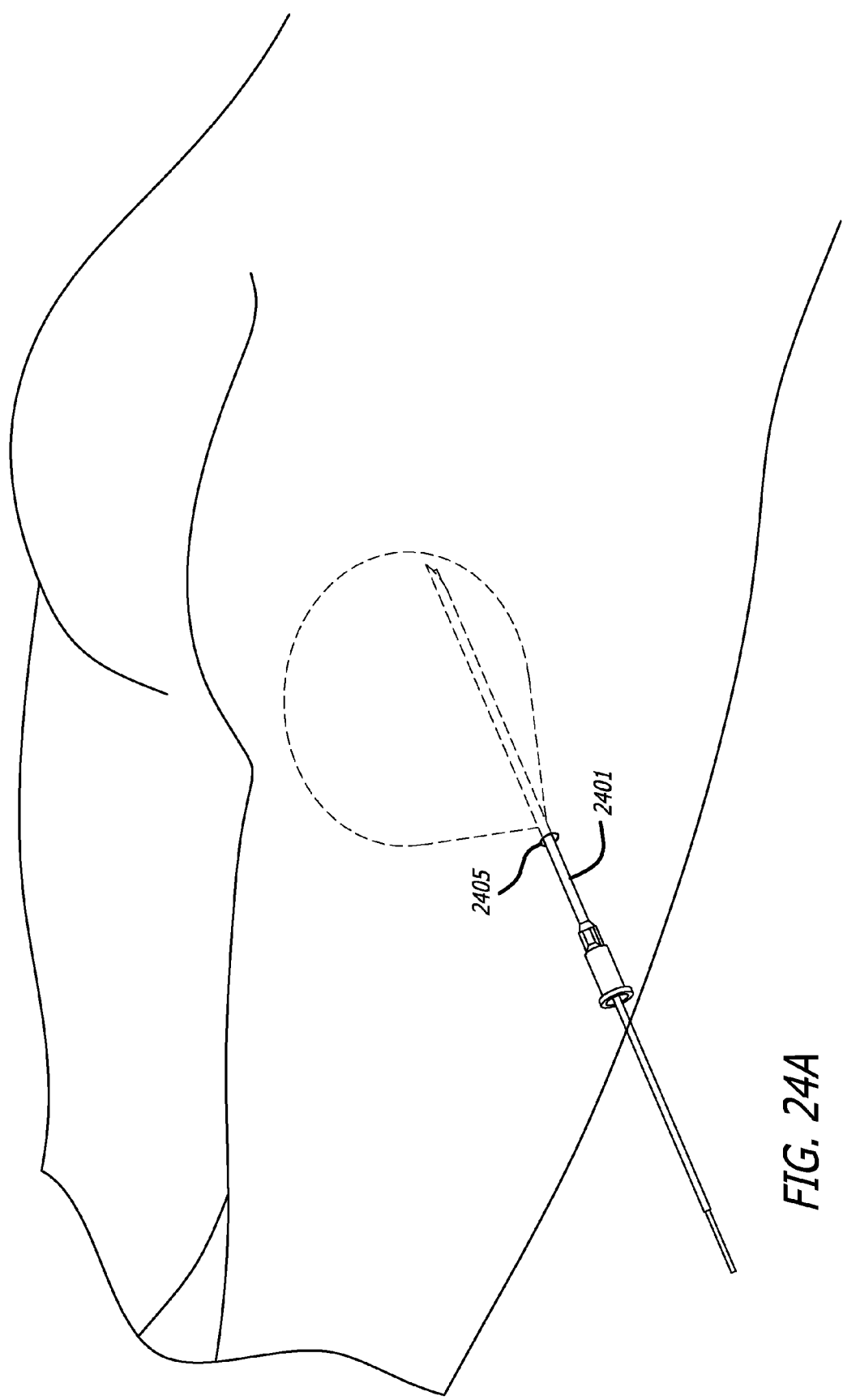
FIGS. 24A through 24B depict a second embodiment of a mesh deployment applicator, including a deployment shaft and keeper rod.
Figure 24D:
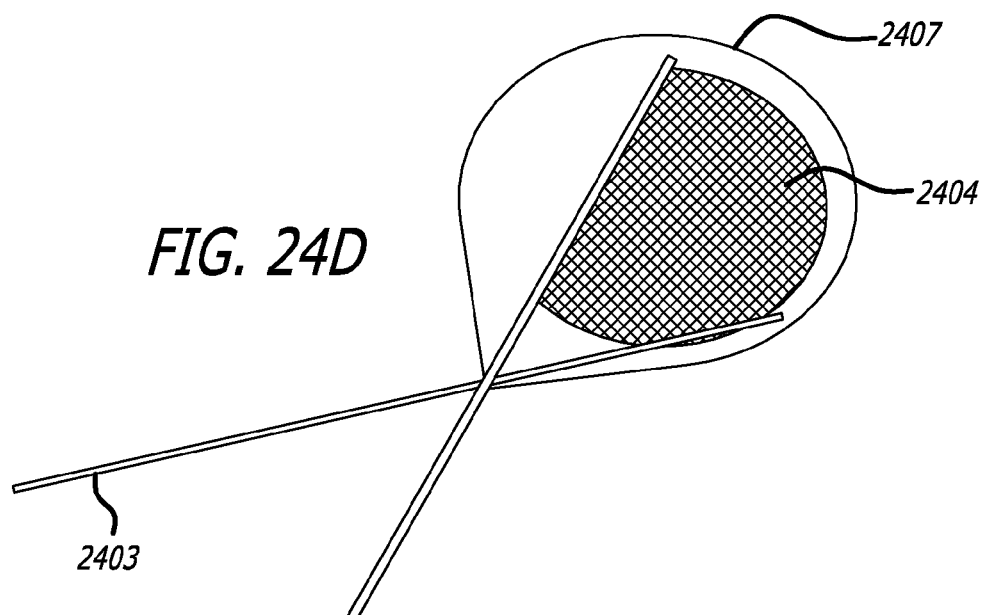
Figure 24E:
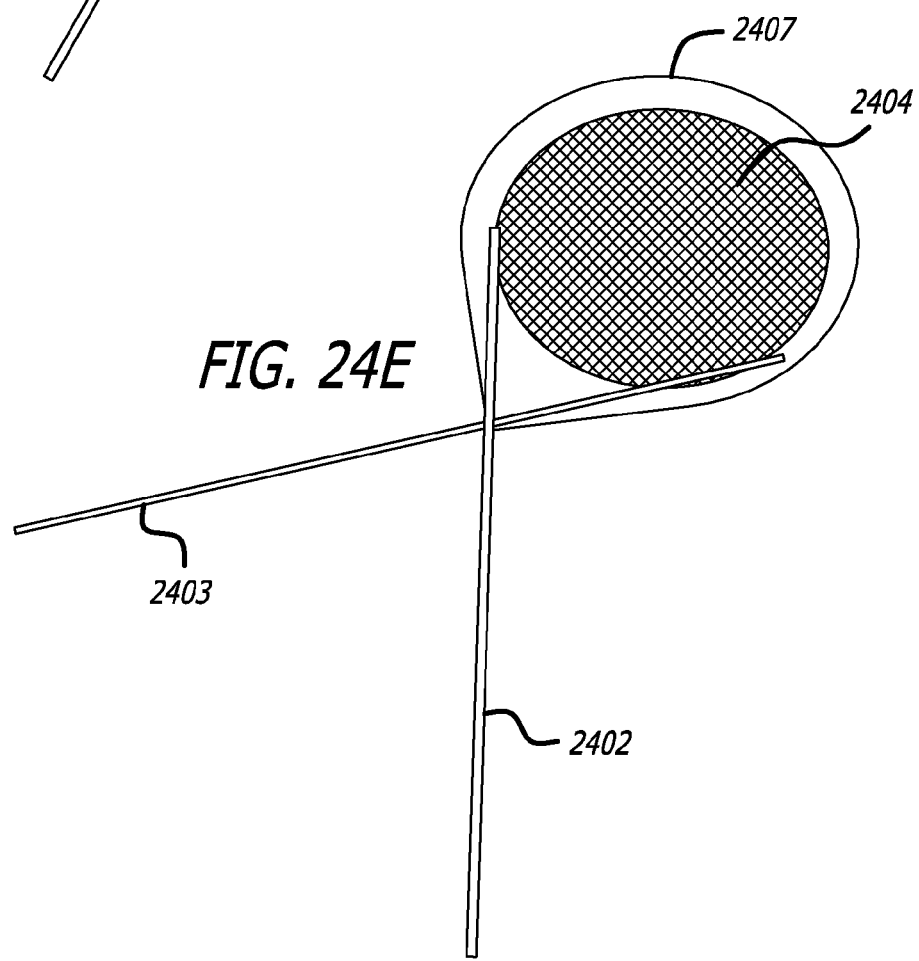
Figure 24F:
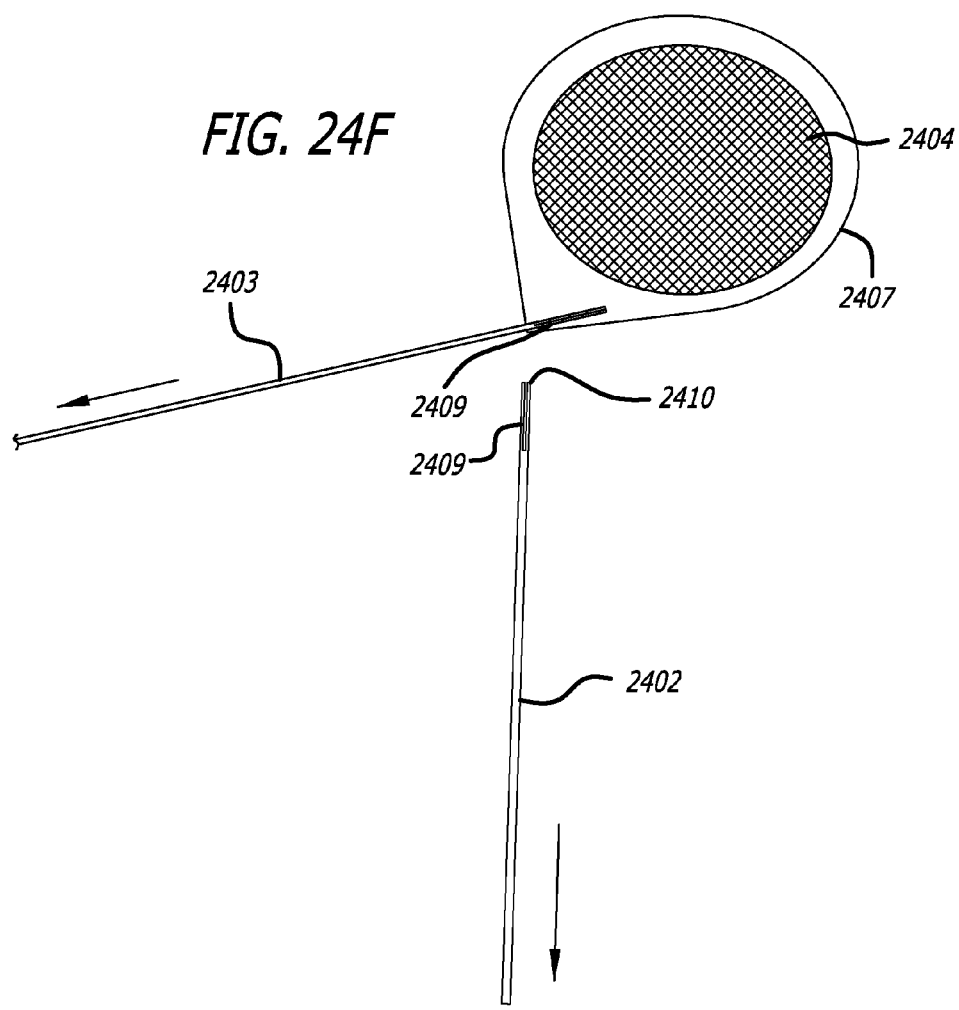

FIGS. 24A through 24F depict a second embodiment of a mesh deployment applicator. In this embodiment, a sheath 2305 may include or be interchangeable with an introducer needle 2401, and a guide wire may be omitted. A deployment shaft 2402 and keeper rod 2403 are disposed inside introducer needle 2401. Mesh 2404 is configured to be furled (i.e., rolled up) around shaft 2402 and keeper rod 2403. Introducer needle 2401 (with mesh inside) may then be inserted through an entry wound 2405 created by tool 102. After insertion, needle 2401 slides off over a proximal end 2406 of shaft 2402 and keeper rod 2403, leaving the furled mesh 2404 positioned with subcision region 2407. Shaft 2402 is simultaneously rotated about its longitudinal axis 2408 to un-furl mesh 2404, and pivoted about the skin-entry point 2405 to pull mesh 2404 across subcision region 2407. Keeper rod 2403 is maintained in a fixed position as mesh 2404 is un-furled, so as to anchor the edge of mesh 2404 at the desired location within subcision region 2407. As shown by FIG. 24C, shaft 2402 pivots 2408 about skin-entry point 2405, aided by the dissection handpiece 100 (discussed above). As mesh 2404 continues to be un-furled, a greater portion of mesh 2404 is deployed across treatment area 2407. FIG. 24E depicts mesh 2404 in a fully deployed position. As depicted in FIG. 24F, after deployment, keeper rod 2403 and shaft 2402 can then be withdrawn through entry point 2405, leaving mesh 2404 in the desired position within subcision region 2407. In one embodiment, a longitudinal slit 2409 is present on a distal end 2410 of shaft 2402 and keeper rod 2403. Mesh 2404 is secured when mesh 2404 is wrapped around shaft 2402 or keeper rod 2403, however, slits 2409 are open on distal end 2410, so when shaft 2402 and rod 2403 are withdrawn as illustrated, mesh 2404 slips off the end of shaft 2402 and rod 2403.

With reference to FIG. 16B, in some embodiments the system includes an energy device 1608. In accordance with these embodiments the insertable tool and/or handpiece may be configured to apply energy such as RF, ultrasound, or microwave energy to the tissue before or after the mesh has been inserted into the treatment area. Although not specifically illustrated, it should be understood that an appropriate energy source 1609 (ultrasound amplifier, RF amplifier, microwave) will need to be operably connected to handpiece 100. In some embodiments energy source 1608 may be used to create damage sites along the mesh that will heal as fibrous structures, and/or to shrink the mesh and create a tightening of the subcutaneous tissues. Energy device 1608 may include a microwave, conductive heat, ultrasound, or RF. In some embodiments the energy may also be applied to shrink the self-expanding implantable device after it has been deployed under the skin.

One method of using the present embodiments is directed to providing a handpiece (described above) configured to minimally invasively create a plane of dissection. The handpiece may be used to reduce the appearance of cellulite by cutting the fibrous structures between and which create the chambers of fat cells. Notably, it is the chamber of fat cells created by the fibrous structures which create the aesthetically unappealing dimpling known as cellulite. The chambers of fat cells and the fibrous structures which create them may lie in either the shallow fat layer or in the deeper fat layer. The handpiece and cutting tools are suitable for cutting the fibrous structures which may lie in the interface between the dermis and the fat, in the shallow fat layer 0-10 mm below the dermis, or in the deep fat layer 10-30 mm below the dermis. The handpiece of the present invention supports the cutting tool and enables the user to create a plane of dissection at a precisely defined depth and, if desired, deploy a mesh implant into the treatment area. If desired, the area of treatment may be injected with one of the commonly used anesthetic compounds or collagen promoting material. It should be understood that any of the cutting devices disclosed in this disclosure may be used with any of the mesh insertion methods and devices disclosed herein. The depth of the plane of dissection may be defined by the orthogonal distance from the tissue apposition (tissue facing) surface of the top wall to the tool insertion conduit.

With reference to FIGS. 9A and 9C, a physician first applies a reference mark 904 to the dermis to identify a cellulite dimple for treatment, and handpiece 100 is positioned on an outer portion of the skin 903 to be treated. Handpiece 100, including transparent cover 206, is subsequently placed over mark 904 on dermis 903 and a vacuum is applied. Mark 904 is then suctioned against the upper tissue apposition surface 203 such that mark 904 on dermis 902 is visible through the clear top portion 206 of handpiece 100. A reference feature 905 on handpiece 100 indicates the region that dissection will occur, and the physician verifies that mark 904 falls within the dissection region 902. FIG. 9C depicts handpiece 100 used in conjunction with a NOKOR™-like subcision device capable of cutting septae and infusing a tumescent solution, however, any cutting feature or device disclosed above may be used with this embodiment.

An embodiment of using the device includes percutaneously inserting a cutting tool through the epidermis of the skin and into the subdermal fat layer or in the layer between the fat and the skin.

(1) A first step, depicted by FIGS. 1A and 1B, includes capturing the tissue having dimpled cellulite into the recessed portion of the handpiece. In some embodiments this entails applying a manual pressure or force on the handpiece. In other embodiments this entails using a vacuum enabled handpiece to bring the tissue into contact with the recessed portion of the tissue apposition surface. Suction from a remote vacuum source 1606 (FIG. 16B) is supplied to one or more ports 208 (FIG. 2) in the handpiece to pull the tissue into a recess bounded on top and side surfaces. Precise depth control, where depth is measured orthogonally downward (into the tissue) from the dermis is believed to be an important factor in achieving consistent and uniform results. In other words, it is important to create a planar lesion at a fixed depth below the dermis. FIG. 2 depicts a portion of subcutaneous tissue 205 disposed within the recessed area of the handpiece.

(2) A deployable tool (102, 303, 1001, 2401) is then placed into and through the conduit in a side of the handpiece, such that the tool is placed in a precise tissue depth in the subdermal fat or in the layer between the fat and the skin. The tool may have a collapsible blade or may pierce the skin like a bayonet. In one embodiment the tool may be any cutting tool as described in previous paragraphs. In another embodiment the tool may be a hypodermic needle for anesthetic fluid administration. In another embodiment the tool may be a specialized larger diameter hypodermic needle, or subdermal catheter, configured to allow deployment of a cutting tool and/or other deployment devices through its center.

(3) Once in place, the cutting tool is actuated. In some embodiments, actuation of the cutting tool entails deployment of the cutting blades. In some embodiments, the cutting blade is simply inserted percutaneously through the dermis at a desired depth. In some embodiments, the cutting toll is an RF needle. The RF needle may be provided with a sharp tip for penetrating the dermis. In some embodiments, the tip may be blunt or beveled. Actuation of the RF needle entails supplying RF frequency current from an RF amplifier to the needle in either a cutting mode or in coagulation mode. To avoid damaging the dermis, it is desirable to supply the minimum amount of energy during cutting to avoid or minimize heating of the dermis.

Optionally, one or more cutting blades of the cutting tools are then deployed from the cutting tool. In one embodiment, deploying the cutting blades include actuating a control at a proximal end of the tool. The control may be actuated by a simple switch, lever, or control rod which is either pulled, turned or pushed to control actuation of the cutting blades. In some of the embodiments the cutting tool is not collapsed thus the un-collapsed cutting blade is percutaneously inserted and there is no need to deploy the cutting tool.

(4) The tool is then manipulated to sever the fibrous structures 220 (FIG. 2) between the skin and the fat at a precisely defined depth maintained by the handpiece and tissue apposition surface. In one embodiment the tool cuts on the reverse stroke as it is pulled back (retracted) 227 to sever fibrous structures 220. In another embodiment, the tool cuts on the forward stroke as the tool is deployed and pushed forward 228 to sever the fibrous structures. In a further embodiment the cutting tool is optionally moved in a forward and reverse direction, i.e. reciprocated. In a further embodiment conduit 213 is configured to provide some side-to-side movement parallel to the surface of the skin (FIG. 2B). In other words, the conduit is somewhat larger gauge than the cutting tool, thereby enabling the cutting tool to be pivoted in an arc from side-to-side. In a yet further embodiment advancement and sweeping of the tool during cutting is microprocessor controlled.

(5) After completion of the cutting of the fibrous septae, the tool is collapsed and/or removed from the tissue and the handpiece. Optionally, the cutting blades are then retracted by any of the means described for deploying the blades. Or as described above, in some embodiments there is no step of deploying or underdeploying the blade. In one embodiment the blades are retracted by moving the actuator in the opposite direction as it was moved to deploy the blades. In another embodiment the blades are retracted by moving the actuator in the same direction. As noted previously, some of the cutting tools may not utilize collapsing cutting blades in which case the cutting tool is simply withdrawn. Optionally, the users may sweep the cutting tool to verify a clean dissection of the fibrous structures. If resistance is encountered when sweeping the cutting tool then steps 4 and 5 may be repeated.

A further embodiment of using the device includes percutaneously inserting a mesh between the subdermal fat layers and the epidermis.

Figure 25:
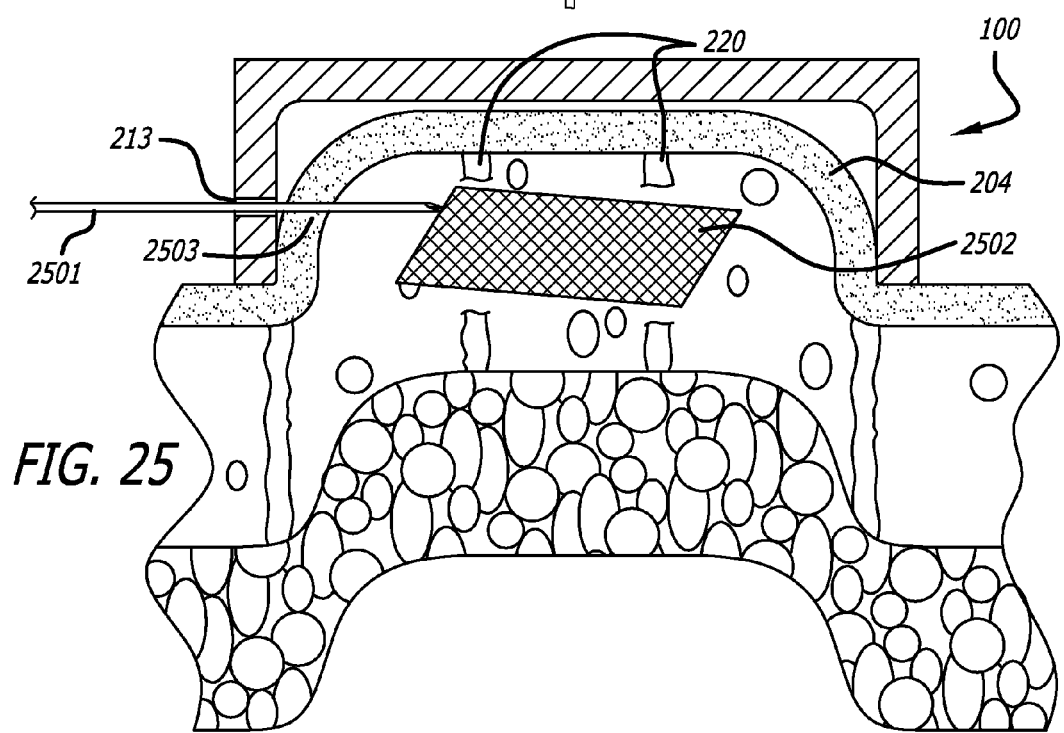
FIG. 25 depicts a cut-away side view of the handpiece in use with the mesh deployment applicator.

(1) Turning to FIG. 25, a mesh applicator 2501 is optionally placed into the treatment area through conduit 213 of handpiece 100. Mesh applicator 2501 contains a self-expandable mesh 2502 initially collapsed and small in shape. In further embodiments, in which handpiece 100 is not used, applicator 2501 is inserted through a needle-sized hole 2503 through dermis 204.

Mesh 2502 or other bio-absorbable implantable device is configured on a distal end of a mesh applicator. In one embodiment configuring the implantable device includes attaching the mesh to a self-expandable frame and placing the implantable device into a collapsed position retained at the distal end of the mesh applicator. In another embodiment the mesh is self-expandable and positioned in a collapsed form without the use of a frame.

(2) The distal end of mesh applicator 2501 is then inserted percutaneously into a treatment area between the subdermal fat layers and the epidermis.

(3) Once mesh applicator 2501 is placed into the tissue and into the treatment area via conduit 213 or hole in dermis 204, mesh 2502 is expanded in the tissue to stretch under the skin. In one embodiment the mesh 2502 self-expands when released from the applicator. In another embodiment mesh 2502 is deployed by a self-expanding frame. In a further embodiment the mesh is deployed by manually manipulating a shaft and keeper rod (FIGS. 24A-24F), and/or other percutaneous tools useful for deploying the mesh. Deployment of mesh may include any means described herein, including by applicator 2301 or by deployment shaft 2402 and keeper rod 2403 (via applicator 2401). Deployment of mesh 2502 may further include actuating a control to release a retaining mechanism retaining the implantable device in a collapsible form.

(4) Correct placement and alignment of mesh 2502 is then verified, if possible, by the treating physician.

(5) Once the mesh is deployed and verified, it is optionally secured in the treatment area. In one embodiment, the mesh 2502 is simply placed in the tissue. In one embodiment the implantable device may be anchored in place, and, anchors of suture, staple or other material is placed on the corners of the mesh to hold it in place. The implantable device may be anchored near its corners or outer edges, or any method which would secure the implantable device in place. The anchors may include quills, sutures or other structures which bind into the surrounding tissue. The implantable device may be textured or may have been treated on both sides to promote binding to both the skin side and the fat side. The implantable device may include a treatment on the implantable device including a growth-promoting chemical to encourage rapid in-growth into the implantable device from the body. In a further embodiment the implantable device may be textured or treated on one or more sides to promote binding to either the skin or the fat side. In a further embodiment, the mesh is coated with biologically acceptable glue on one or both sides and the tool stretches the mesh so that the glue can cure onto the skin and/or fat. The mesh preferably covers the treatment area including severed fibrous structures 220 that were previously severed by cutting tool 102 or other cutting implement described herein.

(6) Once the mesh is in place and/or anchored, the mesh applicator is then retracted from the tissue and the treatment area. In certain embodiments, this step may also include removing applicator 2501 from handpiece 100. If a mesh deployment frame was used this step may first include applying a form of heat to shrink the frame, or using a control to retract the frame prior to removing the mesh applicator from the tissue.

(7) Once the mesh is implanted, a thermal energy such as microwave, conductive heat, ultrasound, RF may be applied to the tissue after the mesh is in place. In one embodiment, energy is then applied to the tissue after the mesh is in place. In one embodiment, the energy may be used to create damage sites along the mesh that will heal as fibrous structures, and/or to shrink the mesh and create a tightening of the subcutaneous tissues. In another embodiment, a thermal energy such as microwave, conductive heat, ultrasound, RF may be applied to shrink the implant as it is in place in the subdermal fat and create a tightening of the subcutaneous tissues. In another embodiment the thermal energy may be applied to shrink the self-expanding mesh deployment frame. When the proper heat is applied to the frame the frame will constrict to its collapsed form for easy withdrawal of the device from the tissue.

In some embodiments, a treatment solution may be injected into the cutting area at or between any step of cutting inside the tissue. The treatment solution may also be injected prior or after deployment of the blades and/or cutting steps. The treatment solution may include a local anesthetic or pain relieving solution, a vasoconstrictive agent, or an antibiotic, or a combination of treatment solutions useful in similar medical procedures. If the cutting tool includes the application of energy the treatment solution may be selected to enhance the delivery of energy. For example, if the cutting tool is an RF electrode, the treatment solution may include saline or like conductive solution to prevent charring of the tissue. It may be desirable to control such energy based on the measurement of an applicable parameter such as tissue impedance or temperature. As someone with ordinary skill in the art would realize, such feedback control would be comprised of a microprocessor based algorithm. As used throughout this disclosure, any reference to applying energy should be understood to define the application of one of radiofrequency (RF), ultrasound, microwave, or thermal energy.

Figure 26A:
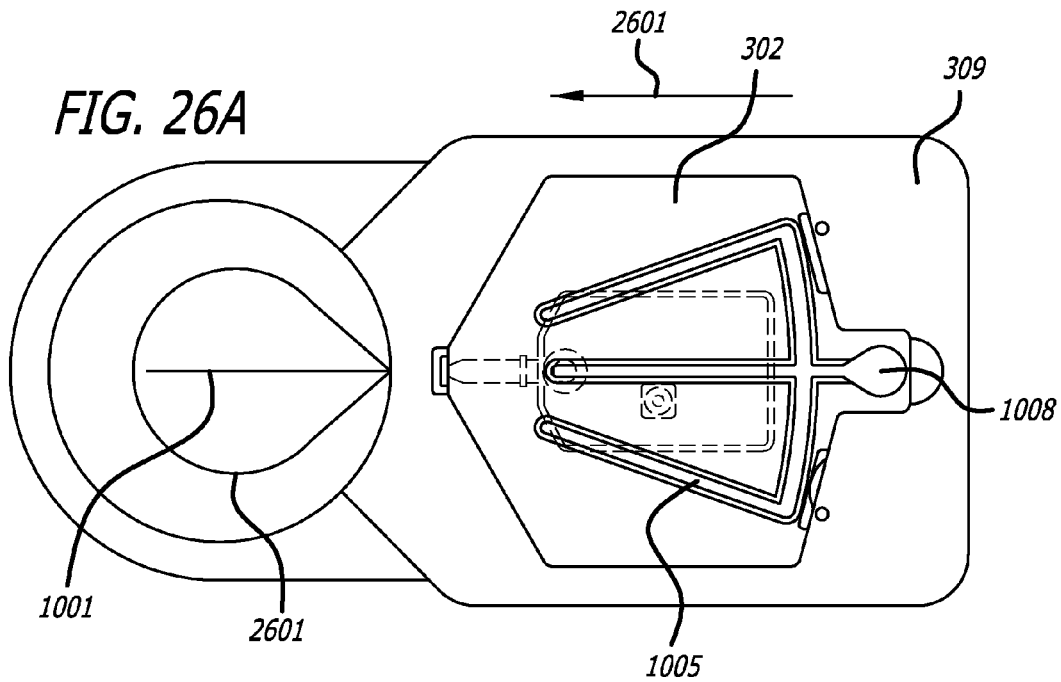
FIGS. 26A and 26B depict the handpiece and guidance track for use with a solution injection device.
Figure 26B:
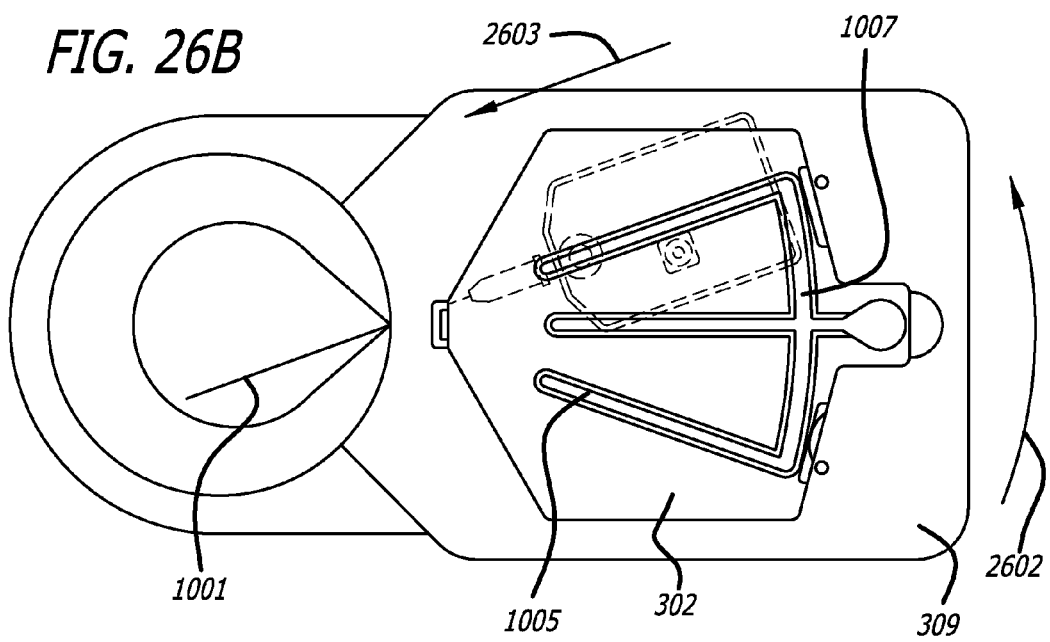

As in previous embodiments, and as depicted by FIGS. 26A and 26B, and with further reference to FIG. 10A, a treatment solution may be inserted prior to or after the dissection process. Injection device 1004 is inserted into the guide track 302 preferably at entry point 1008. The tissue to be treated is disposed in recessed area 105 as previously described. Needle 1001 may then be easily guided through conduit 213 and entry hole 214 and into the tissue by moving injection device 1004 along any of radial tracks 1005 toward handpiece 100. For example, injection device 1004 is first moved down the central channel in a forward direction 2601 to directly insert needle 1001 into the tissue. The treatment solution is then injected using needle 1001 manually using syringe 1003 or, in some embodiments, by a microprocessor driven injection pump (e.g., FIG. 15). After the solution is injected needle 1001 is removed by reversing direction along track 1005. Injection device may then be rotatively moved in an arc 2602 along cross-track 1007 to be positioned in an alternate radial track 1005. Injection device 1004 is then moved a second time down radial track 1005 in a forward direction 2603 to insert needle 1001 into a further location within the treatment area. Needle 1001 passes through the same entry point 214 while the widened shape of conduit 213 allows repositioning of needle 1001 with respect to rotational angle 2602 and radial tracks 1005. The process may then be again repeated for the third track 1005, or as many times as is determined to be necessary by the treating physician. In some embodiments, needle 1001 is a 22 gauge multi-holed, single-use needle. Needle 1001 includes multiple holes along its sides so as to, once it is fully inserted, saturate the tissue along its injection path. Injecting the solution along the paths set by the disclosed injection guidance track, thus allows a solution, such as an anesthetic and/or a vasoconstrictor, to fully saturate the treatment area while providing precise needle guidance and specific depth. It has been found that the method reduces the number of needle sticks necessary to infuse the area to be treated, increases anesthesia effectiveness, and substantially minimizes pain. Because the handpiece remains in the same position between solution injection and dissection (subcision) locality of anesthesia relative to dissection is assured, and the swappable guidance track provides rapid switching between medicament delivery and dissection and vice versa so as to increase fluid retention throughout the process. Furthermore, the modularity of the platform and guidance track ensures that the process is repeatable and scalable.

The device allows for three-dimensional control of treatment solution delivery and dissection of subcutaneous tissues, not realized by present art. The device typically controls a depth of between 4 mm and 20 mm below the surface of skin; however, a depth lower than 4 mm or greater than 20 mm is contemplated. The range of motion in the lateral direction is controlled by the effective length of the needle or blade or other cutting device, however, typically encompasses an area of between 2 mm and 50 mm in either direction. As the cutting device is disposed further into the subcutaneous space larger areas are achievable.

Figure 27A:
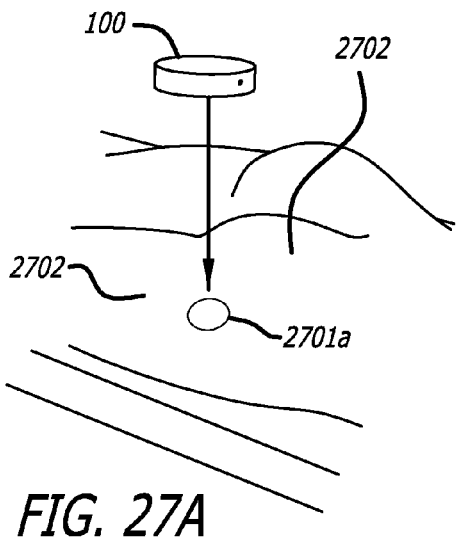
FIGS. 27A through 27D depict a method of using the handpiece and cutting tool on a dermis, including partially overlapping adjacent treatment areas.

It is generally recognized that a large treatment site heals more slowly than a series of smaller treatment sites. Moreover, the larger the treatment site the greater the risk of seromas, uneven healing, fibrosis, and even skin necrosis. Turning to FIGS. 27A through 27D, this problem is addressed, in one embodiment, by utilizing a adjustable depth feature (e.g., FIGS. 12, 13, 14). Each treatment site 2701 is an island surrounded by tissue 2702 which has not been treated (the fibrous septae have not been severed at the same plane). As depicted by FIG. 27A, handpiece 100 is used to treat a first treatment area 2701. In some embodiments, after the tissue within the first treatment site is treated, the handpiece can be repositioned on a different treatment area 2701 at the same, or at a different or alternating depth as, for example, in a checkerboard fashion.

Figure 27B:
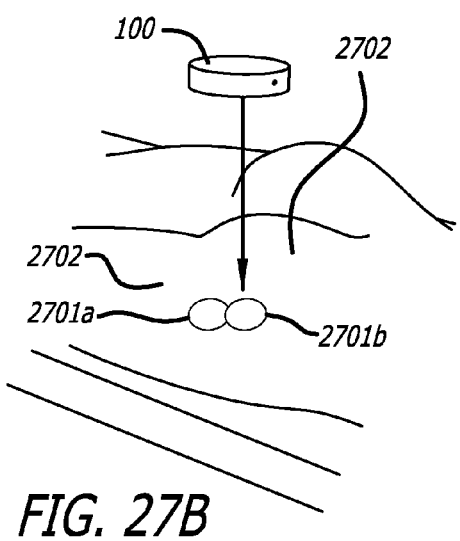
Figure 27C:
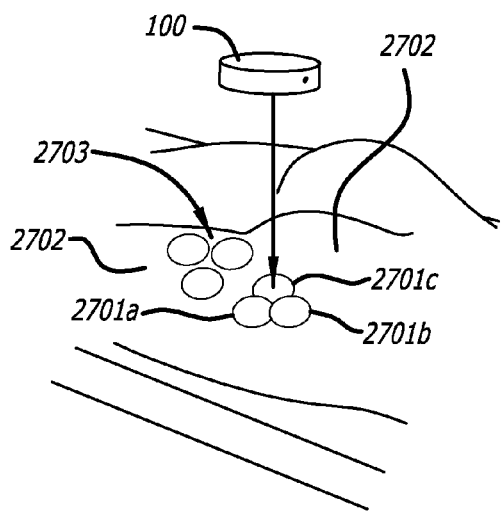
Figure 27D:
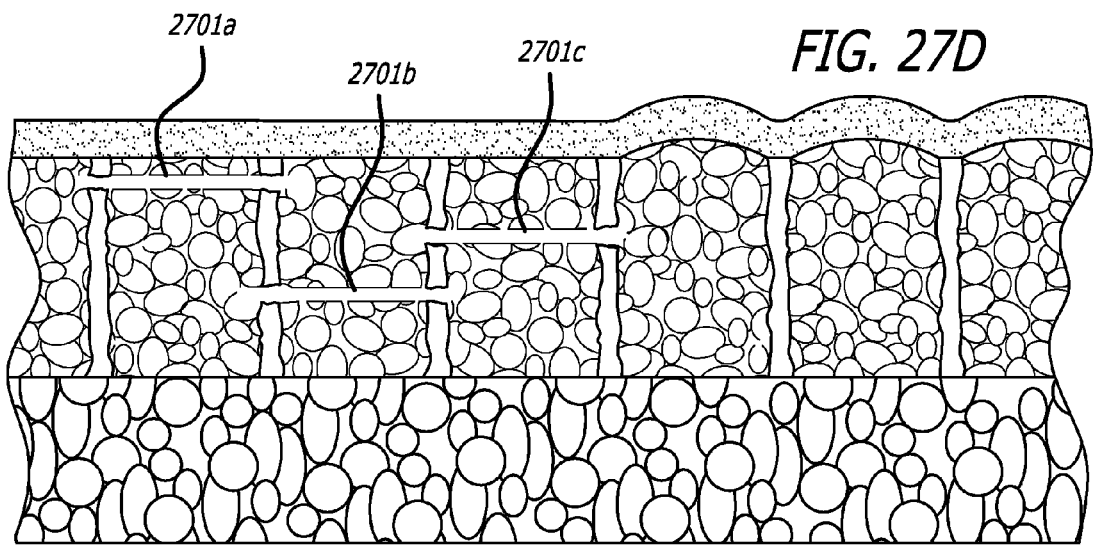

According to further embodiments, a relatively large treatment area is divided into a plurality of smaller treatment sites. FIGS. 27B and 27C show two or more treatment sites 2701a, 2701b, 2701c surrounded by untreated tissue 2702. In some embodiments, the spacing in the X-Y plane (parallel to the dermis) between adjacent treatment sites is reduced or eliminated. In some embodiments, the treatment sites could even overlap. Zero spacing (or overlapping) between adjacent sites is possible if adjacent treatment sites are at different treatment depths (measured perpendicularly from the dermis) and the bridge of untreated tissue can be greatly diminished without impacting the tissue healing time. In the embodiment depicted by FIG. 27C, treatment sites 2701a and 2701c are at a different treatment depth than 2701b. According to a further embodiment, treatment sites may not be contiguous, meaning that there are no multiple connected lesions. For instance, a further treatment area may include unconnected treatment sites 2703.

According to yet another aspect of the invention, adjacent treatment sites 2701 touch or even overlap but are at different treatment depths (measured in a direction perpendicular from the dermis). Thus, from a top view (FIG. 27C) the plurality of treatment zones 2701a, 2701b, 2701c appear to be continuous, but from a side view, depicted by FIG. 27D, it is clear that the "checkerboard" lesions 2701a, 2701b, 2701c are at different treatment depths. In other words, adjacent sites are at different treatment depths.

The interspersing of treatment sites at different treatment depths is believed to accommodate rapid healing. More specifically, the interspersing of treatment sites at different treatment depths allows for closer spacing between treatment sites while accommodating for a more rapid healing response time of the injured tissue. As the treatment area(s) heal, the tissue in the treated subcutaneous area regrows with minimal adipose tissue and minimal thickness such as to alleviate and substantially reduce the appearance of cellulite.

According to yet another aspect of the invention, the benefits realized by the multiple depth treatment enabled by the embodiments may be based on the severity of the specific lesion(s) or the specific area on the body being treated. For instance, it may be desirable to treat a deeper lesion at a deeper depth. Dimples or lesions on the thighs, for example, may be treated at a different depth than lesions on the buttocks. According to yet another aspect of the invention, the size of the dissection may also be adjusted by incomplete or partial movement of the cutting means within the guidance track. For example, with reference to FIGS. 6A and 6B, a smaller area may be treated than the total area accessible by guidance track 302 by not completing movement of the cutting module throughout all the arcs 602 or by not moving laterally as far along the arcs.

Figure 28:
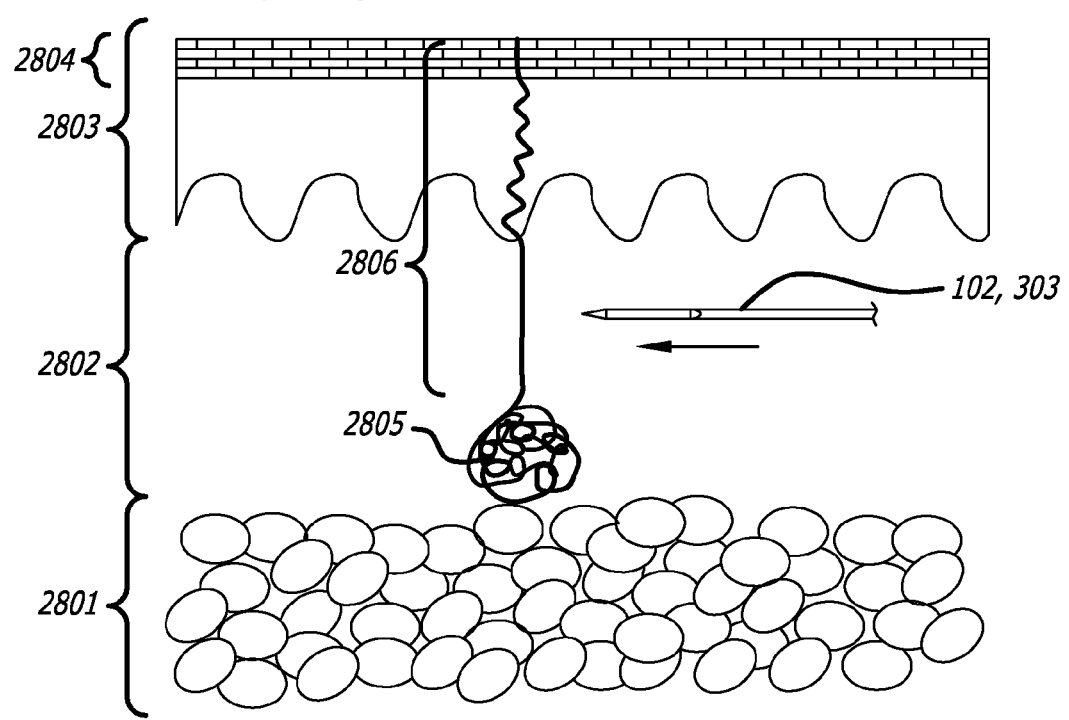
FIG. 28 depicts the dissection device in use in a method for severing an endocrine sweat gland.

FIG. 28 is a sectional view of human tissue showing subcutaneous fat layer 2801, dermis 2802, epidermis 2803, Eccrine sweat gland 2805, and Eccrine duct 2806. As shown in FIG. 28, the sweat gland 2805 is found proximate the interface between the dermis and the fat layer 2801. The above-described handpiece 100 and any of the cutting devices disclosed herein may be used to either sever eccrine sweat gland 2805 from eccrine duct 2806 or injure the eccrine sweat gland to halt the excretion of sweat. This would be particularly advantageous for treating hyperhidrosis in which the sweat gland produces an excessive amount of sweat. Severing the sweat duct may provide permanent relief if the duct does not regenerate or reconnect with the sweat gland. Similarly, damaging the sweat gland may provide permanent relief if the sweat gland is sufficiently injured to permanently disable the gland.

The forgoing description for the preferred embodiments of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

Although the present invention has been described in detail with regard to the preferred embodiments and drawings thereof, it should be apparent to those of ordinary skill in the art that various adaptations and modifications of the present invention may be accomplished without departing from the spirit and the scope of the invention. Accordingly, it is to be understood that the detailed description and the accompanying drawings as set forth hereinabove are not intended to limit the breadth of the present invention.

We claim:

1. A minimally invasive skin treatment device, comprising:
   a handpiece having a perimeter elevation defining a perimeter surface and a top which cooperatively define a recessed area, an inner side of the perimeter elevation and the top defining an apposition surface facing into the recessed area;
   a cutting tool configured to at least partially extend through the perimeter elevation and into the recessed area; and
   a guidance track operably connected to the handpiece, wherein the guidance track is configured to constrain a portion of the cutting tool in association with the guidance track to move along a predetermined path to cooperatively move a distal end of the cutting tool within the recessed area in a plane substantially parallel to the top of the handpiece and within a region of a predetermined shape defined by the predefined path;
   a conduit extending through the perimeter elevation and having an entry hole disposed on an inner side of the conduit and facing said recessed area, said entry hole defining a tool pivot point when a distal end of the cutting tool is inserted through the conduit and into the recessed area so that the distal end of the cutting tool can move laterally side to side within the recessed area.

2. The minimally invasive skin treatment device of claim 1, further comprising:
   a platform operatively connected to the handpiece, wherein the platform includes the guidance track; and
   a guide pin operably connected to the tool, said guide pin slidably engaging the guidance track such that the tool is constrained to move in accordance with the predetermined path.

3. The minimally invasive skin treatment device of claim 2, wherein the platform is fixed with respect to the handpiece and substantially orthogonal to a bottom edge of the handpiece.

4. The minimally invasive skin treatment device of claim 2, wherein the guidance track forms a groove in a top of the platform.

5. The minimally invasive skin treatment device of claim 2, wherein the guidance track includes an undercut portion and the guide pin has an enlarged head such that the interference between the enlarge head and the undercut portion of the guidance track inhibits removal of the enlarged head from the guidance track while permitting the guide pin to be moved in accordance with the predetermined path.

6. The minimally invasive skin treatment device of claim 1, wherein the cutting tool comprises:
   a cutting blade; and
   a reciprocating motor coupled to the cutting blade, said reciprocating motor reciprocating the cutting blade.

7. The minimally invasive skin treatment device of claim 6, the cutting tool further comprising a sleeve, wherein the cutting blade is at least partially slidably disposed within the sleeve.

8. A minimally invasive skin treatment device, comprising:
   a handpiece having a perimeter elevation defining a perimeter surface and a top which cooperatively define a recessed area, an inner side of the perimeter elevation and the top defining an apposition surface facing into the recessed area;
   a cutting tool configured to at least partially extend through the perimeter elevation and into the recessed area; and
   a guidance track operably connected to the handpiece, wherein the guidance track is configured to constrain a portion of the cutting tool in association with the guidance track to move along a predetermined path to cooperatively move a distal end of the cutting tool within the recessed area in a plane substantially parallel to the top of the handpiece and within a region of a predetermined shape defined by the predefined path;
   wherein the top of the handpiece is configured to be adjustable and configured to change the distance between an inner side of the top of the handpiece and a bottom edge of the perimeter elevation and to change a volume of the recessed area when the top is adjusted; and
   wherein the top of the handpiece comprises a reversible lid, configured to be disconnected from the handpiece, turned over, and reconnected in order to adjust the volume of the recessed area.

9. A minimally invasive skin treatment device, comprising:
   a handpiece having a perimeter elevation and a top which cooperatively define a recessed area, an inner side of the perimeter elevation and the top defining an apposition surface facing into the recessed area;
   a cutting tool configured to at least partially extend through the perimeter elevation and into the recessed area; and
   a guidance track operably connected to the handpiece, wherein the guidance track is configured to constrain a portion of the cutting tool in association with the guidance track to move along a predetermined path to cooperatively move a distal end of the cutting tool within the recessed area in a plane substantially parallel to the top of the handpiece and within a region of a predetermined shape defined by the predefined path;
   wherein the top of the handpiece is configured to be adjustable and configured to change the distance between an inner side of the top of the handpiece and a bottom edge of the perimeter elevation and to change a volume of the recessed area when the top is adjusted; and
   wherein the top of the handpiece is operably connected to a perimeter wall of the perimeter elevation by a threaded engagement, the top of the handpiece being rotatably mounted to the perimeter wall, and wherein rotation of the top relative to the perimeter wall adjusts the volume of the recessed area.

10. The minimally invasive skin treatment device of claim 9, the top of the handpiece comprising:

an upper rim disposed between an upper edge of an outer wall and an upper edge of inner wall;

a recessed surface disposed at a bottom edge of the inner wall, a perimeter of the recessed surface being substantially defined by a bottom edge of the inner wall; and a first and second reference mark, the first reference mark being spaced a rotational distance from the second reference mark such that the rotational distance corresponds to predetermined vertical distance along the threaded engagement.

11. The minimally invasive skin treatment device of claim 9, further comprising an o-ring interposed between the top of the handpiece and the perimeter wall of the handpiece.

12. The minimally invasive skin treatment device of claim 1, further comprising a elastomeric septum, the elastomeric septum being configured to be pierced by the cutting tool and to substantially self-seal when the cutting tool is removed such as to substantially prevent a vacuum leakage from the recessed area when a vacuum is supplied to the recessed area.

13. The minimally invasive skin treatment device of claim 1, further comprising:

a vacuum fitting operably connected to one of the top and the perimeter elevation and in fluid communication with the recessed area.

14. The minimally invasive skin treatment device of claim 13, further comprising:

a vacuum pump in fluid communication with the vacuum fitting, wherein the vacuum pump is configured to supply a suction force to the recessed area and configured to pull a tissue snugly and securely against the apposition surface when the recessed area is placed over the tissue.

* * * * *